US010494436B2

(12) United States Patent
Van Eenennaam et al.

(10) Patent No.: US 10,494,436 B2
(45) Date of Patent: Dec. 3, 2019

(54) ANTI-PD-1 ANTIBODIES

(71) Applicant: ADURO BIOTECH HOLDINGS, EUROPE B.V., Oss (NL)

(72) Inventors: Hans Van Eenennaam, Oss (NL); Andrea Van Elsas, Oss (NL); Joost Kreijtz, Oss (NL); David Lutje Hulsik, Oss (NL); Carlos Ricardo Rodrigues Dos Reis, Oss (NL)

(73) Assignee: ADURO BIOTECH HOLDINGS, EUROPE B.V., Oss (NL)

( * ) Notice: Subject to any disclaimer, the term of this patent is extended or adjusted under 35 U.S.C. 154(b) by 98 days.

(21) Appl. No.: 15/663,136

(22) Filed: Jul. 28, 2017

(65) Prior Publication Data
US 2018/0030137 A1    Feb. 1, 2018

(30) Foreign Application Priority Data

Jul. 29, 2016 (NL) ..................... 2017267

(51) Int. Cl.
| A61K 35/12 | (2015.01) |
| C07K 16/28 | (2006.01) |
| A61K 35/74 | (2015.01) |
| A61K 39/395 | (2006.01) |
| A61K 45/06 | (2006.01) |
| C07K 16/30 | (2006.01) |
| G01N 33/574 | (2006.01) |
| G01N 33/68 | (2006.01) |

(52) U.S. Cl.
CPC .......... *C07K 16/2818* (2013.01); *A61K 35/12* (2013.01); *A61K 35/74* (2013.01); *A61K 39/39558* (2013.01); *A61K 45/06* (2013.01); *C07K 16/30* (2013.01); *G01N 33/57492* (2013.01); *G01N 33/6872* (2013.01); *C07K 2317/24* (2013.01); *C07K 2317/33* (2013.01); *C07K 2317/34* (2013.01); *C07K 2317/55* (2013.01); *C07K 2317/56* (2013.01); *C07K 2317/565* (2013.01); *C07K 2317/732* (2013.01); *C07K 2317/734* (2013.01); *C07K 2317/74* (2013.01); *C07K 2317/76* (2013.01); *C07K 2317/92* (2013.01); *C07K 2317/94* (2013.01); *G01N 2333/70521* (2013.01)

(58) Field of Classification Search
CPC ....................................... A61K 35/12
See application file for complete search history.

(56) References Cited

U.S. PATENT DOCUMENTS

| 4,439,196 A | 3/1984 | Higuchi |
| 4,447,224 A | 5/1984 | Decant, Jr. et al. |
| 4,447,233 A | 5/1984 | Mayfield |
| 4,487,603 A | 12/1984 | Harris |
| 4,596,556 A | 6/1986 | Morrow et al. |
| 4,790,824 A | 12/1988 | Morrow et al. |
| 4,816,567 A | 3/1989 | Cabilly et al. |
| 4,941,880 A | 7/1990 | Burns |
| 4,946,778 A | 8/1990 | Ladner et al. |
| 5,064,413 A | 11/1991 | McKinnon et al. |
| 5,225,539 A | 7/1993 | Winter |
| 5,260,203 A | 11/1993 | Ladner et al. |
| 5,312,335 A | 5/1994 | McKinnon et al. |
| 5,383,851 A | 1/1995 | McKinnon et al. |
| 5,399,163 A | 3/1995 | Peterson et al. |
| 5,413,923 A | 5/1995 | Kucherlapati et al. |
| 5,480,792 A | 1/1996 | Buechler et al. |
| 5,525,524 A | 6/1996 | Buechler et al. |
| 5,530,101 A | 6/1996 | Queen et al. |
| 5,532,210 A | 7/1996 | Shen |
| 5,545,806 A | 8/1996 | Lonberg et al. |
| 5,569,825 A | 10/1996 | Lonberg et al. |
| 5,571,698 A | 11/1996 | Ladner et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,637,483 A | 6/1997 | Dranoff et al. |
| 5,648,260 A | 7/1997 | Winter et al. |
| 5,661,016 A | 8/1997 | Lonberg et al. |
| 5,677,425 A | 10/1997 | Bodmer et al. |
| 5,679,526 A | 10/1997 | Buechler et al. |
| 5,693,761 A | 12/1997 | Queen et al. |
| 5,693,762 A | 12/1997 | Queen et al. |

(Continued)

FOREIGN PATENT DOCUMENTS

| EP | 0154316 A2 | 9/1985 |
| EP | 0401384 B1 | 3/1996 |

(Continued)

OTHER PUBLICATIONS

Paul, Fundamental Immunology, 3rd Edition, 1993, pp. 292-295 (Year: 1993).*

(Continued)

*Primary Examiner* — Sheela J. Huff
(74) *Attorney, Agent, or Firm* — Acuity Law Group, PC; Michael A. Whittaker

(57) ABSTRACT

The present invention relates to anti-PD-1 antibodies, as well as use of these antibodies in the treatment of diseases such as cancer and infectious disease. These antibodies have CDRs as provided in the enclosed sequences. Also part of the invention are nucleic acids encoding these antibodies, expression vectors comprising such nucleotide sequences and host cells that comprise said nucleotide sequences or expression vectors.

13 Claims, 6 Drawing Sheets

Specification includes a Sequence Listing.

(56) References Cited

U.S. PATENT DOCUMENTS

| | | |
|---|---|---|
| 5,714,350 A | 2/1998 | Co et al. |
| 5,807,715 A | 9/1998 | Morrison et al. |
| 5,814,318 A | 9/1998 | Lonberg et al. |
| 5,821,337 A | 10/1998 | Carter et al. |
| 5,824,799 A | 10/1998 | Buechler et al. |
| 5,851,776 A | 12/1998 | Valkirs |
| 5,859,205 A | 1/1999 | Adair et al. |
| 5,869,046 A | 2/1999 | Presta et al. |
| 5,885,527 A | 3/1999 | Buechler |
| 5,904,920 A | 5/1999 | Dranoff et al. |
| 5,922,615 A | 7/1999 | Nowakowski et al. |
| 5,932,448 A | 8/1999 | Tso et al. |
| 5,939,272 A | 8/1999 | Buechler et al. |
| 5,939,598 A | 8/1999 | Kucherlapati et al. |
| 5,947,124 A | 9/1999 | Buechler et al. |
| 5,985,290 A | 11/1999 | Jaffee et al. |
| 5,985,579 A | 11/1999 | Buechler et al. |
| 6,005,079 A | 12/1999 | Casterman et al. |
| 6,019,944 A | 2/2000 | Buechler |
| 6,033,674 A | 3/2000 | Jaffee et al. |
| 6,054,297 A | 4/2000 | Carter et al. |
| 6,057,098 A | 5/2000 | Buechler et al. |
| 6,096,002 A | 8/2000 | Landau |
| 6,113,855 A | 9/2000 | Buechler et al. |
| 6,121,022 A | 9/2000 | Presta et al. |
| 6,129,914 A | 10/2000 | Weiner et al. |
| 6,143,576 A | 11/2000 | Buechler |
| 6,165,745 A | 12/2000 | Ward et al. |
| 6,180,370 B1 | 1/2001 | Queen et al. |
| 6,194,551 B1 | 2/2001 | Idusogie et al. |
| 6,277,368 B1 | 8/2001 | Hiserodt et al. |
| 6,277,375 B1 | 8/2001 | Ward |
| 6,329,511 B1 | 12/2001 | Vasquez et al. |
| 6,331,415 B1 | 12/2001 | Cabilly et al. |
| 6,350,445 B1 | 2/2002 | Jaffee et al. |
| 6,350,861 B1 | 2/2002 | Co et al. |
| 6,407,213 B1 | 6/2002 | Carter et al. |
| 6,620,135 B1 | 9/2003 | Weston et al. |
| 6,797,492 B2 | 9/2004 | Daugherty et al. |
| 6,946,292 B2 | 9/2005 | Kanda et al. |
| 7,029,872 B2 | 4/2006 | Gerngross |
| 7,125,689 B2 | 10/2006 | Carr et al. |
| 7,157,238 B2 * | 1/2007 | Schmitt ............. A61K 51/1027 435/7.92 |
| 7,214,775 B2 | 5/2007 | Hanai et al. |
| 7,449,308 B2 | 11/2008 | Gerngross et al. |
| 7,592,326 B2 | 9/2009 | Karaolis |
| 7,657,380 B2 | 2/2010 | Lazar et al. |
| 7,659,378 B2 * | 2/2010 | Han ..................... C07K 16/22 530/387.1 |
| 7,709,458 B2 | 5/2010 | Karaolis et al. |
| 8,008,449 B2 | 8/2011 | Korman et al. |
| 8,354,509 B2 | 1/2013 | Carven et al. |
| 2002/0150588 A1 | 10/2002 | Allison et al. |
| 2005/0281783 A1 | 12/2005 | Kinch et al. |
| 2010/0150946 A1 | 6/2010 | Jooss et al. |
| 2014/0193427 A1* | 7/2014 | Lerner .................. C07K 16/22 424/158.1 |
| 2015/0203579 A1 | 7/2015 | Papadopoulos et al. |

FOREIGN PATENT DOCUMENTS

| | | |
|---|---|---|
| EP | 404097 B1 | 9/1996 |
| WO | 8801649 A1 | 3/1988 |
| WO | 9211018 A1 | 7/1992 |
| WO | 9311161 A1 | 6/1993 |
| WO | 9404678 A1 | 3/1994 |
| WO | 9425591 A1 | 11/1994 |
| WO | 9429351 A2 | 12/1994 |
| WO | 9633735 A1 | 10/1996 |
| WO | 9634096 A1 | 10/1996 |
| WO | 9824893 A2 | 6/1998 |
| WO | 03086310 A2 | 10/2003 |
| WO | 2005120571 A2 | 12/2005 |
| WO | 20060057702 A2 | 6/2006 |
| WO | 2007054279 A2 | 5/2007 |
| WO | 2012068360 A1 | 5/2012 |
| WO | 2014093936 A1 | 6/2014 |
| WO | 2014179335 A1 | 11/2014 |
| WO | 2014189805 A1 | 11/2014 |
| WO | 2015185565 A1 | 12/2015 |
| WO | 2016096174 A1 | 6/2016 |
| WO | 2016145102 A1 | 9/2016 |
| WO | 2017027645 A1 | 2/2017 |
| WO | 2017027646 A1 | 2/2017 |
| WO | 2017075477 A1 | 5/2017 |

OTHER PUBLICATIONS

Rudikoff et al(Proc. Natl. Acad. Sci. USA 1982 vol. 79: p. 1979). (Year: 1979).*

Pascalis et al (The Journal of Immunology (2002) 169, 3076-3084) (Year: 2002).*

Casset et al. (2003) BBRC 307, 198-205 (Year: 2003).*

Brown et al (J. Immunol. May 1996; 156(9):3285-3291 (Year: 1996).*

Vajdos et al (J. Mol. Biol., Jul. 5, 2002;320(2); 415-428) (Year: 2002).*

Gala and Morrison, V Region Carbohydrate and Antibody Expression. J Immunol. May 1, 2004;172(9):5489-5494.

Gambus et al., Epitope mapping of a mouse monoclonal anti-MUC2 antibody suggests the existence of an Immunodominant region in the COOH terminus of the MUC2 tandem-repeat sequence. Int J Cancer. Jan. 3, 1995;60(1):146-148.

Geisbert and Jahrling, Differentiation of filoviruses by electron microscopy. Virus Res. Dec. 1995;39(2-3):129-150.

Ghazizadeh et al., Role of cdk4, p16INK4, and Rb Expression in the Prognosis of Bronchioloalveolar Carcinomas. Respiration. Jan.-Feb. 2005;72(1):68-73.

Ghirlando et al., Glycosylation of human IgG-Fc: influences on structure revealed by differential scanning micro-calorimetry. Immunol Lett. May 3, 1999;68(1):47-52.

Ghosh et al., Natalizumab for Active Crohn's Disease. N Engl J Med. Jan. 2, 2003;348(1):24-32.

Gibellini et al., Extracellular HIV-1 Tat Protein Induces the Rapid Ser133 Phosphorylation and Activation of CREB Transcription Factor in Both Jurkat Lymphoblastoid T Cells and Primary Peripheral Blood Mononuclear Cells. J Immunol. Apr. 15, 1998;160(8):3891-3898.

Gilliam et al., A phase II study of G17DT in gastric carcinoma. Eur J Surg Oncol. Jun. 2004;30(5):536-543.

Gish and States, Identification of protein coding regions by database similarity search. Nat Genet. Mar. 1993;3(3):266-272.

Giudicelli et al., IMGT/GENE-DB: a comprehensive database for human and mouse immunoglobulin and T cell receptor genes. Nucleic Acids Res. Jan. 1, 2005;33(Database issue):D256-61-D261.

Gonzalez et al., A comparative sequence analysis to revise the current taxonomy of the family Coronaviridae. Arch Virol. Nov. 2003;148(11):2207-2235.

Good et al., Development and regulation of cell-mediated immune responses to the blood stages of malaria: Implications for vaccine research. Annu Rev Immunol. 2005;23:69-99.

Good et al., The immunological challenge to developing a vaccine to the blood stages of malaria parasites. Immunol Rev. Oct. 2004;201:254-267.

Gorman et al., Reshaping a therapeutic CD4 antibody. Proc Natl Acad Sci U S A. May 15, 1991;88(10):4181-4185.

Griffiths and Duncan, Strategies for selection of antibodies by phage display. Curr Opin Biotechnol. Feb. 1998;9(1):102-108.

Grimm et al., Mouse alpha-fetoprotein-specific DNA-based immunotherapy of hepatocellular carcinoma leads to tumor regression in mice. Gastroenterology. Oct. 2000;119(4):1104-1112.

Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.

(56) References Cited

OTHER PUBLICATIONS

Gueguen et al., An Antigen Recognized by Autologous CTLs on a Human Bladder Carcinoma. J Immunol. Jun. 15, 1998;160(12):6188-6194.
Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.
Guo et al., Therapeutic Cancer Vaccines: Past, Present and Future. Adv Cancer Res. 2013;119:421-475.
Gupta and Siber, adjuvants for human vaccines—current status, problems and future prospects. Vaccine. Oct. 1995;13(14):1263-1276.
Gupta et al., Refolding, purification, and crystallization of apical membrane antigen 1 from Plasmodium falciparum. Protein Expr Purif. May 2005;41(1):186-198.
Haddad et al., Novel antigen identification method for discovery of protective malaria antigens by rapid testing of DNA vaccines encoding exons from the parasite genome. Infect Immun. Mar. 2004;72(3):1594-1602.
Hakansson et al., Establishment and phenotypic characterization of human U937 cells with inducible P210 BCR/ABL expression reveals upregulation of CEACAM1 (CD66a). (2004) Leukemia 18:538-547.
Hamilton et al., Production of Complex Human Glycoproteins in Yeast. Science. Aug. 29, 2003;301(5637):1244-1246.
Hamilton et al., Humanization of Yeast to Produce Complex Terminally Sialylated Glycoproteins. Science. Sep. 8, 2006;313(5792):1441-1443.
Hamilton and Gerngross, Glycosylation engineering in yeast: the advent of fully humanized yeast. Curr Opin Biotechnol. Oct. 2007;18(5):387-392.
Hancock and Armstrong, SIMPLE34: an improved and enhanced implementation for VAX and Sun computers of the Simple algorithm for analysis of clustered repetitive motifs in nucleotide sequences. Comput Appl Biosci. Feb. 1994;10(1):67-70.
Harris et al., The Biological and Therapeutic Importance of Gastrin Gene Expression in Pancreatic Adenocarcinomas. Cancer Res. Aug. 15, 2004;64(16):5624-5631.
Hashido et al., Evaluation of an enzyme-linked immunosorbent assay based on binding inhibition for type-specific quantification of poliovirus neutralization-relevant antibodies. Microbiol Immunol. 1999;43(1):73-77.
Hassan et al., Mesothelin: A New Target for Immunotherapy. Clin Cancer Res. Jun. 15, 2004;10(12 Pt 1):3937-3942.
Havlasova et al., Mapping of immunoreactive antigens of Francisella tularensis live vaccine strain. Proteomics. Jul. 2002;2(7):857-867.
Havlasova et al., Proteomic analysis of anti-Francisella tularensis LVS antibody response in murine model of tularemia. Proteomics. May 2005;5(8):2090-2103.
He et al., Humanization and Pharmacokinetics of a Monoclonal Antibody with Specificity for Both E- and P-Selectin. J mmunol. Jan. 15, 1998;160(2):1029-1035.
He et al., Complexes of Poliovirus Serotypes with Their Common Cellular Receptor, CD155. J Virol. Apr. 2003;77(8):4827-4835.
Henikoff and Henikoff, Amino acid substitution matrices from protein blocks. Proc Natl Acad Sci U S A. Nov. 15, 1992;89(22):10915-10919.
Herold et al., Anti-CD3 monoclonal antibody in new-onset type 1 diabetes mellitus. N Engl J Med. May 30, 2002;346(22):1692-1698.
Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. Jan. 2005;81(1):48-57.
Hoffman et al., Strategy for development of a pre-erythrocytic Plasmodium falciparum DNA vaccine for human use. Vaccine. Jun. 1997;15(8):842-845.
Hoke, History of U.S. Military Contributions to the Study of Viral Encephalitis. Mil Med. Apr. 2005;170(4 Suppl):92-105.

Holliger and Hudson, Engineered antibody fragments and the rise of single domains. Nat Biotechnol. Sep. 2005;23(9):1126-1136.
Holliger et al., "Diabodies": Small bivalent and bispecific antibody fragments. Proc Natl Acad Sci U S A. Jul. 15, 1993;90(14):6444-6448.
Hoogenboom and Chames, Natural and designer binding sites made by phage display technology. Immunol Today. Aug. 2000;21(8):371-378.
Hsing and Bishop, Requirement for Nuclear Factor-κB Activation by a Distinct Subset of CD40-Mediated Effector Functions in B Lymphocytes. J Immunol. Mar. 1, 1999;162(5):2804-2811.
Hudson and Kortt, High avidity scFv multimers; diabodies and triabodies. J Immunol Methods. Dec. 10, 1999;231(1-2):177-189.
Hunter and Greenwood, Preparation of iodine-131 labelled human growth hormone of high specific activity. Nature. May 5, 1962;194:495-496.
Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.
Hutchinson et al., Multiplex Analysis of Cytokines in the Blood of Cynomolgus Macaques Naturally Infected With Ebola Virus (Reston Serotype). J Med Virol. Nov. 2001;65(3):561-566.
Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.
Inouye and Inouye, Up-Promoter Mutations in the Lpp Gene of *Escherichia coli*. Nucleic Acids Res. May 10, 1985;13(9):3101-3110.
Abutaily et al., Cadherins, catenins and APC in pleural malignant mesothelioma. J Pathol. Nov. 2003;201(3):355-362.
Aguilar et al., Endemic Venezuelan Equine Encephalitis in Northern Peru. Emerg Infect Dis. May 2004;10(5):880-888.
Ahn et al., All CVB Serotypes and Clinical Isolates Induce Irreversible Cytopathic Effects in Primary Cardiomyocytes. J Med Virol. Feb. 2005;75(2):290-294.
Alexander and Hughes, Monitoring of IgG Antibody Thermal Stability by Micellar Electrokinetic Capillary Chromatography and Matrix-Assisted Laser Desorption/Ionization Mass Spectrometry. Anal Chem. Oct. 15, 1995;67(20):3626-3632.
Altschul et al., Protein database searches using compositionally adjusted substitution matrices. FEBS J. Oct. 2005;272(20):5101-5109.
Altschul, Evaluating the statistical significance of multiple distinct local alignments. In Theoretical and Computational Methods in Genome Research (S. Suhai, ed.), 1997:1-14.
Altschul, Amino Acid Substitution Matrices from an Information Theoretic Perspective. J Mol Biol. Jun. 5, 1991;219(3):555-565.
Altschul et al., Basic Local Alignment Search Tool. J Mol Biol. Oct. 5, 1990;215(3):403-410.
Altschul, A Protein Alignment Scoring System Sensitive at All Evolutionary Distances. J Mol Evol. Mar. 1993;36(3):290-300.
Altschul et al., Gapped BLAST and PSI-BLAST: a new generation of protein database search programs. Nucleic Acids Res. Sep. 1, 1997;25(17):3389-3402.
Altwein and Luboldt, Prognostic factors for carcinoma of the prostate. Urol Int. 1999;63(1):62-71.
Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.
Andersen and thor Straten, Survivin—a universal tumor antigen. Histol Histopathol. Apr. 2002;17(2):669-675.
Angal et al., A single amino acid substitution abolishes the heterogeneity of chimeric mouse/human (IgG4) antibody. Mol Immunol. Jan. 1993;30(1):105-108.
Argani et al., Discovery of New Markers of Cancer through Serial Analysis of Gene Expression: Prostate Stem Cell Antigen Is Overexpressed in Pancreatic Adenocarcinoma. Cancer Res. Jun. 1, 2001;61(11):4320-4324.

(56) References Cited

OTHER PUBLICATIONS

Arora et al., Identification of Differentially Expressed Genes in Oral Squamous Cell Carcinoma. Mol Carcinog. Feb. 2005;42(2):97-108.
Attoui et al., Comparative sequence analysis of American, European and Asian isolates of viruses in the genus Coltivirus. J Gen Virol. Oct. 1998;79 ( Pt 10):2481-2489.
Azzoni et al., Differential Transcriptional Regulation of CD161 and a Novel Gene, 197/15a, by IL-2, IL-15, and IL-12 in NK and T Cells. J Immunol. Oct. 1, 1998;161(7):3493-3500.
Baca et al., Antibody Humanization Using Monovalent Phage Display. J Biol Chem. Apr. 18, 1997;272(16):10678-10684.
Baert et al., Influence of Immunogenicity on the Long-Term Efficacy of Infliximab in Crohn's Disease. N Engl J Med. Feb. 13, 2003;348(7):601-608.
Baldridge and Crane, Monophosphoryl Lipid A (MPL) Formulations for the Next Generation of Vaccines. Methods. Sep. 1999;19(1):103-107.
Barbanti-Brodano et al., Simian virus 40 infection in humans and association with human diseases: results and hypotheses. Virology. Jan. 5, 2004;318(1):1-9.
Barbas, Synthetic human antibodies. Nat Med. Aug. 1995;1(8):837-839.
Barthold et al., Infectivity, Disease Patterns, and Serologic Profiles of Reovirus Serotypes 1, 2, and 3 in Infant and Weanling Mice. Lab Anim Sci. Oct. 1993;43(5):425-430.
Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Bebbington and Hentschel, "The Use of Vectors Based on Gene Amplification for the Expression of Cloned Genes in Mammalian Cells," in DNA Cloning, vol. 3. (Academic Press, New York), 1987:163-188.
Beniaminovitz et al., Prevention of Rejection in Cardiac Transplantation by Blockade of the Interleukin-2 Receptor with a Monoclonal Antibody. N Engl J Med. Mar. 2, 2000;342(9):613-619.
Benson et al., GenBank. Nucleic Acids Res. Jan. 2013;41(D1):D36-42.
Bevanger et al., Competitive enzyme immunoassay for antibodies to a 43,000-molecular-weight Francisella tularensis outer membrane protein for the diagnosis of tularemia. J Clin Microbiol. May 1989;27(5):922-926.
Bhigjee et al., Sequence of the env gene of some KwaZulu-Natal, South African strains of HTLV type I. AIDS Res Hum Retroviruses. Sep. 1, 1999;15(13):1229-1233.
Biagini et al., Simultaneous measurement of specific serum IgG responses to five select agents. Anal Bioanal Chem. Jun. 2005;382(4):1027-1034.
Bieg et al., GAD65 and Insulin B Chain Peptide (9-23) Are Not Primary Autoantigens in the Type 1 Diabetes Syndrome of the BB Rat. Autoimmunity. 1999;31(1):15-24.
Bischoff and Kolbe, Deamidation of asparagine and glutamine residues in proteins and peptides: structural determinants and analytical methodology. J Chromatogr B Biomed Appl. Dec. 9, 1994;662(2):261-278.
Bitter et al., Expression and Secretion Vectors for Yeast. Methods Enzymol. 1987;153:516-544.
Bondurant et al., Definition of an Immunogenic RegionWithin the OvarianTumor Antigen Stratum Corneum Chymotryptic Enzyme. Clin Cancer Res. May 1, 2005;11(9):3446-3454.
Brennan et al., Preparation of Bispecific Antibodies by Chemical Recombination of Monoclonal Immunoglobulin G1 Fragments. Science. Jul. 5, 1985;229(4708):81-83.
Brezniceanu et al., HMGB1 inhibits cell death in yeast and mammalian cells and is abundantly expressed in human breast carcinoma. FASEB J. Jul. 2003;17(10):1295-1297.
Brian and Baric, Coronavirus Genome Structure and Replication. Curr Top Microbiol Immunol. 2005;287:1-30.
Brinkmann et al., Novel Genes in the PAGE and GAGE Family of Tumor Antigens Found by Homology Walking in be dbEST Database. Cancer Res. Apr. 1, 1999;59(7):1445-1448.

Bronte et al., Genetic Vaccination with "Self" Tyrosinase-related Protein 2 Causes Melanoma Eradication but not Vitiligo. Cancer Res. Jan. 15, 2000;60(2):253-258.
Brown, Variants of B19. Dev Biol (Basel). 2004;118:71-77.
Brown et al., Complete Genomic Sequencing Shows that Polioviruses and Members of Human Enterovirus Species C Are Closely Related in the Noncapsid Coding Region. J Virol. Aug. 2003;77(16):8973-8984.
Bruggemann and Taussig, Production of human antibody repertoires in transgenic mice. Curr Opin Biotechnol. Aug. 1997;8(4):455-458.
Capdepont et al., New Insights in HTLV-I Phylogeny by Sequencing and Analyzing the Entire Envelope Gene. AIDS Res Hum Retroviruses. Jan. 2005;21(1):28-42.
Capurro et al., Glypican-3: A Novel Serum and Histochemical Marker for Hepatocellular Carcinoma. Gastroenterology. Jul. 2003;125(1):89-97.
Carbone et al., New developments about the association of SV40 with human mesothelioma. Oncogene. Aug. 11, 2003;22(33):5173-5180.
Carpenter et al., Non-Fc Receptor-Binding Humanized Anti-CD3 Antibodies Induce Apoptosis of Activated Human T Cells. J Immunol. Dec. 1, 2000;165(11):6205-6213.
Carter, Bispecific human IgG by design. J Immunol Methods. Feb. 1, 2001;248(1-2):7-15.
Carter et al., Humanization of an anti-p185HER2 antibody for human cancer therapy. Proc Natl Acad Sci U S A. May 15, 1992;89(10):4285-4289.
Chan et al., In Situ Hybridization Study of PSP94 (Prostatic Secretory Protein of 94 Amino Acids) Expression in Human Prostates. Prostate. Oct. 1, 1999;41(2):99-109.
Pluckthun, Antibodies from *Escherichia coli*. in the Pharmacology of Monoclonal Antibodies, Rosenburg and Moore eds. Springer-Verlag, New York, 1994;113:269-315 (part 1).
Pluckthun, Antibodies from *Escherichia coli*. in the Pharmacology of Monoclonal Antibodies, Rosenburg and Moore eds. Springer-Verlag, New York, 1994;113:269-315 (part 2).
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.
Portielji et al., IL-12: a promising adjuvant for cancer vaccination. Cancer Immunol Immunother. Mar. 2003;52(3):133-144.
Presta, Selection, design, and engineering of therapeutic antibodies. J Allergy Clin Immunol. Oct. 2005;116(4):731-736.
Presta et al., Humanization of an Anti-Vascular Endothelial Growth Factor Monoclonal Antibody for the Therapy of Solid Tumors and Other Disorders. Cancer Res. Oct. 15, 1997;57(20):4593-4599.
Propst et al., Proinflammatory and Th2-Derived Cytokines Modulate CD40-Mediated Expression of Inflammatory Mediators in Airway Epithelia: Implications for the Role of Epithelial CD40 in Airway Inflammation. J Immunol. Aug. 15, 2000;165(4):2214-2221.
Proudfoot, Transcriptional interference and termination between duplicated alpha-globin gene constructs suggests a novel mechanism for gene regulation. Nature. Aug. 7-13, 1986;322(6079):562-565.
Queen et al., A humanized antibody that binds to the interleukin 2 receptor. Proc Natl Acad Sci U S A. Dec. 1989;86(24):10029-10033.
Rader et al., A phage display approach for rapid antibody humanization: Designed combinatorial V gene libraries. Proc Natl Acad Sci U S A. Jul. 21, 1998;95(15):8910-8915.
Raghunathan et al., Antigen-binding site anatomy and somatic mutations in antibodies that recognize different types of antigens. J Mol Recognit. Mar. 2012;25(3):103-113—incl supplemental data (25 pages total).
Raso et al., Intracellular Targeting with Low pH-triggered Bispecific Antibodies. J Biol Chem. Oct. 31, 1997;272(44):27623-27628.
Reichmann and Muyldermans, Single domain antibodies: Comparison of camel VH and camelised human VH domains. J Immunol Methods. Dec. 10, 1999;231(1-2):25-38.

(56) References Cited

OTHER PUBLICATIONS

Reissner and Aswad, Deamidation and isoaspartate formation in proteins: unwanted alterations or surreptitious signals? Cell Mol Life Sci. Jul. 2003;60(7):1281-1295.
Renkvist et al., A listing of human tumor antigens recognized by T cells. Cancer Immunol Immunother. Mar. 2001;50(1):3-15.
Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Rezig et al., Molecular Characterization of Coxsackievirus B5 Isolates. J Med Virol. Feb. 2004;72(2):268-274.
Riechmann et al., Reshaping human antibodies for therapy. Nature. Mar. 24, 1988;332(6162):323-327.
Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.
Roden and Wu, Preventative and therapeutic vaccines for cervical cancer. Expert Rev Vaccines. Aug. 2003;2(4):495-516.
Roguska et al., Humanization of murine monoclonal antibodies through variable domain resurfacing. Proc Natl Acad Sci U S A. Feb. 1, 1994;91(3):969-973.
Roner et al., Identification of signals required for the insertion of heterologous genome segments into the reovirus genome. Proc Natl Acad Sci U S A. Dec. 19, 1995;92(26):12362-12366.
Rosok et al., A Combinatorial Library Strategy for the Rapid Humanization of Anticarcinoma BR96 Fab. J Biol Chem. Sep. 13, 1996;271(37):22611-22618.
Rossi et al., A Comparative Study Between a Novel Category of Immunoreagents and the Corresponding Mouse Monoclonal Antibodies. Am J Clin Pathol. Aug. 2005;124(2):295-302.
Ruther and Müller-Hill, Easy identification of cDNA clones. EMBO J. 1983;2(10):1791-1794.
Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma cells. Cancer Res. Oct. 1, 1997;57(19):4348-4355.
Santerre et al Expression of prokaryotic genes for hygromycin B and G418 resistance as dominant-selection markers in mouse L cells. Gene. Oct. 1984;30(1-3):147-156.
Santin et al., The serine protease stratum corneum chymotryptic enzyme (kallikrein 7) is highly overexpressed in squamous cervical cancer cells. Gynecol Oncol. Aug. 2004;94(2):283-288.
Sarcevic et al., Expression of Cancer/Testis Tumor Associated Antigens in Cervical Squamous Cell Carcinoma. Oncology. 2003;64(4):443-449.
Sarobe et al., Carcinoembryonic Antigen as a Target to Induce Anti-Tumor Immune Responses. Curr Cancer Drug Targets. Aug. 2004;4(5):443-454.
Sasaki et al., Sage mRNA expression in advanced-stage lung cancers. Eur J Surg Oncol. Dec. 2003;29(10):900-903.
Sasatomi et al., Expression of tumor rejection antigens in colorectal carcinomas. Cancer. Mar. 15, 2002;94(6):1636-1641.
Scanlan et al., Antigens recognized by autologous antibody in patients with renal-cell carcinoma. Int J Cancer. Nov. 12, 1999;83(4):456-464.
Scanlan et al., Expression of cancer-testis antigens in lung cancer: definition of bromodomain testis-specific gene (BRDT) as a new CT gene, CT9. Cancer Lett. Mar. 31, 2000;150(2):155-164.
Scanlan et al., Humoral immunity to human breast cancer: antigen definition and quantitative analysis of mRNA expression. Cancer Immun. Mar. 30, 2001;1:4.
Scanlan et al., Cancer-related serological recognition of human colon cancer: identification of potential diagnostic and immunotherapeutic targets. Cancer Res. Jul. 15, 2002;62(14):4041-4047.
Scanlan et al., The cancer/testis genes: review, standardization, and commentary. Cancer Immun. Jan. 23, 2004;4:1.
Scarcella et al., Expression of MAGE and GAGE in high-grade brain tumors: a potential target for specific immunotherapy and diagnostic markers. Clin Cancer Res. Feb. 1999;5(2):335-341.
Schmittgen et al., Expression of prostate specific membrane antigen and three alternatively spliced variants of PSMA in prostate cancer patients. Int J Cancer. Nov. 1, 2003;107(2):323-329.
Schwartz et al., Novel targeted and immunotherapeutic strategies in chronic myeloid leukemia. Semin Hematol. Jan. 2003;40(1):87-96.
Scott and Smith, Searching for Peptide Ligands with an Epitope Library. Science. Jul. 27, 1990;249(4967):386-388.
Segal et al., Introduction: bispecific antibodies. J Immunol Methods. Feb. 1, 2001;248(1-2):1-6.
Sepehr et al., Distinct pattern of TP53 mutations in squamous cell carcinoma of the esophagus in Iran. Oncogene. Nov. 1, 2001;20(50):7368-7374.
Shields et al., High Resolution Mapping of the Binding Site on Human IgG1 for FcγRl, FcγRll, FcγRlll, and FcRn and Design of IgG1 Variants with Improved Binding to the FcγR R. J Biol Chem. Mar. 2, 2001;276(9):6591-6604.
Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.
Shinkawa et al., The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity. J Biol Chem. Jan. 31, 2003;278(5):3466-3473.
Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.
Shirasawa et al., Receptor for advanced glycation end-products is a marker of type I lung alveolar cells. Genes Cells. Feb. 2004;9(2):165-174.
Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.
Siegel et al., Induction of antitumour immunity using survivin peptide-pulsed dendritic cells in a murine lymphoma model. Br J Haematol. Sep. 2003;122(6):911-914.
Chang et al., A Phase I Trial of Tumor Lysate-Pulsed Dendritic Cells in the Treatment of Advanced Cancer. Clin Cancer Res. Apr. 2002;8(4):1021-1032.
Chen et al., Influence of Histidine on the Stability and Physical Properties of a Fully Human Antibody in Aqueous and Solid Forms. Pharm Res. Dec. 2003;20(12):1952-1960.
Chen et al., Immunodominant CD4+ responses identified in a patient vaccinated with full-length NY-ESO-1 formulated with ISCOMATRIX adjuvant. Proc Natl Acad Sci U S A. Jun. 22, 2004;101(25):9363-9368.
Chern et al., Glycoprotein B Subtyping of Cytomegalovirus (CMV) in the Vitreous of Patients with AIDS and CMV Retinitis. J Infect Dis. Oct. 1998;178(4):1149-1153.
Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.
Choi et al., Use of combinatorial genetic libraries to humanize N-linked glycosylation in the yeast *Pichia pastoris*. Proc Natl Acad Sci U S A. Apr. 29, 2003;100(9):5022-5027 (incl correction page for 7 pages total).
Chothia and Lesk, Canonical Structures for the Hypervariable Regions of Immunoglobulins. J Mol Biol. Aug. 20, 1987;196(4):901-917.
Chothia et al., Conformations of immunoglobulin hypervariable regions. Nature. Dec. 21-28, 1989;342(6252):877-883.
Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.

(56) References Cited

OTHER PUBLICATIONS

Clements et al., Adenomatous Polyposis Coli/ß-Catenin Interaction and Downstream Targets: Altered Gene Expression in Gastrointestinal Tumors. Clin Colorectal Cancer. Aug. 2003;3(2):113-120.
Clifton et al., A chlamydial type III translocated protein is tyrosine-phosphorylated at the site of entry and associated with recruitment of actin. Proc Natl Acad Sci USA. Jul. 6, 2004;101(27):10166-10171.
Clinton et al., A Comparative Study of Four Serological Tumor Markers for the Detection of Breast Cancer. Biomed Sci Instrum. 2003;39:408-414.
Cobaleda et al., A primitive hematopoietic cell is the target for the leukemic transformation in human Philadelphia-positive acute lymphoblastic leukemia. Blood. Feb. 1, 2000;95(3):1007-1013.
Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.
Colbere-Garapin et al., A New Dominant Hybrid Selective Marker for Higher Eukaryotic Cells. J Mol Biol. Jul. 25, 1981;150(1):1-14.
Conrath et al., Camel Single-domain Antibodies as Modular Building Units in Bispecific and Bivalent Antibody Constructs. J Biol Chem. Mar. 9, 2001;276(10):7346-7350.
Crouse et al., Expression and Amplification of Engineered Mouse Dihydrofolate Reductase Minigenes, Mol Cell Biol. Feb. 1983;3(2):257-266.
Cwirla et al., Peptides on phage: A vast library of peptides for identifying ligands. Proc Natl Acad Sci U S A. Aug. 1990;87(16):6378-6382.
Dalerba et al., MAGE, BAGE and GAGE gene expression in human rhabdomyosarcomas. Int J Cancer. Jul. 1, 2001;93(1):85-90.
Damasus-Awatai and Freeman-Wang, Human papilloma virus and cervical screening. Curr Opin Obstet Gynecol. Dec. 2003;15(6):473-477.
Das et al., Evaluation of a Western Equine Encephalitis recombinant E1 protein for protective immunity and diagnostics. Antiviral Res. Nov. 2004;64(2):85-92.
David and Reisfeld, Protein Iodination with Solid State Lactoperoxidase. Biochemistry. Feb. 26, 1974;13(5):1014-1021.
Davies et al., Characterisation of a recombinant Fv fragment of anti-MUC1 antibody HMFG1. Cancer Lett. Jul. 29, 1994;82(2):179-184.
Dayhoff et al., A Model of Evolutionary Change in Proteins. Atlas of Protein Sequence and Structure, M.O. Dayhoff (ed.), 1978; 5(suppl. 3): 345-352.
De Backer et al., Characterization of the GAGE Genes That Are Expressed in Various Human Cancers and in Normal Testis. Cancer Res. Jul. 1, 1999;59(13):3157-3165.
de Bruin et al., Selection of high-affinity phage antibodies from phage display libraries. Nat Biotechnol. Apr. 1999;17(4):397-399.
de Jong et al., A Novel Platform for the Potentiation of Therapeutic Antibodies Based on Antigen-Dependent Formation of IgG Hexamers at the Cell Surface. PLoS Biol. Jan. 6, 2016;14(1):e1002344.
De Pascalis et al., Grafting of "Abbreviated" Complementarity-Determining Regions Containing Specificity-Determining Residues Essential for Ligand Contact to Engineer a Less Immunogenic Humanized Monoclonal Antibody. J lmmunol. Sep. 15, 2002;169(6):3076-3084.
de Villiers et al., Classification of papillomaviruses. Virology. Jun. 20, 2004;324(1):17-24.
Dembo et al., Limit distribution of Maximal Non-Aligned Two-Sequence Segmental Score. Ann Prob. 1994;22:2022-2039 (pp. 1-16).
Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.
Desmyter et al., Antigen Specificity and High Affinity Binding Provided by One Single Loop of a Camel Single-domain Antibody. J Biol Chem. Jul. 13, 2001;276(28):26285-26290.

Devlin et al., Random Peptide Libraries: A Source of Specific Protein Binding Molecules. Science. Jul. 27, 1990;249(4967):404-406.
Disis and Cheever, HER-2/Neu Protein: A Target for Antigen-Specific Immunotherapy of Human Cancer. Adv Cancer Res. 1997;71:343-371.
Disis et al., Humoral Epitope-Spreading Following Immunization with a HER-2/neu Peptide Based Vaccine in Cancer Patients. J Clin Immunol. Sep. 2004;24(5):571-578.
Dosaka-Akita et al., Expression of N-Acetylglucosaminyltransferase V Is Associated with Prognosis and Histology in Non-Small Cell Lung Cancers. Clin Cancer Res. Mar. 1, 2004;10(5):1773-1779.
Duxbury et al., CEACAM6 as a novel target for indirect type 1 immunotoxin-based therapy in pancreatic adenocarcinoma. Biochem Biophys Res Commun. May 7, 2004;317(3):837-843.
Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997;35(5):1122-1130.
Engels et al., Serologic Evidence for Exposure to Simian Virus 40 in North American Zoo Workers. J Infect Dis. Dec. 15, 2004;190(12):2065-2069.
Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.
Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.
Estrada-Franco et al., Venezuelan Equine Encephalitis Virus, Southern Mexico. Emerg Infect Dis. Dec. 2004; (12):2113-2121.
Everts et al., Selective Intracellular Delivery of Dexamethasone into Activated Endothelial Cells Using an E-Selectin-Directed Immunoconjugate. J Immunol. Jan. 15, 2002;168(2):883-889.
Fang et al., Expression of Dnmt1, demethylase, MeCP2 and methylation of tumor-related genes in human gastric cancer. World J Gastroenterol. Dec. 1, 2004;10(23):3394-3398.
Faure et al., Inducible Hsp70 as Target of Anticancer Immunotherapy: Identification of HLA-A*0201-Restricted Epitopes. Int J Cancer. Mar. 1, 2004;108(6):863-870.
Fleishhauer et al., The DAM Gene Family Encodes a New Group of Tumor-specific Antigens Recognized by Human Leukocyte Antigen Al-restricted Cytotoxic T Lymphocytes. Cancer Res. Jul. 15, 1998;58(14):2969-2972.
Fong et al., Altered peptide ligand vaccination with Flt3 ligand expanded dendritic cells for tumor immunotherapy. Proc Natl Acad Sci U S A. Jul. 17, 2001;98(15):8809-8814.
Foote and Winter, Antibody framework residues affecting the conformation of the hypervariable loops. J Mol Biol. Mar. 20, 1992;224(2):487-499.
Frankle et al., Neuroreceptor imaging in psychiatry: theory and applications. Int Rev Neurobiol. 2005;67:385-440.
Fuessel et al., Multiple tumor marker analyses (PSA, hK2, PSCA, trp-p8) in primary prostate cancers using quantitative RT-PCR. Int J Oncol. Jul. 2003;23(1):221-228.
Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.
Wallick et al., Glycosylation of a VH residue of a monoclonal antibody against alpha (1—6) dextran increases its affinity for antigen. J Exp Med. Sep. 1, 1988;168(3):1099-1109.
Waltregny et al., Screening of histone deacetylases (HDAC) expression in human prostate cancer reveals distinct class I HDAC profiles between epithelial and stromal cells. Eur J Histochern. Jul.-Sep. 2004;48(3):273-290.
Wang et al., Identification of a Novel Major Histocompatibility Complex Class II—restricted Tumor Antigen Resulting from a Chromosomal Rearrangement Recognized by CD4+ T Cells. J Exp Med. May 17, 1999;189(10):1659-1668.

(56) References Cited

OTHER PUBLICATIONS

Wang et al., Cloning Genes Encoding MHC Class II—Restricted Antigens: Mutated CDC27 as a Tumor Antigen. Science. May 21, 1999;284(5418):1351-1354.

Wang et al., Alterations of APC, c-met, and p53 Genes in Tumor Tissue and Serum of Patients with Gastric Cancers. J Surg Res. Aug. 2004;120(2):242-248.

Ward et al., Binding activities of a repertoire of single immunoglobulin variable domains secreted from *Escherichia coli*. Nature. Oct. 12, 1989;341(6242):544-546.

Weaver et al., Venezuelan Equine Encephalitis. Annu Rev Entomol. 2004;49:141-174.

Weaver et al., Genetic determinants of Venezuelan equine encephalitis emergence. Arch Virol Suppl. 2004; (18):43-64.

Wells et al., Swine Influenza Virus Infections Transmission. From III Pigs to Humans at a Wisconsin Agricultural Fair and Subsequent Probable Person-to-Person Transmission. JAMA. Jan. 23-30, 1991;265(4):478-481.

Wen et al., Poly(ethylene glycol)-Conjugated Anti-EGF Receptor Antibody C225 with Radiometal Chelator Attached to the Termini of Polymer Chains. Bioconjug Chem. Jul.-Aug. 2001;12(4):545-553.

Wentworth et al., An Influenza A (HINI) Virus, Closely Related to Swine Influenza Virus, Responsible for a Fatal Case of Human Influenza. J Virol. Apr. 1994;68(4):2051-2058.

Wigler et al., Transfer of Purified Herpes Virus Thymidine Kinase Gene to Cultured Mouse Cells. Cell. May 1977;11(1):223-232.

Wigler et al., Transformation of mammalian cells with an amplifiable dominant-acting gene. Proc Natl Acad Sci U S A. Jun. 1980;77(6):3567-3570.

Wilson et al., Simplified conjugation chemistry for coupling peptides to F(ab') fragments: autologous red cell agglutination assay for HIV-1 antibodies. J Immunol Methods. Oct. 14, 1994;175(2):267-273.

Wootton and Federhen, Statistics of local complexity in amino acid sequences and sequence databases. Comput Chem. 1993;17(2):149-163.

Wren et al., Signal-Sequence Information and GeNomic AnaLysis. Comput Methods Programs Biomed. May 2002;68(2):177-181.

Wright et al., Lymphoid/Neuronal Cell Surface OX2 Glycoprotein Recognizes a Novel Receptor on Macrophages Implicated in the Control of Their Function. Immunity. Aug. 2000;13(2):233-242.

Wu et al., Humanization of a Murine Monoclonal Antibody by Simultaneous Optimization of Framework and CDR Residues. J Mol Biol. Nov. 19, 1999;294(1):151-162.

Yamazaki et al., Cutting Edge: Tumor Secreted Heat Shock-Fusion Protein Elicits CD8 Cells for Rejection. J Immunol. Nov. 15, 1999;163(10):5178-5182.

Yan et al., Synthesis and immunostimulatory properties of the phosphorothioate analogues of cdiGMP. Bioorg Med Chem Lett. Oct. 15, 2008;18(20):5631-5634.

Yang, et al., A Randomized Trial of Bevacizumab, an Anti—Vascular Endothelial Growth Factor Antibody, for Metastatic Renal Cancer. N Engl J Med. Jul. 31, 2003;349(5):427-434.

Yarmush et al., Coupling of antibody-binding fragments to solid-phase supports: site-directed binding of F(ab')2 fragments. J Biochem Biophys Methods. Dec. 1992;25(4):285-297.

Ye et al., IgBLAST: an immunoglobulin variable domain sequence analysis tool. Nucleic Acids Res. Jul. 2013;41(Web Server issue):W34-40.

Zaremba et al., Identification of an Enhancer Agonist Cytotoxic T Lymphocyte Peptide from Human Carcinoembryonic Antigen. Cancer Res. Oct. 15, 1997;57(20):4570-4577.

Zeier et al., New Ecological Aspects of Hantavirus Infection: A Change of a Paradigm and a Challenge of Prevention—A Review. Virus Genes. Mar. 2005;30(2):157-180.

Zhang and Madden, PowerBLAST: A New Network BLAST Application for Interactive or Automated Sequence Analysis and Annotation. Genome Res. Jun. 1997;7(6):649-656.

Zheng et al., Expression of the Platelet Receptor GPVI Confers Signaling via the Fc Receptor γ-Chain in Response to the Snake Venom Convulxin but Not to Collagen. J Biol Chem. Apr. 20, 2001;276(16):12999-13006.

Zimmerman et al., Expression of annexin II in conventional renal cell carcinoma is correlated with Fuhrman grade and clinical outcome. Virchows Arch. Oct. 2004;445(4):368-374.

Ziyaeyan et al., The Seroprevalence of Parvovirus BI9 Infection among To-Be-Married Girls, Pregnant Women, and Their Neonates in Shiraz, Iran. Jpn J Infect Dis. Apr. 2005;58(2):95-97.

Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.

Isherwood et al., Vaccination strategies for Francisella tularensis. Adv Drug Deliv Rev. Jun. 17, 2005;57(9):1403-1414.

Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2):242-250.

Jainkittivong and Langlais, Herpes B virus infection. Oral Surg Oral Med Oral Pathol Oral Radiol Endod. Apr. 1998;85(4):399-403.

Jamieson et al., Human Torovirus: A New Nosocomial Gastrointestinal Pathogen. J Infect Dis. Nov. 1998;178(5):1263-1269.

Jansen and Shaw, Human Papillomavirus Vaccines and Prevention of Cervical Cancer. Annu Rev Med. 2004;55:319-331.

Johnson et al., 3-O-Desacyl Monophosphoryl Lipid a Derivatives: Synthesis and Immunostimulant Activities. J Med Chem. Nov. 4, 1999;42(22):4640-4649.

Jones et al., Replacing the complementarity-determining regions in a human antibody with those from a mouse. Nature. May 29-Jun. 4, 1986;321(6069):522-525.

Jung et al., Strategies Against Human Papillomavirus Infection and Cervical Cancer. J Microbiol. Dec. 2004;42(4):255-266.

Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.

Kabat, The Structural Basis of Antibody Complementarity. Adv Protein Chem. 1978;32:1-75.

Kabat et al., Unusual Distributions of Amino Acids in Complementarity determining (Hypervariable) Segments of Heavy and Light Chains of Immunoglobulins and Their Possible Roles in Specificity of Antibody-combining Sites. J Biol Chem. Oct. 10, 1977;252(19):6609-6616.

Kaithamana et al., Induction of Experimental Autoimmune Graves' Disease in BALB/c Mice. J Immunol. Nov. 1, 1999;163(9):5157-5164.

Krlin and Altschul, Methods for assessing the statistical significance of molecular sequence features by using general scoring schemes. Proc Natl Acad Sci U S A. Mar. 1990;87(6):2264-2268.

Karlin and Altschul, Applications and statistics for multiple high-scoring segments in molecular sequences. Proc Natl Acad Sci USA Jun. 15, 1993;90(12):5873-5877.

Kaufman et al., Parvovirus B19 does not bind to membrane-associated globoside in vitro. Virology. Feb. 5, 2005;332(1):189-198.

Kedl et al., Comparative Sequence Analysis of the Reovirus S4 Genes from 13 Serotype 1 and Serotype 3 Field Isolates. J Virol. Jan. 1995;69(1):552-559.

Kim et al., Comparison of HPV DNA vaccines employing intracellular targeting strategies. Gene Ther. Jun. 2004;11(12):1011-1018.

Kita et al., Does IgE Bind to and Activate Eosinophils from Patients with Allergy? J Immunol. Jun. 1, 1999;162(11):6901-6911.

Kohler, Immunoglobulin chain loss in hybridoma lines. Proc Natl Acad Sci U S A. Apr. 1980;77(4):2197-2199.

Krauss et al., Specificity grafting of human antibody frameworks selected from a phage display library: generation of a highly stable humanized anti-CD22 single-chain Fv fragment. Protein Eng. Oct. 2003;16(10):753-759.

Krishnamurthy and Manning, The Stability Factor: Importance in Formulation Development. Curr Pharm Thotechnol. Dec. 2002;3(4):361-371.

(56) References Cited

OTHER PUBLICATIONS

Krzych et al., T lymphocytes from volunteers immunized with irradiated Plasmodium falciparum sporozoites recognize liver and blood stage malaria antigens. J Immunol. Oct. 15, 1995;155(8):4072-4077.

Kubuschok et al., Expression of cancer testis antigens in pancreatic carcinoma cell lines, pancreatic adenocarcinoma and chronic pancreatitis. Int J Cancer Apr. 20, 2004;109(4):568-575.

Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.

Labrijn et al., Efficient generation of stable bispecific IgG1 by controlled Fab-arm exchange. Proc Natl Acad Sci U S A. Mar. 26, 2013;110(13):5145-5150.

Laheru and Jaffee, Immunotherapy for pancreatic cancer—science driving clinical progress. Nat Rev Cancer Jun. 2005;5(6):459-467.

Le Doussal et al., Enhanced in vivo targeting of an asymmetric bivalent hapten to double-antigen-positive mouse B cells with monoclonal antibody conjugate cocktails. J Immunol. Jan. 1, 1991;146(1):169-175.

Lee et al., Immunomic analysis of human sarcoma. Proc Natl Acad Sci U S A. Mar. 4, 2003;100(5):2651-2656.

Lee et al., Prolonged Circulating Lives of Single-Chain Fv Proteins Conjugated with Polyethylene Glycol: A comparison of Conjugation Chemistries and Compounds. Bioconjug Chem. Nov.-Dec. 1999;10(6):973-981.

Lefranc et al., IMGT, the international ImMunoGeneTics database. Nucleic Acids Res. Jan. 1, 1999;27(1):209-212.

Li et al., Optimization of humanized IgGs in glycoengineered Pichia pastoris. Nat Biotechnol. Feb. 2006;24(2):210-215.

Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.

Li et al., Expression Profile of Cancer-Testis Genes in 121 Human Colorectal Cancer Tissue and Adjacent Normal Tissue. Clin Cancer Res. Mar. 1, 2005;11(5):1809-1814.

Liang et al., Microvessel density, cyclo-oxygenase 2 expression, K-ras mutation and p53 overexpression in colonic cancer. Br J Surg. Mar. 2004;91(3):355-361.

Lim et al., Molecular and phenotypic spectrum of de novo Philadelphia positive acute leukemia. Int J Mol Med. Dec. 1999;4(6):665-667.

Lin et al., Melanoma-Associated Antigens in Esophageal Adenocarcinoma Identification of Novel MAGE-A10 Splice Variants. Clin Cancer Res. Sep. 1, 2004;10(17):5708-5716.

Lipsky, et al., Infliximab and methotrexate in the treatment of rheumatoid arthritis. Anti-Tumor Necrosis Factor Trial in Rheumatoid Arthritis with Concomitant Therapy Study Group. N Engl J Med. Nov. 30, 2000;343(22):1594-1602.

Liu and Blumhardt, Randomised, double blind, placebo controlled study of interferon β-1a in relapsing-remitting multiple sclerosis analysed by area under disability/time curves. J Neurol Neurosurg Psychiatry. Oct. 1999;67(4):451-456.

Lodmell et al., DNA vaccination of mice against rabies virus: effects of the route of vaccination and the adjuvant monophosphoryl lipid a (MPL). Vaccine. Jan. 6, 2000;18(11-12):1059-1066.

Logan and Shenk, Adenovirus tripartite leader sequence enhances translation of mRNAs late after infection. Proc Natl Acad Sci U S A. Jun. 1984;81(12):3655-3659.

Lonberg and Huszar, Human Antibodies From Transgenic Mice. Int Rev Immunol. 1995;13(1):65-93.

Long, Regulation of immune responses through inhibitory receptors. Annu Rev Immunol. 1999;17:875-904.

Lowy et al., Isolation of transforming DNA: Cloning the hamster aprt gene. Cell. Dec. 1980;22(3):817-823.

Lucas et al., MAGE-B5, MAGE-B6, MAGE-C2, and MAGE-C3: four new members of the MAGE family with tumor-specific expression. Int J Cancer. Jul. 1, 2000;87(1):55-60.

Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.

Mack et al., A small bispecific antibody construct expressed as a functional single-chain molecule with high tumor cell cytotoxicity. Proc Natl Acad Sci U S A. Jul. 18, 1995;92(15):7021-7025.

Madden et al., Applications of Network BLAST Server. Methods Enzymol. 1996;266:131-141.

Mandruzzato et al., A CASP-8 Mutation Recognized by Cytolytic T Lymphocytes on a Human Head and Neck Carcinoma. J Exp Med. Aug. 29, 1997;186(5):785-793.

Marshall, Glycoproteins. Annu Rev Biochem. 1972;41:673-702.

Simon et al., Cervical response to vaccination against HPV16 E7 in case of severe dysplasia. Eur J Obstet Gynecol Reprod Biol. Aug. 15, 2003;109(2):219-223.

Sjolander et al., Serological divergence of Dobrava and Saaremaa hantaviruses: evidence for two distinct serotypes. Epidemiol Infect Feb. 2002;128(1):99-103.

Slager et al., Induction of CAMEL/NY-ESO-ORF2-specific CD8+ T cells upon stimulation with dendritic cells infected with a modified Ad5 vector expressing a chimeric Ad5/35 fiber Cancer Gene Ther Mar. 2004;11(3):227-236.

Slager et al., Identification of multiple HLA-DR-restricted epitopes of the tumor-associated antigen CAMEL by CD4+ Th1/Th2 lymphocytes. J Immunol. Apr. 15, 2004;172(8):5095-5102.

Slamon et al., Use of Chemotherapy plus a Monoclonal Antibody against HER2 for Metastatic Breast Cancer That Overexpresses HER2. N Engl J Med. Mar. 15, 2001;344(11):783-792.

Small et al., Immunotherapy of Hormone-Refractory Prostate Cancer With Antigen-Loaded Dendritic Cells. J Clin Oncol. Dec. 1, 2000;18(23):3894-3903.

Smith et al., Neutralization of HIV-1 Subtypes: Implications for Vaccine Formulations. J Med Virol. Nov. 1998;56(3):264-268.

Smits et al., Phylogenetic and Evolutionary Relationships among Torovirus Field Variants: Evidence for Multiple Intertypic Recombination Events. J Virol. Sep. 2003;77(17):9567-9577.

Spiro, Protein glycosylation: nature, distribution, enzymatic formation, and disease implications of glycopeptide bonds. Glycobiology. Apr. 2002;12(4):43R-56R.

Stams et al., Expression Levels of TEL, AML1, and the Fusion Products TEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.

States et al., Improved Sensitivity of Nucleic Acid Database Searches Using Application-Specific Scoring Matrices. Methods: A Compan Meth Enzymol. 1991;3(1):66-70.

Steenbakkers et al., A new approach to the generation of human or murine antibody producing hybridomas. J Immunol Methods. Jul. 31, 1992;152(1):69-77.

Steenbakkers et al., Efficient generation of monoclonal antibodies from preselected antigen-specific B cells. Efficient immortalization of preselected B cells. Mol Biol Rep. Mar. 1994;19(2):125-134.

Steffens et al., Immunohistochemical analysis of tumor antigen saturation following injection of monoclonal antibody G250. Anticancer Res. Mar.-Apr. 1999;19(2A):1197-1200.

Stirnadel et al., Assessment of different sources of variation in the antibody responses to specific malaria antigens in children in Papua New Guinea. Int J Epidemiol. Jun. 2000;29(3):579-586.

Stolier et al., Initial experience with surgical treatment planning in the newly diagnosed breast cancer patient at high risk for BRCA-1 or BRCA-2 mutation. Breast J. Nov.-Dec. 2004;10(6):475-480.

Strbo et al., Secreted heat shock protein gp96-Ig: next-generation vaccines for cancer and infectious diseases. Immunol Res. Dec. 2013;57(1-3):311-325.

Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.

Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.

(56) References Cited

OTHER PUBLICATIONS

Szybalska and Szybalski, Genetics of Human Cell Lines, IV. DNA-Mediated Heritable Transformation of a Biochemical Trait. Proc Natl Acad Sci U S A. Dec. 15, 1962;48:2026-2034.
Tachibana et al., Altered reactivity of immunoglobulin produced by human-human hybridoma cells transfected by pSV2-neo gene. Cytotechnology. Jul. 1991;6(3):219-226.
Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.
Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.
Tan et al., "Superhumanized" Antibodies: Reduction of Immunogenic Potential by Complementarity-Determining Region Grafting with Human Germline Sequences: Application to an Anti-CD28. J Immunol. Jul. 15, 2002;169(2):1119-1125.
Tanaka et al., Expression of Tumor-Rejection Antigens in Gynecologic Cancers. Jpn J Cancer Res. Nov. 2000;91(11):1177-1184.
Tang et al., Use of a Peptide Mimotope to Guide the Humanization of MRK-16, an Anti-P-glycoprotein Monoclonal Antibody. J Biol Chem. Sep. 24, 1999;274(39):27371-27378.
Tannapfel et al., BRAF Gene Mutations Are Rare Events in Gastroenteropancreatic Neuroendocrine Tumors. Am J Clin Pathol. Feb. 2005;123(2):256-260I.
Tolstoshev, Gene Therapy, Concepts, Current Trials and Future Directions. Annu Rev Pharmacol Toxicol. 1993;33:573-596.
Traunecker et al., Bispecific single chain molecules (Janusins) target cytotoxic lymphocytes on HIV infected cells. EMBO J. Dec. 1991;10(12):3655-3659.
Treurnicht et al., HHV-8 subtypes in South Africa: identification of a case suggesting a novel B variant. J Med Virol. Feb. 2002;66(2):235-240.
Trimble et al., Comparison of the CD8+ T cell responses and antitumor effects generated by DNA vaccine administered through gene gun, biojector, and syringe. Vaccine. Sep. 8, 2003;21(25-26):4036-4042.
Trincado et al., Human Cytomegalovirus Strains Associated With Congenital and Perinatal Infections. J Med Virol. Aug. 2000;61(4):481-487.
Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.
Tsao and Sober, Melanoma Treatment Update. Dermatol Clin. Apr. 2005;23(2):323-333.
Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).
Tsurushita and Vasquez, Chapter 33—Humanization of Monoclonal Antibodies. Molecular Biology of B Cells, 2004:533-545.
Vallejo et al., Nucleotide Sequence and Restriction Fragment-Length Polymorphism Analysis of Human T-Cell Lymphotropic Virus Type II (HTLV-II) in Southern Europe: Evidence for the HTLV-ILA and HTLV-ILB Subtypes. J Acquir Immune Defic Syndr Hum Retrovirol. Dec. 1, 1996;13(4):384-391.
Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.
van Erp et al., Application of a sol particle immunoassay to the determination of affinity constants of monoclonal antibodies. J Immunoassay. 1991;12(3):425-443.
Van Heeke and Schuster, Expression of Human Asparagine Synthetase in *Escherichia coli*. J Biol Chem. Apr. 5, 1989;264(10):5503-5509.
Vance et al., Patterns of Pathogenesis: Discrimination of Pathogenic and Nonpathogenic Microbes by the Innate Immune System. Cell Host Microbe. Jul. 23, 2009;6(1):10-21.
Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.
Vaughan et al., Human Antibodies with Sub-nanomolar Affinities Isolated from a Large Non-immunized Phage Display Library. Nat Biotechnol. Mar. 1996;14(3):309-314.
Verhoeyen et al., Reshaping human antibodies: grafting an antilysozyme activity. Science. Mar. 25, 1988;239(4847):1534-1536.
Vilas Boas et al., Cytomegalovirus Glycoprotein B Genotypes and Central Nervous System Disease in AIDS Patients. J Med Virol. Nov. 2003;71(3):404-407.
Vilchez and Butel, Emergent Human Pathogen Simian Virus 40 and Its Role in Cancer. Clin Microbiol Rev. Jul. 2004;17(3):495-508.
Virok et al., Chlamydial Infection Induces Pathobiotype-Specific Protein Tyrosine Phosphorylation in Epithelial Cells. Infect Immun. Apr. 2005;73(4):1939-1946.
Volkel et al., Optimized linker sequences for the expression of monomeric and dimeric bispecific single-chain liabodies. Protein Eng. Oct. 2001;14(10):815-823.
Von Heijne, Patterns of Amino Acids near Signal-Sequence Cleavage Sites. Eur J Biochem. Jun. 1, 1983;133(1):17-21.
Von Heijne, A new method for predicting signal sequence cleavage sites. Nucleic Acids Res. Jun. 11, 1986;14(11):4683-4690.
Matsumoto et al., Expression of the SART-1 antigens in uterine cancers. Jpn J Cancer Res. Dec. 1998;89(12):1292-1295.
Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p53. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
Mendez et al., Functional transplant of megabase human immunoglobulin loci recapitulates human antibody response in mice. Nat Genet. Feb. 1997 ;15(2):146-156.
Menne et al., A comparison of signal sequence prediction methods using a test set of signal peptides.—Applications Note. Bioinformatics. Aug. 2000;16(8):741-742.
Merchant et al., The LMP2A ITAM Is Essential for Providing B Cells with Development and Survival Signals in Vivo. J Virol. Oct. 2000;74(19):9115-9124.
Meyaard et al., LAIR-1, a Novel Inhibitory Receptor Expressed on Human Mononuclear Leukocytes. Immunity. Aug. 1997;7(2):283-290.
Milgrom et al., Treatment of Allergic Asthma with Monoclonal Anti-IgE Antibody. For the rhuMAb-E25 Study Group. N Engl J Med. Dec. 23, 1999;341(26):1966-1973.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Mimura et al., The influence of glycosylation on the thermal stability and effector function expression of human IgG1-Fc: properties of a series of truncated glycoforms. Mol Immunol. Aug.-Sep. 2000;37(12-13):697-706.
Molijn et al., Molecular diagnosis of human papillomavirus (HPV) infections. J Clin Virol. Mar. 2005;32 Suppl 1: S43-51.
Moreau-Aubry et al., A Processed Pseudogene Codes for a New Antigen Recognized by a Cd8+ T Cell Clone on Melanoma. J Exp Med. May 1, 2000;191(9):1617-1624.
Morgan and Anderson, Human gene therapy. Annu Rev Biochem. 1993;62:191-217.
Morrison, Transfectomas Provide Novel Chimeric Antibodies. Science. Sep. 20, 1985;229(4719):1202-1207.

(56) References Cited

OTHER PUBLICATIONS

Morrison et al., Chimeric human antibody molecules: mouse antigen-binding domains with human constant region domains. Proc Natl Acad Sci USA. Nov. 1984;81(21):6851-6855.

Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. Jun. 1999;5(6):1331-1338.

Mukhopadhyay et al., A structural perspective of the flavivirus life cycle. Nat Rev Microbiol. Jan. 2005;3(1):13-22.

Mulders et al., Tumor antigens and markers in renal cell carcinoma. Urol Clin North Am. Aug. 2003;30(3):455-465.

Muller et al., MeCP2 and MBD2 expression in human neoplastic and non-neoplastic breast tissue and its association with oestrogen receptor status. Br J Cancer Nov. 17, 2003;89(10):1934-1939.

Mulligan, The Basic Science of Gene Therapy. Science. May 14, 1993;260(5110):926-932.

Mulligan et Berg, Selection for animal cells that express the *Escherichia coli* gene coding for xanthine-guanine phosphoribosyltransferase. Proc Natl Acad Sci U S A. Apr. 1981;78(4):2072-2076.

Muminova et al., Characterization of human mesothelin transcripts in ovarian and pancreatic cancer. BMC Cancer. May 12, 2004;4:19.

Murray et al., Epitope Affinity Chromatography and Biophysical Studies of Monoclonal Antibodies and Recombinant Antibody Fragments. J Chromatogr Sci. Jul. 2002;40(6):343-349.

Muyldermans et al., Recognition of antigens by single-domain antibody fragments: the superfluous luxury of paired domains. Trends Biochem Sci. Apr. 2001;26(4):230-235.

Nair et al., Induction of cytotoxic T cell responses and tumor immunity against unrelated tumors using telomerase reverse transcriptase RNA transfected dendritic cells. Nat Med. Sep. 2000;6(9):1011-1017.

Nakatsura et al., Cellular and humoral immune responses to a human pancreatic cancer antigen, coactosin-like protein, originally defined by the SEREX method. Eur J Immunol. Mar. 2002;32(3):826-836.

Nakatsura et al., Glypican-3, overexpressed specifically in human hepatocellular carcinoma, is a novel tumor marker. Biochem Biophys Res Commun. Jun. 20, 2003;306(1):16-25.

Nakatsura et al., Identification of Glypican-3 as a Novel Tumor Marker for Melanoma. Clin Cancer Res. Oct. 1, 2004;10(19):6612-6621.

Nelson and Griswold, A computer program for calculating antibody affinity constants. Comput Methods Programs Biomed. Jul.-Aug. 1988;27(1):65-68.

Nett et al., A combinatorial genetic library approach to target heterologous glycosylation enzymes to the endoplasmic reticulum or the Golgi apparatus of Pichia pastoris. Yeast. Mar. 2011;28(3):237-252.

Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.

Nicoletto et al., BRCA-1 and BRCA-2 mutations as prognostic factors in clinical practice and genetic counselling. Cancer Treat Rev. Oct. 2001;27(5):295-304.

Nygren, Conjugation of Horseradish Peroxidase to Fab Fragments with Different Homobifunctional and Heterobifunctional Cross-Linking Reagents. A Comparative Study. J Histochem Cytochem. May 1982;30(5):407-412.

Obeid et al., Vaccines, Adjuvants, and Dendritic Cell Activators—Current Status and Future Challenges. Semin Oncol. Aug. 2015; 42(4): 549-561.

Oberste et al., Evidence for Frequent Recombination within Species Human Enterovirus B Based on Complete Genomic Sequences of All Thirty-Seven Serotypes. J Virol. Jan. 2004;78(2):855-867.

Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.

O'Connor et al., Humanization of an antibody against human protein C and calcium-dependence involving framework residues. Protein Eng. Apr. 1998;11(4):321-328.

O'Hare et al., Transformation of mouse fibroblasts to methotrexate resistance by a recombinant plasmid expressing a prokaryotic dihydrofolate reductase. Proc Natl Acad Sci U S A. Mar. 1981;78(3):1527-1531.

Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.

Orvell et al., Antigenic relationships between six genotypes of the small hydrophobic protein gene of mumps virus. J Gen Virol. Oct. 2002;83(Pt 10):2489-2496.

Otte et al., MAGE-A Gene Expression Pattern in Primary Breast Cancer. Cancer Res. Sep. 15, 2001;61(18):6682-6687.

Oyston and Quarry, Tularemia vaccine: past, present and future. Antonie Van Leeuwenhoek. May 2005;87(4):277-281.

Padilla et al., Imaging of the varicella zoster virion in the viral highways: Comparison with herpes simplex viruses 1 and 2, cytomegalovirus, pseudorabies virus, and human herpes viruses 6 and 7. J Med Virol. 2003;70 Suppl 1:S103-S110.

Pain and Surolia, Preparation of protein A-peroxidase monoconjugate using a heterobifunctional reagent, and its use in enzyme immunoassays. J Immunol Methods. 1981;40(2):219-230.

Pandey et al., Identification of a Novel Immunoreceptor Tyrosine-based Activation Motif-containing Molecule, STAM2, by Mass Spectrometry and Its Involvement in Growth Factor and Cytokine Receptor Signaling Pathways. J Biol Chem. Dec. 8, 2000;275(49):38633-38639.

Parekh et al., Association of rheumatoid arthritis and primary osteoarthritis with changes in the glycosylation pattern of total serum IgG. Nature. Aug. 1-7, 1985;316(6027):452-457.

Patel et al., Development of a simple restriction fragment length polymorphism assay for subtyping of coxsackie B viruses. J Virol Methods. Sep. 15, 2004;120(2):167-172.

Peh et al., Frequent presence of subtype a virus in Epstein-Barr virus-associated malignancies. Pathology. Oct. 2002;34(5):446-450.

Pisarev et al., Full-length dominant-negative survivin for cancer immunotherapy. Clin Cancer Res. Dec. 15, 2003;9(17):6523-6533.

* cited by examiner

SEQUENCE LISTING

```
<160> NUMBER OF SEQ ID NOS: 48

<210> SEQ ID NO 1
<211> LENGTH: 5
<212> TYPE: PRT
<213> ORGANISM: Artificial Sequence
<220> FEATURE:
<223> OTHER INFORMATION: hPD1.29A heavy chain CDR1

<400> SEQUENCE: 1

Thr Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: hPD1.29A heavy chain CDR2

<400> SEQUENCE: 2

Trp Ile Phe Pro Gly Asp Val Ser Thr Gln Tyr Asn Glu Lys Phe Gln
1               5                   10                  15

Asp

<210> SEQ ID NO 3
<211> LENGTH: 8
<212> TYPE: PRT
<213> ORGANISM: Artificial Sequence
<220> FEATURE:
<223> OTHER INFORMATION: hPD1.29A heavy chain CDR3

<400> SEQUENCE: 3

Glu Ala Tyr Asp Tyr Ala Val Tyr
1               5

<210> SEQ ID NO 4
<211> LENGTH: 11
<212> TYPE: PRT
<213> ORGANISM: Artificial Sequence
```

<220> FEATURE:
<223> OTHER INFORMATION: hPD1.29A light chain CDR1

<400> SEQUENCE: 4

Lys Ala Ser Gln Asn Val Asp Thr Asn Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: hPD1.29A light chain CDR2

<400> SEQUENCE: 5

Ser Ala Ser Tyr Arg Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: hPD1.29A light chain CDR3

<400> SEQUENCE: 6

Gln Gln Tyr Asn Asn Tyr Pro Phe Thr
1               5

<210> SEQ ID NO 7
<211> LENGTH: 117
<212> TYPE: PRT
<213> ORGANISM: Artificial Sequence
<220> FEATURE:
<223> OTHER INFORMATION: hPD1.29H5L4 heavy chain variable region

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Thr Tyr
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: hPD1.29H5L4 light chain variable region

<400> SEQUENCE: 8

Asp Ile Gln Met Thr Gln Ala Pro Ser Ser Leu Ser Ala Ser Val Gly

```
              1               5                  10                 15
Asp Arg Val Thr Ile Thr Cys Lys Ala Ser Gln Asn Val Asp Thr Asn
                    20                  25                  30

Val Ala Trp Phe Gln Gln Lys Pro Gly Lys Ala Pro Lys Ser Leu Ile
                35                  40                  45

Phe Ser Ala Ser Tyr Arg Tyr Ser Gly Val Pro Ser Arg Phe Ser Gly
            50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Tyr Asn Asn Tyr Pro Phe
                    85                  90                  95

Thr Phe Gly Gly Gly Thr Lys Leu Glu Ile Lys
                100                 105

<210> SEQ ID NO 9
<211> LENGTH: 351
<212> TYPE: DNA
<213> ORGANISM: Artificial Sequence
<220> FEATURE:
<223> OTHER INFORMATION: hPD1.29H5L4 heavy chain variable region

<400> SEQUENCE: 9
gaagtgcagc tggtgcagtc tggcgccgaa gtgaagaaac ctggcgcctc cgtgaaggtg    60
tcctgcaagg cctccggcta catcttcacc acctactaca tccactgggt caagcaggcc   120
cctggcaagg gcctggaatg gatcggctgg atcttccccg gcgacgtgtc cacccagtac   180
aacgagaagt tccaggacaa ggccaccatc accgtggaca gtccgcctc accgcctac     240 atgcagctgt cctccctgag atccgaggac accgccgtgt actactgtac cagagaggcc   300
tacgactacg ctgtgtactg gggccagggc accctcgtga cagtgtcctc t             351

<210> SEQ ID NO 10
<211> LENGTH: 321
<212> TYPE: DNA
<213> ORGANISM: Artificial Sequence
<220> FEATURE:
<223> OTHER INFORMATION: hPD1.29H5L4 light chain variable region

<400> SEQUENCE: 10
gacatccaga tgacccaggc cccttccagc ctgtctgctt ccgtgggcga cagagtgacc    60
atcacatgca aggcctccca gaacgtggac accaacgtgg cctggttcca gcagaagcct   120
ggcaaggccc ccaagtccct gatcttctcc gcctcctacc ggtactccgg cgtgccctct   180
agattctccg gctctggctc tggcaccgac tttaccctga ccatctccag cctgcagccc   240
gaggacttcg ccacctacta ctgccagcag tacaacaact ccccttcac cttcggcgga    300 ggcaccaagc tggaaatcaa g                                              321

<210> SEQ ID NO 11
<211> LENGTH: 288
<212> TYPE: PRT
<213> ORGANISM: Homo sapiens

<400> SEQUENCE: 11

Met Gln Ile Pro Gln Ala Pro Trp Pro Val Val Trp Ala Val Leu Gln
  1               5                  10                  15

Leu Gly Trp Arg Pro Gly Trp Phe Leu Asp Ser Pro Asp Arg Pro Trp
                 20                  25                  30

Asn Pro Pro Thr Phe Ser Pro Ala Leu Leu Val Val Thr Glu Gly Asp
```

```
                    35                  40                  45
Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                     85                  90                  95

Val Thr Gln Leu Pro Asn Gly Arg Asp Phe His Met Ser Val Val Arg
                    100                 105                 110

Ala Arg Arg Asn Asp Ser Gly Thr Tyr Leu Cys Gly Ala Ile Ser Leu
                    115                 120                 125

Ala Pro Lys Ala Gln Ile Lys Glu Ser Leu Arg Ala Glu Leu Arg Val
                    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
                    180                 185                 190

Ser Arg Ala Ala Arg Gly Thr Ile Gly Ala Arg Arg Thr Gly Gln Pro
                    195                 200                 205

Leu Lys Glu Asp Pro Ser Ala Val Pro Val Phe Ser Val Asp Tyr Gly
                    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                    245                 250                 255

Met Gly Thr Ser Ser Pro Ala Arg Arg Gly Ser Ala Asp Gly Pro Arg
                    260                 265                 270

Ser Ala Gln Pro Leu Arg Pro Glu Asp Gly His Cys Ser Trp Pro Leu
                    275                 280                 285

<210> SEQ ID NO 12
<211> LENGTH: 288
<212> TYPE: PRT
<213> ORGANISM: Macaca fascicularis

<400> SEQUENCE: 12

Met Gln Ile Pro Gln Ala Pro Trp Pro Val Val Trp Ala Val Leu Gln
 1                   5                  10                  15

Leu Gly Trp Arg Pro Gly Trp Phe Leu Glu Ser Pro Asp Arg Pro Trp
                     20                  25                  30

Asn Ala Pro Thr Phe Ser Pro Ala Leu Leu Val Thr Glu Gly Asp
                     35                  40                  45

Asn Ala Thr Phe Thr Cys Ser Phe Ser Asn Ala Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                     85                  90                  95

Val Thr Arg Leu Pro Asn Gly Arg Asp Phe His Met Ser Val Val Arg
                    100                 105                 110

Ala Arg Arg Asn Asp Ser Gly Thr Tyr Leu Cys Gly Ala Ile Ser Leu
                    115                 120                 125
```

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Gln Gly Thr Ile Glu Ala Arg Arg Thr Gly Gln Pro
                195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
                260                 265                 270

Ser Pro Arg Pro Leu Arg Pro Glu Asp Gly His Cys Ser Trp Pro Leu
                275                 280                 285

<210> SEQ ID NO 13
<211> LENGTH: 867
<212> TYPE: DNA
<213> ORGANISM: Homo sapiens

<400> SEQUENCE: 13
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcaggcccg gcgcaatgac agcggcacc     360 tacctctgtg gggccatctc cctggccccc aaggcgcaga tcaaagagag cctgcgggca    420
gagctcaggg tgacagagag aagggcagaa gtgcccacag cccaccccag ccctcacccc    480
aggccagccg gccagttcca aaccctggtg gttggtgtcg tgggcggcct gctgggcagc    540
ctggtgctgc tagtctgggt cctggccgtc atctgctccc gggccgcacg agggacaata    600
ggagccaggc gcaccggcca gcccctgaag gaggacccct cagccgtgcc tgtgttctct    660
gtggactatg gggagctgga tttccagtgg cgagagaaga ccccggagcc ccccgtgccc    720
tgtgtccctg agcagacgga gtatgccacc attgtctttc ctagcggaat gggcacctca    780
tcccccgccc gcaggggctc agctgacggc cctcggagtg cccagccact gaggcctgag    840
gatggacact gctcttggcc cctctga                                        867

<210> SEQ ID NO 14
<211> LENGTH: 117
<212> TYPE: PRT
<213> ORGANISM: Artificial Sequence
<220> FEATURE:
<223> OTHER INFORMATION: template DJ011535

<400> SEQUENCE: 14

Glu Val Gln Leu Val Glu Ser Gly Ala Glu Val Lys Lys Pro Gly Ala

```
                1               5                   10                  15
            Ser Val Lys Val Ser Cys Lys Ala Ser Gly Tyr Ile Phe Thr Thr Tyr
                            20                  25                  30

Tyr Ile His Trp Val Lys Gln Ala Pro Gly Lys Gly Leu Glu Trp Ile
                            35                  40                  45

Gly Trp Ile Phe Pro Gly Asp Val Ser Thr Gln Tyr Asn Glu Lys Phe
                        50                  55                  60

Gln Asp Lys Ala Thr Ile Thr Val Asp Lys Ser Ala Ser Thr Ala Tyr
            65                  70                  75                  80

Met Glu Leu Ser Ser Leu Arg Ser Glu Asp Thr Ala Val Tyr Tyr Cys
                            85                  90                  95

Thr Arg Glu Ala Tyr Asp Tyr Ala Val Tyr Trp Gly Gln Gly Thr Leu
                        100                 105                 110

Val Thr Val Ser Ser
                        115
```

<210> SEQ ID NO 15
<211> LENGTH: 117
<212> TYPE: PRT
<213> ORGANISM: Artificial Sequence
<220> FEATURE:
<223> OTHER INFORMATION: template DD247024

<400> SEQUENCE: 15

```
            Glu Val Gln Leu Gln Glu Ser Gly Ala Glu Val Val Lys Pro Gly Ala
            1               5                   10                  15

Ser Met Lys Val Ser Cys Lys Ala Ser Gly Tyr Ile Phe Thr Thr Tyr
                            20                  25                  30

Tyr Ile His Trp Val Lys Gln Ala Pro Gly Lys Asn Leu Glu Trp Ile
                            35                  40                  45

Gly Trp Ile Phe Pro Gly Asp Val Ser Thr Gln Tyr Asn Glu Lys Phe
                        50                  55                  60

Gln Asp Lys Ala Thr Ile Ser Val Asp Lys Ser Ala Ser Thr Ala Tyr
            65                  70                  75                  80

Met Glu Leu Leu Ser Leu Thr Ser Glu Asp Ser Ala Val Tyr Tyr Cys
                            85                  90                  95

Thr Arg Glu Ala Tyr Asp Tyr Ala Val Tyr Trp Gly Gln Gly Thr Ser
                        100                 105                 110

Val Thr Val Ser Ser
                        115
```

<210> SEQ ID NO 16
<211> LENGTH: 117
<212> TYPE: PRT
<213> ORGANISM: Artificial Sequence
<220> FEATURE:
<223> OTHER INFORMATION: template DI109259

<400> SEQUENCE: 16

```
            Glu Val Gln Leu Val Glu Ser Gly Ala Glu Val Val Lys Pro Gly Ala
            1               5                   10                  15

Ser Val Lys Val Ser Cys Lys Ala Ser Gly Tyr Ile Phe Thr Thr Tyr
                            20                  25                  30

Tyr Ile His Trp Val Arg Gln Ala Pro Gly Lys Gly Leu Glu Trp Ile
                            35                  40                  45

Gly Trp Ile Phe Pro Gly Asp Val Ser Thr Gln Tyr Asn Glu Lys Phe
                        50                  55                  60
```

Gln Asp Lys Ala Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Glu Ala Tyr Asp Tyr Ala Val Tyr Trp Gly Gln Gly Thr Thr
        100                 105                 110

Val Thr Val Ser Ser
        115

<210> SEQ ID NO 17
<211> LENGTH: 117
<212> TYPE: PRT
<213> ORGANISM: Artificial Sequence
<220> FEATURE:
<223> OTHER INFORMATION: template IGHV1-3*01

<400> SEQUENCE: 17

Glu Val Gln Leu Val Gln Ala Gly Ala Glu Val Lys Lys Pro Gly Ala
1               5                   10                  15

Ser Val Lys Val Ser Cys Lys Ala Ser Gly Tyr Arg Phe Thr Thr Tyr
            20                  25                  30

Tyr Ile His Trp Val Arg Gln Ala Pro Gly Gln Arg Leu Glu Trp Met
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Ala Tyr Asp Tyr Ala Val Tyr Trp Gly Gln Ala Thr Leu
        100                 105                 110

Val Thr Val Ser Ala
        115

<210> SEQ ID NO 18
<211> LENGTH: 107
<212> TYPE: PRT
<213> ORGANISM: Artificial Sequence
<220> FEATURE:
<223> OTHER INFORMATION: template AY942002

<400> SEQUENCE: 18

Asp Ile Gln Leu Thr Gln Ala Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
            85                  90                  95

Thr Phe Gly Gly Gly Thr Lys Leu Glu Ile Lys
        100                 105

<210> SEQ ID NO 19

```
<211> LENGTH: 107
<212> TYPE: PRT
<213> ORGANISM: Artificial Sequence
<220> FEATURE:
<223> OTHER INFORMATION: template DI112350

<400> SEQUENCE: 19

Asp Ile Gln Met Thr Gln Ala Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Ser Leu Ser Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gly Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: template FR820880

<400> SEQUENCE: 20

Asp Ile Gln Met Thr Gln Ala Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gly Gly Thr Lys Val Glu Ile Lys
            100                 105

<210> SEQ ID NO 21
<211> LENGTH: 20
<212> TYPE: PRT
<213> ORGANISM: Artificial Sequence
<220> FEATURE:
<223> OTHER INFORMATION: Peptide that allowed binding of 5C4

<400> SEQUENCE: 21

Thr Ser Glu Ser Phe Val Leu Asn Trp Tyr Arg Met Ser Pro Ser Asn
1               5                   10                  15

Gln Thr Asp Lys
            20

<210> SEQ ID NO 22
<211> LENGTH: 20
```

-continued

```
<212> TYPE: PRT
<213> ORGANISM: Artificial Sequence
<220> FEATURE:
<223> OTHER INFORMATION: Peptide that allowed binding of 5C4

<400> SEQUENCE: 22

Asn Thr Ser Glu Ser Phe Val Leu Asn Trp Tyr Arg Met Ser Pro Ser
1               5                   10                  15

Asn Gln Thr Asp
            20

<210> SEQ ID NO 23
<211> LENGTH: 20
<212> TYPE: PRT
<213> ORGANISM: Artificial Sequence
<220> FEATURE:
<223> OTHER INFORMATION: Peptide that allowed binding of 5C4

<400> SEQUENCE: 23

Ser Glu Ser Phe Val Leu Asn Trp Tyr Arg Met Ser Pro Ser Asn Gln
1               5                   10                  15

Thr Asp Lys Leu
            20

<210> SEQ ID NO 24
<211> LENGTH: 18
<212> TYPE: PRT
<213> ORGANISM: Artificial Sequence
<220> FEATURE:
<223> OTHER INFORMATION: Peptide that allowed binding of 5C4

<400> SEQUENCE: 24

Ser Glu Ser Phe Val Leu Asn Trp Tyr Arg Met Ser Pro Ser Asn Gln
1               5                   10                  15

Thr Asp

<210> SEQ ID NO 25
<211> LENGTH: 20
<212> TYPE: PRT
<213> ORGANISM: Artificial Sequence
<220> FEATURE:
<223> OTHER INFORMATION: Peptide that allowed binding of 5C4

<400> SEQUENCE: 25

Pro Gly Trp Phe Leu Asp Ser Pro Asp Arg Pro Trp Asn Pro Pro Thr
1               5                   10                  15

Phe Ser Pro Ala
            20

<210> SEQ ID NO 26
<211> LENGTH: 20
<212> TYPE: PRT
<213> ORGANISM: Artificial Sequence
<220> FEATURE:
<223> OTHER INFORMATION: Peptide that allowed binding of 5C4

<400> SEQUENCE: 26

Trp Phe Leu Asp Ser Pro Asp Arg Pro Trp Asn Pro Pro Thr Phe Ser
1               5                   10                  15

Pro Ala Leu Leu
            20

<210> SEQ ID NO 27
<211> LENGTH: 18
```

```
-continued

<212> TYPE: PRT
<213> ORGANISM: Artificial Sequence
<220> FEATURE:
<223> OTHER INFORMATION: Peptide that allowed binding of 5C4

<400> SEQUENCE: 27

Trp Phe Leu Asp Ser Pro Asp Arg Pro Trp Asn Pro Pro Thr Phe Ser
1               5                   10                  15

Pro Ala

<210> SEQ ID NO 28
<211> LENGTH: 20
<212> TYPE: PRT
<213> ORGANISM: Artificial Sequence
<220> FEATURE:
<223> OTHER INFORMATION: peptide that allowed binding to h409A11

<400> SEQUENCE: 28

Asn Thr Ser Glu Ser Phe Val Leu Asn Trp Tyr Arg Met Ser Pro Ser
1               5                   10                  15

Asn Gln Thr Asp
            20

<210> SEQ ID NO 29
<211> LENGTH: 20
<212> TYPE: PRT
<213> ORGANISM: Artificial Sequence
<220> FEATURE:
<223> OTHER INFORMATION: peptide that allowed binding to h409A11

<400> SEQUENCE: 29

Thr Ser Ser Phe Ser Asn Thr Ser Glu Ser Phe Val Leu Asn Trp Tyr
1               5                   10                  15

Arg Met Ser Pro
            20

<210> SEQ ID NO 30
<211> LENGTH: 15
<212> TYPE: PRT
<213> ORGANISM: Artificial Sequence
<220> FEATURE:
<223> OTHER INFORMATION: peptide that allowed binding to h409A11

<400> SEQUENCE: 30

Asn Thr Ser Glu Ser Phe Val Leu Asn Trp Tyr Arg Met Ser Pro
1               5                   10                  15

<210> SEQ ID NO 31
<211> LENGTH: 117
<212> TYPE: PRT
<213> ORGANISM: Artificial Sequence
<220> FEATURE:
<223> OTHER INFORMATION: mPD1.29A heavy chain variable region

<400> SEQUENCE: 31

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Ile Phe Thr Thr Tyr
            20                  25                  30

Tyr Ile His Trp Val Lys Gln Arg Pro Gly Gln Gly Leu Glu Trp Ile
        35                  40                  45

Gly Trp Ile Phe Pro Gly Asp Val Ser Thr Gln Tyr Asn Glu Lys Phe
    50                  55                  60
```

```
Gln Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Thr Arg Glu Ala Tyr Asp Tyr Ala Val Tyr Trp Gly Gln Gly Thr Leu
            100                 105                 110

Val Thr Val Ser Ala
            115

<210> SEQ ID NO 32
<211> LENGTH: 351
<212> TYPE: DNA
<213> ORGANISM: Artificial Sequence
<220> FEATURE:
<223> OTHER INFORMATION: mPD1.29A heavy chain variable region

<400> SEQUENCE: 32
caggtccaac tgcagcagtc tggacctgaa ctggtgaagc ctggggcttc agtgaggatt      60
tcctgcaagg cttctggcta catcttcaca acctactata cacattgggt gaagcagagg     120
cctggacagg gacttgagtg gattggatgg attttcctg agatgttag tactcagtat        180 aatgagaaat tccaggacaa ggccacactg actgcagaca atcttccag cacagcctac      240 atgcagctca gcagcctgac ctctgaagac tctgcggtct atttctgtac aagagaggct     300
tatgattacg cggtttactg gggccaaggg actctggtca ctgtctctgc a              351

<210> SEQ ID NO 33
<211> LENGTH: 107
<212> TYPE: PRT
<213> ORGANISM: Artificial Sequence
<220> FEATURE:
<223> OTHER INFORMATION: mPD1.29A light chain variable region

<400> SEQUENCE: 33

Asp Ile Val Met Thr Gln Ser Gln Lys Phe Met Ser Thr Ser Leu Gly
  1               5                  10                  15

Asp Arg Val Ser Val Thr Cys Lys Ala Ser Gln Asn Val Asp Thr Asn
                 20                  25                  30

Val Ala Trp Tyr Gln Gln Glu Pro Gly Gln Ser Pro Lys Ala Leu Ile
             35                  40                  45

Phe Ser Ala Ser Tyr Arg Tyr Ser Gly Val Pro Asp Arg Phe Thr Gly
         50                  55                  60

Ser Gly Ser Gly Thr Asp Phe Thr Leu Thr Ile Ser Ser Val Gln Pro
 65                  70                  75                  80

Glu Asp Leu Ala Glu Tyr Phe Cys Gln Gln Tyr Asn Asn Tyr Pro Phe
                 85                  90                  95

Thr Phe Gly Gly Gly Thr Lys Leu Glu Ile Lys
            100                 105

<210> SEQ ID NO 34
<211> LENGTH: 323
<212> TYPE: DNA
<213> ORGANISM: Artificial Sequence
<220> FEATURE:
<223> OTHER INFORMATION: mPD1.29A light chain variable region

<400> SEQUENCE: 34
gacattgtga tgacccagtc tcaaaaattc atgtccacat cactgggaga cagggtcagc      60
gtcacctgca aggccagtca gaatgtggat actaatgtag cctggtatca acaggaacca    120
```

```
gggcaatctc ctaaagccct gattttctcg gcatcctacc ggtacagtgg agtccctgat    180
cgcttcacag gcagtggatc tgggacagat ttcactctca ccatcagcag tgtgcagcct    240
gaagacttgg cagagtattt ctgtcaacaa tataacaact atccgttcac gttcggaggg    300
gggaccaagt tggaaataaa acg                                            323
```

<210> SEQ ID NO 35
<211> LENGTH: 117
<212> TYPE: PRT
<213> ORGANISM: Artificial Sequence
<220> FEATURE:
<223> OTHER INFORMATION: hPD1.29H5 A9P heavy chain variable region

<400> SEQUENCE: 35

```
Glu Val Gln Leu Val Gln Ser Gly Pro Glu Val Lys Lys Pro Gly Ala
1               5                   10                  15

Ser Val Lys Val Ser Cys Lys Ala Ser Gly Tyr Ile Phe Thr Thr Tyr
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115
```

<210> SEQ ID NO 36
<211> LENGTH: 117
<212> TYPE: PRT
<213> ORGANISM: Artificial Sequence
<220> FEATURE:
<223> OTHER INFORMATION: hPD1.29H5 K12V heavy chain variable region

<400> SEQUENCE: 36

```
Glu Val Gln Leu Val Gln Ser Gly Ala Glu Val Val Lys Pro Gly Ala
1               5                   10                  15

Ser Val Lys Val Ser Cys Lys Ala Ser Gly Tyr Ile Phe Thr Thr Tyr
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115
```

<210> SEQ ID NO 37
<211> LENGTH: 117

<212> TYPE: PRT
<213> ORGANISM: Artificial Sequence
<220> FEATURE:
<223> OTHER INFORMATION: hPD1.29H5 I28D heavy chain variable region

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Thr Tyr
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: hPD1.29H5 T30D heavy chain variable region

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Asp Thr Tyr
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 39
<211> LENGTH: 117
<212> TYPE: PRT
<213> ORGANISM: Artificial Sequence
<220> FEATURE:
<223> OTHER INFORMATION: hPD1.29H5 T31D heavy chain variable region

<400> SEQUENCE: 39

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr

```
                    20                  25                  30

Tyr Ile His Trp Val Lys Gln Ala Pro Gly Lys Gly Leu Glu Trp Ile
            35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: hPD1.29H5 T32D heavy chain variable region

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Thr Asp
                20                  25                  30

Tyr Ile His Trp Val Lys Gln Ala Pro Gly Lys Gly Leu Glu Trp Ile
            35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: hPD1.29H5 I28D T30D heavy chain variable region

<400> SEQUENCE: 41

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Asp Thr Tyr
                20                  25                  30

Tyr Ile His Trp Val Lys Gln Ala Pro Gly Lys Gly Leu Glu Trp Ile
            35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80
```

```
Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 42
<211> LENGTH: 117
<212> TYPE: PRT
<213> ORGANISM: Artificial Sequence
<220> FEATURE:
<223> OTHER INFORMATION: hPD1.29H5 I28D T31D heavy chain variable region

<400> SEQUENCE: 42

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 43
<211> LENGTH: 117
<212> TYPE: PRT
<213> ORGANISM: Artificial Sequence
<220> FEATURE:
<223> OTHER INFORMATION: hPD1.29H5 I28D T32D heavy chain variable region

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Thr Asp
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 44
```

```
<211> LENGTH: 117
<212> TYPE: PRT
<213> ORGANISM: Artificial Sequence
<220> FEATURE:
<223> OTHER INFORMATION: hPD1.29H5 I28T T31S heavy chain variable region

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 45
<211> LENGTH: 117
<212> TYPE: PRT
<213> ORGANISM: Artificial Sequence
<220> FEATURE:
<223> OTHER INFORMATION: hPD1.29H5 A9P K12V heavy chain variable region

<400> SEQUENCE: 45

Glu Val Gln Leu Val Gln Ser Gly Pro Glu Val Val Lys Pro Gly Ala
1               5                   10                  15

Ser Val Lys Val Ser Cys Lys Ala Ser Gly Tyr Ile Phe Thr Thr Tyr
            20                  25                  30

Tyr Ile His Trp Val Lys Gln Ala Pro Gly Lys Gly Leu Glu Trp Ile
        35                  40                  45

Gly Trp Ile Phe Pro Gly Asp Val Ser Thr Gln Tyr Asn Glu Lys Phe
    50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
        115

<210> SEQ ID NO 46
<211> LENGTH: 117
<212> TYPE: PRT
<213> ORGANISM: Artificial Sequence
<220> FEATURE:
<223> OTHER INFORMATION: hPD1.29H5 A9P I28T T31S heavy chain variable
      region

<400> SEQUENCE: 46

Glu Val Gln Leu Val Gln Ser Gly Pro Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Tyr Ile His Trp Val Lys Gln Ala Pro Gly Lys Gly Leu Glu Trp Ile
            35                  40                  45

Gly Trp Ile Phe Pro Gly Asp Val Ser Thr Gln Tyr Asn Glu Lys Phe
50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
            115

<210> SEQ ID NO 47
<211> LENGTH: 117
<212> TYPE: PRT
<213> ORGANISM: Artificial Sequence
<220> FEATURE:
<223> OTHER INFORMATION: hPD1.29H5 K12V I28T T31S heavy chain variable
      region

<400> SEQUENCE: 47

Glu Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Lys Gln Ala Pro Gly Lys Gly Leu Glu Trp Ile
            35                  40                  45

Gly Trp Ile Phe Pro Gly Asp Val Ser Thr Gln Tyr Asn Glu Lys Phe
50                  55                  60

Gln Asp Lys Ala Thr Ile Thr Val Asp Lys Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Thr Arg Glu Ala Tyr Asp Tyr Ala Val Tyr Trp Gly Gln Gly Thr Leu
            100                 105                 110

Val Thr Val Ser Ser
            115

<210> SEQ ID NO 48
<211> LENGTH: 117
<212> TYPE: PRT
<213> ORGANISM: Artificial Sequence
<220> FEATURE:
<223> OTHER INFORMATION: hPD1.29H5 A9P K12V I28T T31S heavy chain
      variable region

<400> SEQUENCE: 48

Glu Val Gln Leu Val Gln Ser Gly Pro Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Lys Gln Ala Pro Gly Lys Gly Leu Glu Trp Ile
            35                  40                  45

Gly Trp Ile Phe Pro Gly Asp Val Ser Thr Gln Tyr Asn Glu Lys Phe
50                  55                  60

```
Gln Asp Lys Ala Thr Ile Thr Val Asp Lys Ser Ala Ser Thr Ala Tyr
 65              70                  75                  80

Met Gln Leu Ser Ser Leu Arg Ser Glu Asp Thr Ala Val Tyr Tyr Cys
                 85                  90                  95

Thr Arg Glu Ala Tyr Asp Tyr Ala Val Tyr Trp Gly Gln Gly Thr Leu
            100                 105                 110

Val Thr Val Ser Ser
            115
```

ANTI-PD-1 ANTIBODIES

The present application claims priority to Netherlands Patent Application No. 2017267, filed Jul. 29, 2016, which is hereby incorporated by reference in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Jul. 26, 2017, is named ABE_0004_UT_SeqListing.txt and is 41 kilobytes in size.

FIELD OF THE INVENTION

The present invention relates to treatments of conditions ameliorated by stimulation of an immune response, in particular by the stimulation of antigen-specific T-lymphocytes.

BACKGROUND OF THE INVENTION

In the field of cancer therapy, immunotherapies that increase the strength of immune responses against tumors have become an increasingly important tool. In the case of T cells, the robustness of the anti-tumor response is regulated by a balance between co-stimulatory and inhibitory signals which are referred to as "immune checkpoints." In their normal function, immune checkpoints are involved in maintaining self-tolerance and modulating the duration and amplitude of physiological immune responses in peripheral tissues in order to minimize collateral tissue damage. In disease, it is believed that tumors co-opt certain immune checkpoint pathways to generate and maintain immune resistance against T cells that are specific for tumor antigens.

Because many of the immune checkpoints are initiated by ligand-receptor interactions, they can be readily blocked by antibodies or modulated by recombinant forms of ligands or receptors. The interaction between the programmed death 1 (PD-1) receptor and its ligands PD-L1 and PD-L2 has shown promise as a target for checkpoint blockade. Engagement of PD-1 by its ligands, PD-L1 and PD-L2, induces an inhibitory signal resulting in reduced T-cell proliferation, cytokine production, and cytotoxic activity, while blockade of PD-1 or its ligands promotes antitumor activity. Additionally, PD-1 reportedly plays an important role in regulating functional exhaustion of virus-specific CD8$^+$ T cells during chronic viral infections. In vivo blockade of PD-1 has been demonstrated to restore the function of exhausted CD8+ T cells during chronic viral infections, such as human immunodeficiency virus (HIV), hepatitis B virus (HBV), and hepatitis C virus (HCV).

Antagonistic antibodies to PD-1 known as nivolumab (Opdivo) and pembrolizumab (Keytruda) have received FDA approval for the treatment of a number of cancers, including melanoma, non-small-cell lung cancer, and renal cell carcinoma, and a number of additional clinical trials are ongoing for additional indications. That said, the use of antagonistic PD-1 antibodies does have limitations. In one study, less than 30 percent of melanoma and lung cancer patients responded to treatment and at this time it is not possible to predict with certainty which patients will respond to a PD-1 antibody.

A non-limiting set of characteristics which can be indicative of a useful PD-1 antagonistic antibody include one or more of: specific binding to a PD-1-expressing cell with a nanomolar $EC_{50}$, and $K_d$, inhibition of binding between PD-1 and its ligands with a nanomolar $IC_{50}$, promotion of antigen-specific T-cell responses in vitro, no mediation of antibody-dependent cell-mediated cytotoxicity (ADCC) in T cells, and no mediation of complement-dependent cytotoxicity (CDC) in T cells.

SUMMARY OF THE INVENTION

It is an object of the present invention to provide PD-1 antagonistic antibodies comprising the structural and functional features specified below, nucleic acids encoding such PD-1 antagonistic antibodies, together with methods for their manufacture and use.

In a first aspect, the present invention relates to antibodies or antigen binding fragments thereof that binds to human programmed death-1 (PD-1) receptor, wherein the antibody or antigen binding fragment comprises one or more, and optionally each, of:
- a heavy chain variable region CDR1 comprising the amino acid sequence of SEQ ID NO: 1 or an amino acid sequence differing from SEQ ID NO: 1 by 1, 2, 3, or more conservative substitutions,
- a heavy chain variable region CDR2 comprising the amino acid sequence of SEQ ID NO: 2 or an amino acid sequence differing from SEQ ID NO: 2 by 1, 2, 3, or more conservative substitutions,
- a heavy chain variable region CDR3 comprising the amino acid sequence of SEQ ID NO: 3 or an amino acid sequence differing from SEQ ID NO: 3 by 1, 2, 3, or more conservative substitutions,
- a light chain variable region CDR1 comprising the amino acid sequence of SEQ ID NO: 4 or an amino acid sequence differing from SEQ ID NO: 4 by 1, 2, 3, or more conservative substitutions,
- a light chain variable region CDR2 comprising the amino acid sequence of SEQ ID NO: 5 or an amino acid sequence differing from SEQ ID NO: 5 by 1, 2, 3, or more conservative substitutions, and
- a light chain variable region CDR3 comprising the amino acid sequence of SEQ ID NO: 6 or an amino acid sequence differing from SEQ ID NO: 6 by 1, 2, 3, or more conservative substitutions.

In a related aspect, the present invention relates to nucleic acids encoding such antibodies or antigen binding fragments thereof that binds to human programmed death-1 (PD-1) receptor.

In certain embodiments, such antibodies or antigen binding fragments comprise
- a heavy chain sequence comprising the amino acid sequence of SEQ ID NO: 1 or an amino acid sequence differing from SEQ ID NO: 1 by 1, 2, 3, or more conservative substitutions; the amino acid sequence of SEQ ID NO: 2 or an amino acid sequence differing from SEQ ID NO: 2 by 1, 2, 3, or more conservative substitutions; and/or the amino acid sequence of SEQ ID NO: 3 or an amino acid sequence differing from SEQ ID NO: 3 by 1, 2, 3, or more conservative substitutions; and/or
- a light chain sequence comprising the amino acid sequence of SEQ ID NO: 4 or an amino acid sequence differing from SEQ ID NO: 4 by 1, 2, 3, or more conservative substitutions; the amino acid sequence of SEQ ID NO: 5 or an amino acid sequence differing from SEQ ID NO: 5 by 1, 2, 3, or more conservative substitutions; and/or the amino acid sequence of SEQ ID NO: 6 or an amino acid sequence differing from SEQ ID NO: 6 by 1, 2, 3, or more conservative substitutions.

In certain preferred embodiments, such antibodies or antigen binding fragments comprise
- a heavy chain variable region sequence comprising the amino acid sequence of SEQ ID NO: 7 or an amino acid sequence at least 90%, 95%, 97%, 98%, or 99% identical thereto, or
- a heavy chain variable region sequence comprising the amino acid sequence of SEQ ID NO: 31 or an amino acid sequence at least 90%, 95%, 97%, 98%, or 99% identical thereto;

and
- a light chain variable region sequence comprising the amino acid sequence of SEQ ID NO: 8 or an amino acid sequence at least 90%, 95%, 97%, 98%, or 99% identical thereto, or
- a light chain variable region sequence comprising the amino acid sequence of SEQ ID NO: 33 or an amino acid sequence at least 90%, 95%, 97%, 98%, or 99% identical thereto.

In certain embodiments, substitutions in SEQ ID NO: 7 include, but are not limited to, one or more substitution mutations at residue A9, K12, I28, T30, T31, and Y32. By way of example, the following substitutions are preferred: A9P, K12V, I28D, I28T, T30D, T31D, T31S, Y32D, and combinations thereof, such as I28T_T31S, I28D_T30D, I28D_T31D, I28D_Y32D, A9P_K12V, A9P_I28T_T31S, K12V_I28T_T31S and A9P_K12V_I28T_T31S. This list is not meant to be limiting.

Thus, in certain preferred embodiments, an antibodies or antigen binding fragment of the present invention comprises
- a heavy chain variable region sequence comprising the amino acid sequence of SEQ ID NO: 35,
- a heavy chain variable region sequence comprising the amino acid sequence of SEQ ID NO: 36,
- a heavy chain variable region sequence comprising the amino acid sequence of SEQ ID NO: 37,
- a heavy chain variable region sequence comprising the amino acid sequence of SEQ ID NO: 38,
- a heavy chain variable region sequence comprising the amino acid sequence of SEQ ID NO: 39,
- a heavy chain variable region sequence comprising the amino acid sequence of SEQ ID NO: 40,
- a heavy chain variable region sequence comprising the amino acid sequence of SEQ ID NO: 41,
- a heavy chain variable region sequence comprising the amino acid sequence of SEQ ID NO: 42,
- a heavy chain variable region sequence comprising the amino acid sequence of SEQ ID NO: 43,
- a heavy chain variable region sequence comprising the amino acid sequence of SEQ ID NO: 44,
- a heavy chain variable region sequence comprising the amino acid sequence of SEQ ID NO: 45,
- a heavy chain variable region sequence comprising the amino acid sequence of SEQ ID NO: 46,
- a heavy chain variable region sequence comprising the amino acid sequence of SEQ ID NO: 47, or
- a heavy chain variable region sequence comprising the amino acid sequence of SEQ ID NO: 48;

and
- a light chain variable region sequence comprising the amino acid sequence of SEQ ID NO: 8 or an amino acid sequence at least 90%, 95%, 97%, 98%, or 99% identical thereto, or
- a light chain variable region sequence comprising the amino acid sequence of SEQ ID NO: 33 or an amino acid sequence at least 90%, 95%, 97%, 98%, or 99% identical thereto.

In certain most preferred embodiments, such antibodies or antigen binding fragments comprise a heavy chain variable region sequence comprising the amino acid sequence of SEQ ID NO: 7 and a light chain variable region sequence comprising the amino acid sequence of SEQ ID NO: 8.

In certain other most preferred embodiments, such antibodies or antigen binding fragments comprise a heavy chain variable region sequence comprising the amino acid sequence of SEQ ID NO: 31 and a light chain variable region sequence comprising the amino acid sequence of SEQ ID NO: 33.

In certain embodiments, the amino acid sequence of SEQ ID NO: 7 is encoded by the nucleic acid sequence of SEQ ID NO: 9; and the amino acid sequence of SEQ ID NO: 8 is encoded by the nucleic acid sequence of SEQ ID NO: 10

In certain other preferred embodiments, the amino acid sequence of SEQ ID NO: 31 is encoded by the nucleic acid sequence of SEQ ID NO: 32; and the amino acid sequence of SEQ ID NO: 33 is encoded by the nucleic acid sequence of SEQ ID NO: 34

In certain preferred embodiments, such antibodies or antigen binding fragments comprise a heavy chain variable region sequence comprising the amino acid sequence of SEQ ID NO: 35 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 36 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 37 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 38 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 39 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 40 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 41 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 42 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 43 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 44 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 45 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 46 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 47 and a light chain variable region sequence comprising the amino acid sequence of SEQ ID NO: 8.

In certain preferred embodiments, such antibodies or antigen binding fragments comprise a heavy chain variable region sequence comprising the amino acid sequence of SEQ ID NO: 48 and a light chain variable region sequence comprising the amino acid sequence of SEQ ID NO: 8.

Antibodies or antigen binding fragments of the present invention may be obtained from a variety of species. For example, the antibodies of the present invention may comprise immunoglobulin sequences which are rabbit, mouse, rat, guinea pig, chicken, goat, sheep, donkey, human, llama or camelid sequences, or combinations of such sequences (so-called chimeric antibodies). Most preferably, the antibodies or antigen binding fragments are human or humanized antibodies or antigen binding fragments.

The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the $V_L$, $V_H$, $C_L$ and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody." Preferred therapeutic antibodies are intact IgG antibodies. The term "intact IgG" as used herein is meant as a polypeptide belonging to the class of antibodies that are substantially encoded by a recognized immunoglobulin gamma gene. In humans this class comprises IgG1, IgG2, IgG3, and IgG4. In mice this class comprises IgG, IgG2a, IgG2b, IgG3. The known Ig domains in the IgG class of antibodies are $V_H$, $C\gamma1$, $C\gamma2$, $C\gamma3$, $V_L$, and $C_L$.

In certain embodiments, the antibodies or antigen binding fragments are intact human or humanized IgG, where the pI of the Fab is about 8.2 and a charge at pH 7.4 of about 6.5. The term "about" refers to +/−10% and preferably +/−5% of a given value.

In certain embodiments, the antibodies or antigen binding fragments of the present invention have one, two, three, four, or more, and preferably each of, the following characteristics:

binds to a cell expressing human PD-1 with an $EC_{50}$<10 nM;

binds to a human PD-1 protein with a $K_d$<10 nM;

cross-reacts to *Macaca fascicularis* PD-1 protein with a $K_d$<10 nM;

inhibits binding between human PD-1 and PD-L1 with an $IC_{50}$<10 nM;

promotes antigen-specific T-cell responses in vitro;

mediates limited or no antibody-dependent cell-mediated cytotoxicity (ADCC) in PD-1 positive cells (e.g., T-cells).

mediates limited or no complement-dependent cytotoxicity (CDC) in T cells;

does not inhibit binding of 5C4 to a cell expressing human PD-1; and does not inhibit binding of h409A11 to a cell expressing human PD-1; and does not inhibit binding of H4H7798N to human PD-1.

As noted above, in related aspects, the present invention relates to isolated nucleic acids encoding an antibody or antigen binding fragment as described herein; an expression vector comprising such an isolated nucleic acid; and a host cell comprising such an isolated nucleic acid. In the case of a host cell such a cell can be a mammalian cell (e.g., a human cell such as an HEK293 cell, a hamster cell such as a CHO cell, etc.), a bacterial cell (e.g., an *E. coli* cell) a yeast cell (e.g., a *Pichia pastoris* cell, etc.), a plant cell (e.g., a *Nicotiana benthamiana* cell), etc. Mammalian cells are preferred due to glycosylation patterns that are most favorable.

The present invention also relates to methods of producing an antibody or antigen binding fragment comprising culturing such a host cell under conditions favorable to expression of the polynucleotide; and optionally, recovering the antibody or antigen binding fragment from the host cell and/or culture medium.

In another related aspect, the present invention relates to compositions comprising an antibody or antigen binding fragment of the present invention and a pharmaceutically acceptable carrier or diluent. Such compositions can further comprise one or more other therapeutically active ingredients such as:

an agonist (e.g., an agonistic antibody or antigen-binding fragment thereof, or a soluble fusion) of a TNF receptor protein, an Immunoglobulin-like protein, a cytokine receptor, an integrin, a signaling lymphocytic activation molecules (SLAM proteins), an activating NK cell receptor, a Toll like receptor, OX40, CD2, CD7, CD27, CD28, CD30, CD40, ICAM-1, LFA-1 (CD1 1a/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 1d, ITGAE, CD103, ITGAL, ITGAM, CD1 1b, ITGAX, CD1 1c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), SLAM7, BLAME (SLAMF8), SELPLG (CD162), LTBR, LAT, GADS, PAG/Cbp, CD19a, and a ligand that specifically binds with CD83;

an inhibitor of PD-L1, PD-L2, CTLA4, TIM3, LAG3, CEACAM (e.g., CEACAM-1, -3 and/or -5), VISTA, BTLA, TIGIT, LAIR1, IDO, TDO, CD160 and/or TGFR beta;

a cyclic dinucleotide or other STING pathway agonist;

a cell-based vaccine such as a bacterial strain recombinantly expressing an antigen of interest, a tumor cell vaccine, etc.;

a polypeptide vaccine, wherein the polypeptide is an antigen of interest;

a DNA vaccine; wherein the DNA vaccine encodes a polypeptide antigen of interest; and a viral vaccine, wherein the viral vaccine recombinantly expressing an antigen of interest.

Such compositions can take the form of a vaccine comprising the antibody or antigen binding fragment and optionally an antigen of interest. Such vaccines may be cancer vaccines, pathogen vaccines, etc., which are compositions administered for purposes of inducing or maintaining immunity to a particular disease or condition.

Thus, the present invention also relates to methods of treating cancer in a human subject, comprising administering to the subject an effective amount of the antibody or antigen binding fragment of the present invention, optionally in association with a further therapeutic agent or therapeutic procedure; and to methods of treating an infection or infectious disease in a human subject, comprising administering to the subject an effective amount of the antibody or antigen binding fragment of the present invention, optionally in association with a further therapeutic agent or therapeutic procedure.

In yet another related aspect, the present invention relates to method of increasing the activity of an immune cell, comprising administering to a subject in need thereof an effective amount of an antibody or antigen binding fragment of the present invention, typically for purposes of:

the treatment of cancer;

the treatment of an infection or infectious disease; or as a vaccine adjuvant; or increasing immune cell activation The antibodies or binding fragments thereof can also be used for diagnostic purposes. Thus, in another aspect, the present invention relates to methods for detecting the presence of a PD-1 protein or a fragment thereof in a sample comprising contacting the sample with an antibody or fragment the present invention and detecting the presence of a complex between the antibody or fragment and the peptide; wherein detection of the complex indicates the presence of the PD-1 protein or fragment thereof.

Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims. Methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. In addition, methods used to label whole cells for biomarker detection, e.g., by flow cytometry, immunohistochemistry, etc. can employ the antibodies or binding fragments of the present invention for detection of PD-1.

DETAILED DESCRIPTION

Figure 1:
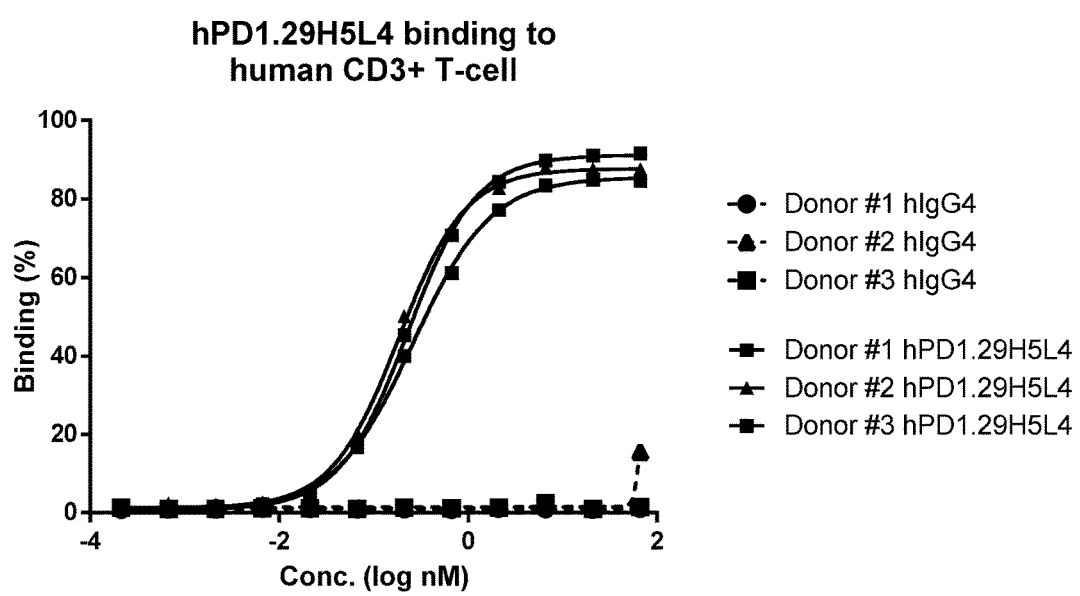
FIG. 1 shows the results of experiments demonstrating that antibody hPD1.29H5L4 against human PD-1 binds to PD-1 on activated CD3+ T-cells isolated from three different human donors.

Throughout the detailed description and examples of the invention the following abbreviations will be used:

ADCC Antibody-dependent cellular cytotoxicity

CDC Complement-dependent cytotoxicity

CDR Complementarity determining region in the immunoglobulin variable regions, defined using the Kabat numbering system CHO Chinese hamster ovary EC50 Concentration at which 50% of the total binding signal is observed ELISA Enzyme-linked immunosorbant assay FR Antibody framework region: the immunoglobulin variable regions excluding the CDR regions.

HRP Horseradish peroxidase

IFN interferon

IC50 Concentration resulting in 50% inhibition

IgG Immunoglobulin G

Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)

mAb or Mab or MAb Monoclonal antibody

SEB Staphylococcal Enterotoxin B

TT Tetanus toxoid

V region The segment of IgG chains which is variable in sequence between different antibodies. It extends to Kabat residue 109 in the light chain and 113 in the heavy chain.

$V_H$ Immunoglobulin heavy chain variable region $V_K$ Immunoglobulin kappa light chain variable region $V_L$ Immunoglobulin light chain variable region The following is a list of sequences referred to in the present specification (Table 1):

| Description | SEQ ID NO: | SEQUENCE |
|---|---|---|
| hPD1.29A heavy chain CDR1 (amino acid sequence) | 1 | TYYIH |
| hPD1.29A heavy chain CDR2 (amino acid sequence) | 2 | WIFPGDVSTQYNEKFQD |
| hPD1.29A heavy chain CDR3 (amino acid sequence) | 3 | EAYDYAVY |
| hPD1.29A light chain CDR1 (amino acid sequence) | 4 | KASQNVDTNVA |
| hPD1.29A light chain CDR2 (amino acid sequence) | 5 | SASYRYS |
| hPD1.29A light chain CDR3 (amino acid sequence) | 6 | QQYNNYPFT |
| hPD1.29H5L4 heavy chain variable region (amino acid sequence; underlined residues indicate E6Q and E81Q substitutions) | 7 | EVQLVQSGAEVKKPGASVKVSCKASGYIFTTYYIHWVKQAP GKGLEWIGWIFPGDVSTQYNEKFQDKATITVDKSASTAYMQ LSSLRSEDTAVYYCTREAYDYAVYWGQGTLVTVSS |
| hPD1.29H5L4 light chain variable region (amino acid sequence) | 8 | DIQMTQAPSSLSASVGDRVTITCKASQNVDTNVAWFQQKPG KAPKSLIFSASYRYSGVPSRFSGSGSGTDFTLTISSLQPED FATYYCQQYNNYPFTFGGGTKLEIK |
| hPD1.29H5L4 heavy chain variable region (DNA) | 9 | GAAGTGCAGCTGGTGCAGTCTGGCGCCGAAGTGAAGAAACC TGGCGCCTCCGTGAAGGTGTCCTGCAAGGCCTCCGGCTACA TCTTCACCACCTACTACATCCACTGGGTCAAGCAGGCCCCT GGCAAGGGCCTGGAATGGATCGGCTGGATCTTCCCCGGCGA CGTGTCCACCCAGTACAACGAGAAGTTCCAGGACAAGGCCA CCATCACCGTGGACAAGTCCGCCTCCACCGCCTACATGCAG CTGTCCTCCCTGAGATCCGAGGACACCGCCGTGTACTACTG TACCAGAGAGGCCTACGACTACGCTGTGTACTGGGGCCAGG GCACCCTCGTGACAGTGTCCTCT |
| hPD1.29H5L4 light chain variable region (DNA) | 10 | GACATCCAGATGACCCAGGCCCCTTCCAGCCTGTCTGCTTC CGTGGGCGACAGAGTGACCATCACATGCAAGGCCTCCCAGA ACGTGGACACCAACGTGGCCTGGTTCCAGCAGAAGCCTGGC AAGGCCCCCAAGTCCCTGATCTTCTCCGCCTCCTACCGGTA CTCCGGCGTGCCCTCTAGATTCTCCGGCTCTGGCTCTGGCA CCGACTTTACCCTGACCATCTCCAGCCTGCAGCCCGAGGAC TTCGCCACCTACTACTGCCAGCAGTACAACAACTACCCCTT CACCTTCGGCGGAGGCACCAAGCTGGAAATCAAG |
| Human PD-1 (Swiss-Prot entry Q15116) (amino acid sequence) | 11 | MQIPQAPWPVVWAVLQLGWRPGWFLDSPDRPWNPPTFSPAL LVVTEGDNATFTCSFSNTSESFVLNWYRMSPSNQTDKLAAF PEDRSQPGQDCRFRVTQLPNGRDFHMSVVRARRNDSGTYLC GAISLAPKAQIKESLRAELRVTERRAEVPTAHPSPSPRPAG QFQTLVVGVVGGLLGSLVLLVWVLAVICSRAARGTIGARRT GQPLKEDPSAVPVFSVDYGELDFQWREKTPEPPVPCVPEQT EYATIVFPSGMGTSSPARRGSADGPRSAQPLRPEDGHCSWP L |
| Macaca fascicularis PD-1 (Swiss-Prot entry B0LAj3) (amino acid sequence) | 12 | MQIPQAPWPVVWAVLQLGWRPGWFLESPDRPWNAPTFSPAL LVVTEGDNATFTCSFSNASESFVLNWYRMSPSNQTDKLAAF PEDRSQPGQDCRFRVTRLPNGRDFHMSVVRARRNDSGTYLC GAISLAPKAQIKESLRAELRVTERRAEVPTAHPSPSPRPAG QFQALVVGVVGGLLGSLVLLVWVLAVICSRAAQGTIEARRT GQPLKEDPSAVPVFSVDYGELDFQWREKTPEPPAPCVPEQT EYATIVFPSGLGTSSPARRGSADGPRSPRPLRPEDGHCSWP L |
| Human PD-1 (from NM_005018.2) (DNA) | 13 | atgcagatcccacaggcgccctggccagtcgtctgggcggt gctacaactgggctggcggccaggatggttcttagactccc cagacaggccctggaacccccaccttctccccagccctg cttctccaacacatcggagagcttcgtgctaaactggtacc gcatgagcccagcaaccagacggacaagctggccgccttc cccgaggaccgcagccagcccggccaggactgccgcttccg tgtcacacaactgcccaacgggcgtgacttccacatgagcg |

-continued

| Description | SEQ ID NO: | SEQUENCE |
|---|---|---|
| | | tggtcagggcccggcgcaatgacagcggcacctacctctgt ggggccatctccctggccccaaggcgcagatcaaagagag cctgcgggcagagctcagggtgacagagagaagggcagaag tgcccacagcccaccccagccctcacccaggccagccggc cagttccaaaccctggtggttggtgtcgtgggcggcctgct gggcagcctggtgctgctagtctgggtcctggccgtcatct gctcccgggccgcacgagggacaataggagccaggcgcacc ggccagcccctgaaggaggaccccctcagccgtgcctgtgtt ctctgtggactatggggagctggatttccagtggcgagaga agaccccggagccccccgtgccctgtgtccctgagcagacg gagtatgccaccattgtcttcctagcggaatgggcacctc atcccccgcccgcaggggctcagctgacggccctcggagtg cccagccactgaggcctgaggatggacactgctcttggccc ctctga |
| GenBank Template DJ011535 (amino acid sequence) | 14 | EVQLVESGAEVKKPGASVKVSCKASGYIFTTYYIHWVKQAP GKGLEWIGWIFPGDVSTQYNEKFQDKATITVDKSASTAYME LSSLRSEDTAVYYCTREAYDYAVYWGQGTLVTVSS |
| GenBank Template DD247024 (amino acid sequence) | 15 | EVQLQESGAEVVKPGASMKVSCKASGYIFTTYYIHWVKQAP GKNLEWIGWIFPGDVSTQYNEKFQDKATISVDKSASTAYME LLSLTSEDSAVYYCTREAYDYAVYWGQGTSVTVSS |
| GenBank Template DI109259 (amino acid sequence) | 16 | EVQLVESGAEVVKPGASVKVSCKASGYIFTTYYIHWVRQAP GKGLEWIGWIFPGDVSTQYNEKFQDKATITADESTSTAYME LSSLRSEDTAVYYCTREAYDYAVYWGQGTTVTVSS |
| GenBank Template IGHV1-3*01 (amino acid sequence) | 17 | EVQLVQAGAEVKKPGASVKVSCKASGYRFTTYYIHWVRQAP GQRLEWMGWIFPGDVSTQYNEKFQDKATITRDTSASTAYME LSSLRSEDTAVYYCAREAYDYAVYWGQATLVTVSA |
| GenBank Template AY942002 (amino acid sequence) | 18 | DIQLTQAPSSLSASVGDRVTITCKASQNVDTNVAWYQQKPG KAPKLLIYSASYRYSGVPSRFSGSGSGTDFTLTISSLQPED FATYYCQQYNNYPFTFGGGTKLEIK |
| GenBank Template DI112350 (amino acid sequence) | 19 | DIQMTQAPSSLSASVGDRVTITCKASQNVDTNVAWYQQKPG KAPKLLIYSASYRYSGVPSRFSGSGSGTEFSLSISSLQPED FATYYCQQYNNYPFTFGGGTKVEIK |
| GenBank Template FR820880 (amino acid sequence) | 20 | DIQMTQAPSSLSASVGDRVTITCKASQNVDTNVAWYQQKPG KAPKLLIYSASYRYSGVPSRFSGSGSGTDFTLTISSLQPED FATYYCQQYNNYPFTFGGGTKVEIK |
| Peptide that allowed binding of 5C4 (amino acid sequence) | 21 | TSESFVLNWYRMSPSNQTDK |
| Peptide that allowed binding of 5C4 (amino acid sequence) | 22 | NTSESFVLNWYRMSPSNQTD |
| Peptide that allowed binding of 5C4 (amino acid sequence) | 23 | SESFVLNWYRMSPSNQTDKL |
| Peptide that allowed binding of 5C4 (amino acid sequence) | 24 | SESFVLNWYRMSPSNQTD |
| Peptide that allowed binding of 5C4 (amino acid sequence) | 25 | PGWFLDSPDRPWNPPTFSPA |
| Peptide that allowed binding of 5C4 (amino acid sequence) | 26 | WFLDSPDRPWNPPTFSPALL |
| Peptide that allowed binding of 5C4 (amino acid sequence) | 27 | WFLDSPDRPWNPPTFSPA |
| Peptide that allowed binding of h409A11 (amino acid sequence) | 28 | NTSESFVLNWYRMSPSNQTD |

-continued

| Description | SEQ ID NO: | SEQUENCE |
|---|---|---|
| Peptide that allowed binding of h409A11 (amino acid sequence) | 29 | TSSFSNTSESFVLNWYRMSP |
| Peptide that allowed binding of h409A11 (amino acid sequence) | 30 | NTSESFVLNWYRMSP |
| mPD1.29A heavy chain variable region (amino acid sequence) | 31 | QVQLQQSGPELVKPGASVRISCKASGYIFTTYYIHWVKQRPGQGLEWIGWIFPGDVSTQYNEKFQDKATLTADKSSSTAYMQLSSLTSEDSAVYFCTREAYDYAVYWGQGTLVTVSA |
| mPD1.29A heavy chain variable region (DNA) | 32 | CAGGTCCAACTGCAGCAGTCTGGACCTGAACTGGTGAAGCCTGGGGCTTCAGTGAGGATTTCCTGCAAGGCTTCTGGCTACATCTTCACAACCTACTATATACATTGGGTGAAGCAGAGGCCTGGACAGGGACTTGAGTGGATTGGATGGATTTTTCCTGGAGATGTTAGTACTCAGTATAATGAGAAATTCCAGGACAAGGCCACACTGACTGCAGACAAATCTTCCAGCACAGCCTACATGCAGCTCAGCAGCCTGACCTCTGAAGACTCTGCGGTCTATTTCTGTACAAGAGAGGCTTATGATTACGCGGTTTACTGGGGCCAAGGGACTCTGGTCACTGTCTCTGCA |
| mPD1.29A light chain variable region (amino acid sequence) | 33 | DIVMTQSQKFMSTSLGDRVSVTCKASQNVDTNVAWYQQEPGQSPKALIFSASYRYSGVPDRFTGSGSGTDFTLTISSVQPEDLAEYFCQQYNNYPFTFGGGTKLEIK |
| mPD1.29A light chain variable region (DNA) | 34 | GACATTGTGATGACCCAGTCTCAAAAATTCATGTCCACATCACTGGGAGACAGGGTCAGCGTCACCTGCAAGGCCAGTCAGAATGTGGATACTAATGTAGCCTGGTATCAACAGGAACCAGGGCAATCTCCTAAAGCCCTGATTTTCTCGGCATCCTACCGGTACAGTGGAGTCCCTGATCGCTTCACAGGCAGTGGATCTGGGACAGATTTCACTCTCACCATCAGCAGTGTGCAGCCTGAAGACTTGGCAGAGTATTTCTGTCAACAATATAACAACTATCCGTTCACGTTCGGAGGGGGGACCAAGTTGGAAATAAAACG |
| hPD1.29H5 A9P heavy chain variable region (amino acid sequence; underlined residue indicates A9P substitution) | 35 | EVQLVQSGPEVKKPGASVKVSCKASGYIFTTYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 K12V heavy chain variable region (amino acid sequence; underlined residue indicates K12V substitution) | 36 | EVQLVQSGAEVVKPGASVKVSCKASGYIFTTYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 I28D heavy chain variable region (amino acid sequence; underlined residue indicates I28D substitution) | 37 | EVQLVQSGAEVKKPGASVKVSCKASGYDFTTYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 T30D heavy chain variable region (amino acid sequence; underlined residue indicates T30D substitution) | 38 | EVQLVQSGAEVKKPGASVKVSCKASGYIFDTYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 T31D heavy chain variable region (amino acid sequence; underlined residue indicates T31D substitution) | 39 | EVQLVQSGAEVKKPGASVKVSCKASGYIFTDYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 T32D heavy chain variable region (amino acid sequence; underlined residue indicates T32D substitution) | 40 | EVQLVQSGAEVKKPGASVKVSCKASGYIFTTDYIHWVKQAPGKGLEWIGWIFPGDVSTQYNEKFQDKATITVDKSASTAYMQLSSLRSEDTAVYYCTREAYDYAVYWGQGTLVTVSS |

| Description | SEQ ID NO: | SEQUENCE |
|---|---|---|
| hPD1.29H5 I28D T30D heavy chain variable region (amino acid sequence; underlined residues indicate I28D and T30D substitutions) | 41 | EVQLVQSGAEVKKPGASVKVSCKASGYDFDTYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 I28D T31D heavy chain variable region (amino acid sequence; underlined residues indicate I28D and T31D substitutions) | 42 | EVQLVQSGAEVKKPGASVKVSCKASGYDFTDYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 I28D Y32D heavy chain variable region (amino acid sequence; underlined residues indicate I28D and Y32D substitutions) | 43 | EVQLVQSGAEVKKPGASVKVSCKASGYDFTTDYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 I28I T31S heavy chain variable region (amino acid sequence; underlined residues indicate I28T and T31S substitutions) | 44 | EVQLVQSGAEVKKPGASVKVSCKASGYTFTSYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 A9P K12V heavy chain variable region (amino acid sequence; underlined residues indicate A9P and K12V substitutions) | 45 | EVQLVQSGPEVVKPGASVKVSCKASGYIFTTYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 A9P I28T I31S heavy chain variable region (amino acid sequence; underlined residues indicate A9P, I28T and T31S substitutions) | 46 | EVQLVQSGPEVKKPGASVKVSCKASGYTFTSYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 K12V I28T T31S heavy chain variable region (amino acid sequence; underlined residues indicate K12V, I28T and T31S substitutions) | 47 | EVQLVQSGAEVVKPGASVKVSCKASGYTFTSYYIHWVKQAPGKGLEWIGWIFPGDVSTQYNEKFQDKATITVDKSASTAYMQLSSLRSEDTAVYYCTREAYDYAVYWGQGTLVTVSS |
| hPD1.29H5 A9P K12V I28T T31S heavy chain variable region (amino acid sequence; underlined residues indicate A9P, K12V, I28T and T31S substitutions) | 48 | EVQLVQSGPEVVKPGASVKVSCKASGYTFTSYYIHWVKQAPGKGLEWIGWIFPGDVSTQYNEKFQDKATITVDKSASTAYMQLSSLRSEDTAVYYCTREAYDYAVYWGQGTLVTVSS |

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

"Treat" or "treating" means to administer a therapeutic agent, such as a composition containing any of the antibodies or antigen-binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

Programmed Cell Death Protein 1 (PD-1)

In an embodiment of the invention, the amino acid sequence of human PD-1 (Swiss-Prot entry Q15116) comprises the following amino acid sequence (SEQ ID NO: 11):

```
        10         20         30         40
MQIPQAPWPV VWAVLQLGWR PGWFLDSPDR PWNPPTFSPA 50         60         70         80
LLVVTEGDNA TFTCSFSNTS ESFVLNWYRM SPSNQTDKLA 90        100        110        120
AFPEDRSQPG QDCRFRVTQL PNGRDFHMSV VRARRNDSGT 130        140        150        160
YLCGAISLAP KAQIKESLRA ELRVTERRAE VPTAHPSPSP 170        180        190        200
RPAGQFQTLV VGVVGGLLGS LVLLVWVLAV ICSRAARGTI 210        220        230        240
GARRTGQPLK EDPSAVPVFS VDYGELDFQW REKTPEPPVP 250        260        270        280
CVPEQTEYAT IVFPSGMGTS SPARRGSADG PRSAQPLRPE

DGHCSWPL
```

PD-1 is a single-pass type I membrane protein. Four topological domains are known in human PD-1: a signal peptide corresponding to residues 1-20, an extracellular domain corresponding to residues 21-170, a transmembrane domain corresponding to residues 171-191, and a cytoplasmic domain corresponding to residues 192-288. A natural A215V variant occurs. In addition, two curated sequence conflicts (S38F and P162S) are known. In an embodiment of the invention, the amino acid sequence of cynomolgous monkey, e.g., *Macaca fascicularis* PD-1 (Swiss Prot entry B0LAJ3) comprises the following amino acid sequence (SEQ ID NO: 12):

```
        10         20         30         40
MQIPQAPWPV VWAVLQLGWR PGWFLESPDR PWNAPTFSPA 50         60         70         80
LLLVTEGDNA TFTCSFSNAS ESFVLNWYRM SPSNQTDKLA 90        100        110        120
AFPEDRSQPG QDCRFRVTRL PNGRDFHMSV VRARRNDSGT 130        140        150        160
YLCGAISLAP KAQIKESLRA ELRVTERRAE VPTAHPSPSP 170        180        190        200
RPAGQFQALV VGVVGGLLGS LVLLVWVLAV ICSRAAQGTI 210        220        230        240
EARRTGQPLK EDPSAVPVFS VDYGELDFQW REKTPEPPAP
```

```
       250        260        270        280
CVPEQTEYAT IVFPSGLGTS SPARRGSADG PRSPRPLRPE

DGHCSWPL
```

Anti-PD-1 Antibodies and Antigen-Binding Fragments Thereof

The present invention provides antibodies or antigen-binding fragments thereof that bind human PD-1, nucleic acids encoding such antibodies or antigen-binding fragments, and uses of such nucleic acids, antibodies or fragments. In some embodiments, the anti-PD-1 antibodies or their encoding nucleic acids are isolated. The present invention includes humanized anti-PD-1 antibodies and methods of use thereof.

As described above, anti-PD-1 antibodies and antigen binding fragments thereof of the present invention may be described structurally as comprising one or more, and optionally each, of:
a heavy chain variable region CDR1 comprising the amino acid sequence of SEQ ID NO: 1 or an amino acid sequence differing from SEQ ID NO: 1 by 1, 2, 3, or more conservative substitutions,
a heavy chain variable region CDR2 comprising the amino acid sequence of SEQ ID NO: 2 or an amino acid sequence differing from SEQ ID NO: 2 by 1, 2, 3, or more conservative substitutions,
a heavy chain variable region CDR3 comprising the amino acid sequence of SEQ ID NO: 3 or an amino acid sequence differing from SEQ ID NO: 3 by 1, 2, 3, or more conservative substitutions,
a light chain variable region CDR1 comprising the amino acid sequence of SEQ ID NO: 4 or an amino acid sequence differing from SEQ ID NO: 4 by 1, 2, 3, or more conservative substitutions,
a light chain variable region CDR2 comprising the amino acid sequence of SEQ ID NO: 5 or an amino acid sequence differing from SEQ ID NO: 5 by 1, 2, 3, or more conservative substitutions, and
a light chain variable region CDR3 comprising the amino acid sequence of SEQ ID NO: 6 or an amino acid sequence differing from SEQ ID NO: 6 by 1, 2, 3, or more conservative substitutions.

In certain preferred embodiments, such antibodies or antigen binding fragments comprise
a heavy chain sequence comprising the amino acid sequence of SEQ ID NO: 1 or an amino acid sequence differing from SEQ ID NO: 1 by 1, 2, 3, or more conservative substitutions; the amino acid sequence of SEQ ID NO: 2 or an amino acid sequence differing from SEQ ID NO: 2 by 1, 2, 3, or more conservative substitutions; and/or the amino acid sequence of SEQ ID NO: 3 or an amino acid sequence differing from SEQ ID NO: 3 by 1, 2, 3, or more conservative substitutions; and/or
a light chain sequence comprising the amino acid sequence of SEQ ID NO: 4 or an amino acid sequence differing from SEQ ID NO: 4 by 1, 2, 3, or more conservative substitutions; the amino acid sequence of SEQ ID NO: 5 or an amino acid sequence differing from SEQ ID NO: 5 by 1, 2, 3, or more conservative substitutions; and/or the amino acid sequence of SEQ ID NO: 6 or an amino acid sequence differing from SEQ ID NO: 6 by 1, 2, 3, or more conservative substitutions.

In still more preferred embodiments, such antibodies or antigen binding fragments comprise
a heavy chain variable region sequence comprising the amino acid sequence of SEQ ID NO: 7 or an amino acid sequence at least 90%, 95%, 97%, 98%, or 99% identical thereto; and a light chain variable region sequence comprising the amino acid sequence of SEQ ID NO:8 or an amino acid sequence at least 90%, 95%, 97%, 98%, or 99% identical thereto.

In certain of these embodiments, SEQ ID NO: 7 comprises one or more mutations at residue A9, K12, I28, T30, T31, and Y32, such as A9P, K12V, I28D, I28T, T30D, T31D, T31S, Y32D, and combinations thereof.

And in certain most preferred embodiments, such antibodies or antigen binding fragments comprise (i) a heavy chain sequence comprising an amino acid sequence selected from the group consisting of SEQ ID NO: 7, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48; and (ii) a light chain sequence comprising the amino acid sequence of SEQ ID NO: 8.

In still other preferred embodiments, such antibodies or antigen binding fragments comprise
a heavy chain variable region sequence comprising the amino acid sequence of SEQ ID NO: 31 or an amino acid sequence at least 90%, 95%, 97%, 98%, or 99% identical thereto; and a light chain variable region sequence comprising the amino acid sequence of SEQ ID NO: 33 or an amino acid sequence at least 90%, 95%, 97%, 98%, or 99% identical thereto.

And in certain most preferred embodiments, such antibodies or antigen binding fragments comprise a heavy chain sequence comprising the amino acid sequence of SEQ ID NO: 31 and a light chain sequence comprising the amino acid sequence of SEQ ID NO: 33.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the $V_L$, $V_H$, $C_L$ and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Single chain antibodies are also included by reference in the term "antibody."

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of

*Sequences of Proteins of Immunological Interest*, Kabat, et al.; National Institutes of Health, Bethesda, Md.; 5$^{th}$ ed.; NIH Publ. No. 91-3242 (1991); Kabat (1978) *Adv. Prot. Chem.* 32:1-75; Kabat, et al., (1977) *J. Biol. Chem.* 252: 6609-6616; Chothia, et al., (1987) *J Mol. Biol.* 196:901-917 or Chothia, et al., (1989) *Nature* 342:878-883.

As used herein, the term "hypervariable region" refers to the amino acid residues of an antibody or antigen-binding fragment thereof that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

IgG is the preferred class for therapeutic antibodies for several practical reasons. IgG antibodies are stable, easily purified, and able to be stored under conditions that are practical for pharmaceutical supply chains. In vivo they have a long biological half-life that is not just a function of their size but is also a result of their interaction with the so-called Fc receptor (or FcRn). This receptor seems to protect IgG from catabolism within cells and recycles it back to the plasma.

An antibody or binding fragment thereof of the present invention specifically binds PD-1. The term "specifically binds" is not intended to indicate that an antibody binds exclusively to its intended target since an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ M$^{-1}$, and preferably between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{12}$ M$^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

Antibodies of the invention may be further characterized by epitope mapping, so that antibodies and epitopes may be selected that have the greatest clinical utility in the immunoassays described herein. The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Preferably, an epitope is targeted which is present on the target molecule, but is partially or totally absent on non-target molecules.

In some embodiments, the antibody scaffold can be a mixture of sequences from different species. As such, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239:1534-1536. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, Nature 321:522-525; Riechmann et al., 1988; Nature 332: 323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. patent Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve the grafting of only parts of the CDRs, including but not limited to methods described in U.S. patent Ser. No. 09/810,502; Tan et al., 2002, J. Immunol. 169:1119-1125; De Pascalis et al., 2002, J. Immunol. 169:3076-3084.

In one embodiment, the antibody is a fully human antibody. "Fully human antibody" or "complete human antibody" refers to a human antibody having the gene sequence of an antibody derived from a human chromosome. Fully human antibodies may be obtained, for example, using transgenic mice (Bruggemann et al., 1997, Curr Opin Biotechnol 8:455-458) or human antibody libraries coupled with selection methods (Griffiths et al., 1998, Curr Opin Biotechnol 9:102-108).

The present invention includes anti-PD-1 antigen-binding fragments and methods of use thereof. As used herein, unless otherwise indicated, "antibody fragment" or "antigen-binding fragment" refers to antigen-binding fragments of antibodies, i.e. antibody fragments that retain the ability to bind specifically to the antigen bound by the full-length antibody, e.g. fragments that retain one or more CDR regions. Examples of antigen-binding fragments include, but are not limited to, Fab, Fab', F(ab')$_2$, and Fv fragments; diabodies; linear antibodies; single-chain antibody molecules, e.g., sc-Fv; nanobodies; and multispecific antibodies formed from antibody fragments (e.g., bispecific antibodies, etc.).

The present invention includes anti-PD-1 Fab fragments and methods of use thereof. A "Fab fragment" is comprised of one light chain and the $C_H1$ and variable regions of one heavy chain. The heavy chain of a Fab molecule cannot form a disulfide bond with another heavy chain molecule. An "Fab fragment" can be the product of papain cleavage of an antibody.

The present invention includes anti-PD-1 antibodies and antigen-binding fragments thereof which comprise an Fc region and methods of use thereof. An "Fc" region contains two heavy chain fragments comprising the CH1 and CH2 domains of an antibody. The two heavy chain fragments are held together by two or more disulfide bonds and by hydrophobic interactions of the CH3 domains.

The present invention includes anti-PD-1 Fab' fragments and methods of use thereof. A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

The present invention includes anti-PD-1 F(ab')$_2$ fragments and methods of use thereof. A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains. A "F(ab')$_2$ fragment" can be the product of pepsin cleavage of an antibody.

The present invention includes anti-PD-1 Fv fragments and methods of use thereof. The "Fv region" comprises the variable regions from both the heavy and light chains, but lacks the constant regions.

The present invention includes anti-PD-1 scFv fragments and methods of use thereof. The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

The present invention includes anti-PD-1 domain antibodies and methods of use thereof. A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The present invention includes anti-PD-1 bivalent antibodies and methods of use thereof. A "bivalent antibody" comprises two antigen-binding sites. In some instances, the two binding sites have the same antigen specificities. However, bivalent antibodies may be bispecific (see below).

The present invention includes anti-PD-1 camelized single domain antibodies and methods of use thereof. In certain embodiments, antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

The present invention includes anti-PD-1 diabodies and methods of use thereof. As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

Typically, an antibody or antigen-binding fragment of the invention which is modified in some way retains at least 10% of its binding affinity (when compared to the parental antibody) when that activity is expressed on a molar basis. Preferably, an antibody or antigen-binding fragment of the invention retains at least 20%, 50%, 70%, 80%, 90%, 95% or 100% or more of the PD-1 binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention includes isolated anti-PD-1 antibodies and antigen-binding fragments thereof and methods of use thereof. "Isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The present invention includes anti-PD-1 chimeric antibodies (e.g., human constant domain/mouse variable domain) and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., (1984) *Proc. Natl. Acad. Sci. USA* 81: 6851-6855). Typically, the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g., mouse) antibody.

Production of Anti-PD-1 Antibodies

Monoclonal antibody preparations can be produced using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Monoclonal antibodies derived from animals other than rats and mice offer unique advantages. Many protein targets relevant to signal transduction and disease are highly conserved between mice, rats and humans, and can therefore be recognized as self-antigens by a mouse or rat host, making them less immunogenic. This problem may be avoided when using rabbit as a host animal. See, e.g., Rossi et al., *Am. J. Clin. Pathol.*, 124, 295-302, 2005.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Adjuvants that can be used in the methods of antibody generation include, but are not limited to, protein adjuvants; bacterial adjuvants, e.g., whole bacteria (BCG, *Corynebacterium parvum, Salmonella minnesota*) and bacterial components including cell wall skeleton, trehalose dimycolate, monophosphoryl lipid A, methanol extractable residue (MER) of tubercle bacillus, complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used in the methods of the invention include, Cholera toxin, paropox proteins, MF-59 (Chiron Corporation; See also Bieg et al. (1999) "GAD65 And Insulin B Chain Peptide (9-23) Are Not Primary Autoantigens In The Type 1 Diabetes Syndrome Of The BB Rat," Autoimmunity, 31(1):15-24, which is incorporated herein by reference), MPL® (Corixa Corporation; See also Lodmell et al. (2000) "DNA Vaccination Of Mice Against Rabies Virus: Effects Of The Route Of Vaccination And The Adjuvant Monophosphoryl Lipid A (MPL)," Vaccine, 18: 1059-1066; Johnson et al. (1999) "3-O-Desacyl Monophosphoryl Lipid A Derivatives: Synthesis And Immunostimulant Activities," Journal of Medicinal Chemistry, 42: 4640-4649; Baldridge et al. (1999) "Monophosphoryl Lipid A (MPL) Formulations For The Next Generation Of Vaccines," Methods, 19: 103-107, all of which are incorporated herein by reference), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al. (1998) "Active Immunotherapy With Ultraviolet B-Irradiated Autologous Whole Melanoma Cells Plus DETOX In Patients With Metastatic Melanoma," Clin. Cancer Res. 4(3):619-627; and Gupta et al. (1995) "Adjuvants For Human Vaccines—Current Status, Problems And Future Prospects," Vaccine, 13(14): 1263-1276, both of which are incorporated herein by reference).

Numerous publications discuss the use of phage display technology to produce and screen libraries of polypeptides for binding to a selected analyte. See, e.g, Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phages displaying a polypeptide with affinity to a target bind to the target and these phages are enriched by affinity screening to the target. The identity of polypeptides displayed from these phages can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. (1995) "Human Antibodies From Transgenic Mice," Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix/Amgen (Freemont, Calif.) and Medarex/BMS (Princeton, N.J.), Kymab (Cambridge, UK) and Merus (Utrecht, Netherlands) can be engaged to provide human antibodies directed against a selected antigen using technology similar to that described above.

Recombinant Expression of Anti-PD-1 Antibodies

Once a nucleic acid sequence encoding an antibody of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. (See, for example, the techniques described in Sambrook et al, 1990, MOLECULAR CLONING, A LABORATORY MANUAL, 2d Ed., Cold Spring Harbor Laboratory, Cold Spring Harbor, N.Y. and Ausubel et al. eds., 1998, CURRENT PROTOCOLS IN MOLECULAR BIOLOGY, John Wiley & Sons, NY).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The anti-PD-1 antibodies disclosed herein may also be produced recombinantly (e.g., in an *E. coli*/T7 expression system, a mammalian cell expression system or a lower eukaryote expression system). In this embodiment, nucleic acids encoding the antibody immunoglobulin molecules of the invention (e.g., $V_H$ or $V_L$) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as a *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside).

Thus, the present invention includes recombinant methods for making an anti-PD-1 antibody or antigen-binding fragment thereof of the present invention, or an immunoglobulin chain thereof, comprising introducing a polynucleotide encoding one or more immunoglobulin chains of the antibody or fragment (e.g., heavy and/or light immunoglobulin chain); culturing the host cell (e.g., CHO or *Pichia* or *Pichia pastoris*) under condition favorable to such expression and, optionally, isolating the antibody or fragment or chain from the host cell and/or medium in which the host cell is grown.

Anti-PD-1 antibodies can also be synthesized by any of the methods set forth in U.S. Pat. No. 6,331,415.

Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any *Aspergillus* sp., *Trichoderma reesei, Chrysosporium lucknowense*, any *Fusarium* sp., *Yarrowia lipolytica*, and *Neurospora crassa*. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody or fragment or chain in the host cells or secretion of the into the culture medium in which the host cells are grown.

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CμMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807, 715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Ruther et al. (1983) "Easy Identification Of cDNA Clones," EMBO J. 2:1791-1794), in which the antibody coding sequence may be ligated individually into the vector in frame with the lac Z coding region so that a fusion protein is produced; pIN vectors (Inouye et al. (1985) "Up-Promoter Mutations In The Lpp Gene Of *Escherichia coli*," Nucleic Acids Res. 13:3101-3110; Van Heeke et al. (1989) "Expression Of Human Asparagine Synthetase In *Escherichia coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts. (see e.g., see Logan et al. (1984) "Adenovirus Tripartite Leader Sequence Enhances Translation Of mRNAs Late After Infection," Proc. Natl. Acad. Sci. (U.S.A.) 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11:223-232), hypoxanthine-guanine phosphoribosyltransferase (Szybalska et al. (1962) "Genetics Of Human Cess Line. IV. DNA-Mediated Heritable Transformation Of A Biochemical Trait," Proc. Natl. Acad. Sci. (U.S.A.) 48:2026-2034), and adenine phosphoribosyltransferase (Lowy et al. (1980) "Isolation Of Transforming DNA: Cloning The Hamster Aprt Gene," Cell 22:817-823) genes can be employed in tk−, hgprt− or aprt− cells, respectively. Also, antimetabolite resistance can be used as the basis of selection for the following genes: dhfr, which confers resistance to methotrexate (Wigler et al. (1980) "Transformation Of Mammalian Cells With An Amplfiable Dominant-Acting Gene," Proc. Natl. Acad. Sci. (U.S.A.) 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. (U.S.A.) 78:1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. (U.S.A.) 78:2072-2076); neo, which confers resistance to the aminoglycoside G-418 (Tachibana et al. (1991) "Altered Reactivity Of Immunoglobutin Produced By Human-Human Hybridoma Cells Transfected By pSV2-Neo Gene," Cytotechnology 6(3):219-226; Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human gene therapy," Ann. Rev. Biochem. 62:191-217). Methods commonly known in the art of recombinant DNA technology which can be used are described in Ausubel et al. (eds.), 1993, CURRENT PROTOCOLS IN MOLECULAR BIOLOGY, John Wiley & Sons, NY; Kriegler, 1990, GENE TRANSFER AND EXPRESSION, A LABORATORY MANUAL, Stockton Press, NY; and in Chapters 12 and 13, Dracopoli et al. (eds), 1994, CURRENT PROTOCOLS IN HUMAN GENETICS, John Wiley & Sons, NY.; Colbere-Garapin et al. (1981) "A New Dominant Hybrid Selective Marker For Higher Eukaryotic Cells," J. Mol. Biol. 150:1-14; and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156).

The expression levels of an antibody of the invention can be increased by vector amplification (for a review, see Bebbington and Hentschel, "The Use Of Vectors Based On Gene Amplification For The Expression Of Cloned Genes In Mammaian Cells," in DNA CLONING, Vol. 3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al. (1983) "Expression And Amplification Of Engineered Mouse Dihydrofolate Reductase Minigenes," Mol. Cell. Biol. 3:257-266).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot (1986) "Expression And Amplification Of Engineered Mouse Dihydrofolate Reductase Minigenes," Nature 322:562-565; Kohler (1980) "Immunoglobulin Chain Loss In Hybridoma Lines," Proc. Natl. Acad. Sci. (U.S.A.) 77:2197-2199). The coding sequences for the heavy and light chains may comprise cDNA or genomic DNA.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., *J. Biol. Chem.* 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

Physical and Functional Properties of Exemplary Anti-PD-1 Antibodies

An "anti-PD-1 antibody or antigen-binding fragment thereof of the present invention" includes: any antibody or antigen-binding fragment thereof that is discussed herein (e.g., hPD-1.29A) or humanized versions thereof (e.g., hPD1.29H5L4) or a variant thereof (e.g., sequence variant or functional variant); any antibody or antigen-binding fragment comprising any one or more of the CDRs set forth in SEQ ID NOS: 1-6.

Antibodies and fragments that bind to the same epitope as any of the anti-PD-1 antibodies or antigen-binding fragments thereof of the present invention also form part of the present invention. There are several methods available for mapping antibody epitopes on target antigens, including: cross-competition assays (in ELISA format or in a BioLayer Interferometry setup), domain swaps where mouse and human PD-1 domains are exchanged, point mutants (Alanine scan; mouse/human single point mutants) and peptide arrays (covering the full protein with a number of amino acids overlap between peptides). Other methods to map epitope of the antibody include but are not limited to: H/D-Ex Mass spectrometry, X-ray crystallography, NMR and peptide library scanning.

In other embodiments, the invention provides antibodies or antigen-binding fragment thereof that binds human PD-1 (e.g., humanized antibodies) and has $V_L$ domains and $V_H$ domains with at least 90%, 95%, 96%, 97%, 98% or 99% sequence identity with SEQ ID NOS: 7 and 8. In other embodiments, the invention provides antibodies or antigen-binding fragment thereof that bind human PD-1 (e.g., humanized antibodies) and have a $V_L$ domain having at least 95% sequence identity with one of SEQ ID NOs: 8, 18, 19, 20, or 33; together with a $V_H$ domain having at least 95% sequence identity with one of SEQ ID NOs: 7, 14, 15, 16, 17, or 31.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 2.

TABLE 2

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 2. Also provided are isolated polypeptides comprising the $V_L$ domains of the anti-PD-1 antibodies of the invention (e.g., SEQ ID NOs: 8, 18, 19, 20, or 33), and isolated polypeptides comprising the $V_H$ domains of the anti-PD-1 antibodies of the invention (e.g., SEQ ID NOs: 7, 14, 15, 16, 17, or 31), in each case having up to 0, 1, 2, 3, 4, 5, 6, 7, 8, 9, 10 or more conservative amino acid substitutions.

In another embodiment, provided is an antibody or antigen-binding fragment thereof that binds PD-1 and has $V_L$ domains and $V_H$ domains with at least 99% 98%, 97%, 96%, 95%, 90%, 85%, 80% or 75% sequence identity to one or more of the $V_L$ domains or $V_H$ domains described herein, and exhibits specific binding to PD-1. In another embodiment the binding antibody or antigen-binding fragment thereof of the present invention comprises $V_L$ and $V_H$ domains (with and without signal sequence) having up to 0, 1, 2, 3, 4, 5, 6, 7, 8, 9, 10, 11, 12, 13, 14, 15, 16, 17, 18, 19, 20, 21, 22, 23, 24, 25 or more amino acid substitutions, and exhibits specific binding to PD-1.

Polynucleotides and Polypeptides

The present invention further comprises the polynucleotides encoding any of the polypeptides or immunoglobulin chains of anti-PD-1 antibodies and antigen-binding fragments thereof of the invention. For example, the present invention includes the polynucleotides encoding the amino acids described in any one of SEQ ID NOs: 1-8.

In one embodiment, an isolated polynucleotide, for example DNA, encoding the polypeptide chains of the isolated antibodies or antigen-binding fragments set forth herein is provided. In one embodiment, the isolated polynucleotide encodes an antibody or antigen-binding fragment thereof comprising at least one mature immunoglobulin light chain variable ($V_L$) domain according to the invention and/or at least one mature immunoglobulin heavy chain variable (V$_H$) domain according to the invention. In some embodiments the isolated polynucleotide encodes both a light chain and a heavy chain on a single polynucleotide molecule, and in other embodiments the light and heavy chains are encoded on separate polynucleotide molecules. In another embodiment the polynucleotides further encodes a signal sequence.

In one embodiment, the invention comprises an isolated polynucleotide encoding one or more of the CDR domains set forth in SEQ ID NOS: 1-6.

In one embodiment, the invention comprises an isolated polynucleotide encoding the immunoglobulin heavy chain variable region sequence of SEQ ID NO: 7, preferably SEQ ID NO: 9, or an isolated polynucleotide that encodes an immunoglobulin heavy chain variable region sequence selected from the group consisting of SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48.

In one embodiment, the invention comprises an isolated polynucleotide encoding the immunoglobulin light chain variable region sequence of SEQ ID NO: 8, preferably SEQ ID NO: 10.

This present invention also provides vectors, e.g., expression vectors, such as plasmids, comprising the isolated polynucleotides of the invention, wherein the polynucleotide is operably linked to control sequences that are recognized by a host cell when the host cell is transfected with the vector. Also provided are host cells comprising a vector of the present invention and methods for producing the antibody or antigen-binding fragment thereof or polypeptide disclosed herein comprising culturing a host cell harboring an expression vector or a nucleic acid encoding the immunoglobulin chains of the antibody or antigen-binding fragment thereof in culture medium, and isolating the antigen or antigen-binding fragment thereof from the host cell or culture medium.

Also included in the present invention are polypeptides, e.g., immunoglobulin polypeptides, comprising amino acid sequences that are at least about 75% identical, 80% identical, more preferably at least about 90% identical and most preferably at least about 95% identical (e.g., 95%, 96%, 97%, 98%, 99%, 100%) to the amino acid sequences of the antibodies provided herein when the comparison is performed by a BLAST algorithm wherein the parameters of the algorithm are selected to give the largest match between the respective sequences over the entire length of the respective reference sequences (e.g. expect threshold: 10; word size: 3; max matches in a query range: 0; BLOSUM 62 matrix; gap costs: existence 11, extension 1; conditional compositional score matrix adjustment).

Sequence identity refers to the degree to which the amino acids of two polypeptides are the same at equivalent positions when the two sequences are optimally aligned.

The following references relate to BLAST algorithms often used for sequence analysis: BLAST ALGORITHMS: Altschul et al. (2005) *FEBS J.* 272(20): 5101-5109; Altschul, S. F., et al., (1990) *J. Mol. Biol.* 215:403-410; Gish, W., et al., (1993) *Nature Genet.* 3:266-272; Madden, T. L., et al., (1996) *Meth. Enzymol.* 266:131-141; Altschul, S. F., et al., (1997) *Nucleic Acids Res.* 25:3389-3402; Zhang, J., et al., (1997) *Genome Res.* 7:649-656; Wootton, J. C., et al., (1993) *Comput. Chem.* 17:149-163; Hancock, J. M., et al., (1994) *Comput. Appl. Biosci.* 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, *Natl. Biomed. Res. Found.*, Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, *Natl. Biomed. Res. Found.*, Washington, D.C.; Altschul, S. F., (1991) J. Mol. Biol. 219:555-565; States, D. J., et al., (1991) *Methods* 3:66-70; Henikoff, S., et al., (1992) *Proc. Natl. Acad. Sci. USA* 89:10915-10919; Altschul, S. F., et al., (1993) J. Mol. Evol. 36:290-300; ALIGNMENT STATISTICS: Karlin, S., et al., (1990) *Proc. Natl. Acad. Sci. USA* 87:2264-2268; Karlin, S., et al., (1993) *Proc. Natl. Acad. Sci. USA* 90:5873-5877; Dembo, A., et al., (1994) *Ann. Prob.* 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

Ability of Anti-PD-1 Antibodies to Block PD-1 Binding to PD-L1/PD-L2

In some embodiments, the anti-PD-1 antibodies or antigen binding fragments of the invention are able to block binding of human PD-1 to human PD-L1 and/or PD-L2. The ability to block binding of human PD-1 to human PD-L1/PD-L2 can be determined using any method known in the art. In one embodiment, the ability of the antibodies to block binding of human PD-1 to human PD-L1/PD-L2 is determined using an ELISA assay.

Antibody Engineering

Further included are embodiments in which the anti-PD-1 antibodies and antigen-binding fragments thereof are engineered antibodies to include modifications to framework residues within the variable domains of the parental hPD-1.29A monoclonal antibody, e.g. to improve the properties of the antibody or fragment. Typically, such framework modifications are made to decrease the immunogenicity of the antibody or fragment. This is usually accomplished by replacing non-CDR residues in the variable domains (i.e. framework residues) in a parental (e.g. rodent) antibody or fragment with analogous residues from the immune repertoire of the species in which the antibody is to be used, e.g. human residues in the case of human therapeutics. Such an antibody or fragment is referred to as a "humanized" antibody or fragment. In some cases it is desirable to increase the affinity, or alter the specificity of an engineered (e.g. humanized) antibody. One approach is to "backmutate" one or more framework residues to the corresponding germline sequence. More specifically, an antibody or fragment that has undergone somatic mutation can contain framework residues that differ from the germline sequence from which the antibody is derived. Such residues can be identified by comparing the antibody or fragment framework sequences to the germline sequences from which the antibody or fragment is derived. Another approach is to revert to the original parental (e.g., rodent) residue at one or more positions of the engineered (e.g. humanized) antibody, e.g. to restore binding affinity that may have been lost in the process of replacing the framework residues. (See, e.g., U.S. Pat. Nos. 5,693,762, 5,585,089 and 5,530,101.)

In certain embodiments, the anti-PD-1 antibodies and antigen-binding fragments thereof are engineered (e.g. humanized) to include modifications to in the framework and/or CDRs to improve their properties. Such engineered changes can be based on molecular modelling. A molecular model for the variable region for the parental (non-human) antibody sequence can be constructed to understand the structural features of the antibody and used to identify potential regions on the antibody that can interact with the antigen. Conventional CDRs are based on alignment of immunoglobulin sequences and identifying variable regions. Kabat et al., (1991) *Sequences of Proteins of Immunological Interest*, Kabat, et al.; National Institutes of Health, Bethesda, Md.; 5$^{th}$ ed.; NIH Publ. No. 91-3242; Kabat (1978) *Adv. Prot. Chem.* 32:1-75; Kabat, et al., (1977) *J. Biol. Chem.* 252:6609-6616. Chothia and coworkers carefully examined conformations of the loops in crystal structures of antibodies and proposed hypervariable loops. Chothia, et al., (1987) *J Mol. Biol.* 196:901-917 or Chothia, et al., (1989) *Nature* 342:878-883. There are variations between regions classified as "CDRs" and "hypervariable loops". Later studies (Raghunathan et al, (2012) *J. Mol Recog.* 25, 3, 103-113) analyzed several antibody-antigen crystal complexes and observed that the antigen binding regions in antibodies do not necessarily conform strictly to the "CDR" residues or "hypervariable" loops. The molecular model for the variable region of the non-human antibody can be used to guide the selection of regions that can potentially bind to the antigen. In practice the potential antigen binding regions based on model differ from the conventional "CDR"s or "hyper variable" loops. Commercial scientific software such as Discovery Studio (Dassault Systèmes BIOVIA) can be used for molecular modeling. Human frameworks can be selected based on best matches with the non-human sequence both in the frameworks and in the CDRs. For FR4 (framework 4) in $V_H$, $V_J$ regions for the human germlines are compared with the corresponding non-human region. In the case of FR4 (framework 4) in $V_L$, J-kappa and J-Lambda regions of human germline sequences are compared with the corresponding non-human region. Once suitable human frameworks are identified, the CDRs are grafted into the selected human frameworks. In some cases certain residues in the $V_L$-$V_H$ interface can be retained as in the non-human (parental) sequence. Molecular models can also be used for identifying residues that can potentially alter the CDR conformations and hence binding to antigen. In some cases, these residues are retained as in the non-human (parental) sequence. Molecular models can also be used to identify solvent exposed amino acids that can result in unwanted effects such as glycosylation, deamidation and oxidation. Developability filters can be introduced early on in the design stage to eliminate/minimize these potential problems.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antibody, so as to avoid deamidation or isomerization. The deamidation of asparagine may occur on NG, DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain embodiments, the antibodies of the present disclosure do not contain deamidation or asparagine isomerism sites.

For example, an asparagine (Asn) residue may be changed to Gln or Ala to reduce the potential for formation of isoaspartate at any Asn-Gly sequences, particularly within a CDR. A similar problem may occur at a Asp-Gly sequence. Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs may be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for PD-1, or other desired biological activity to unacceptable levels.

TABLE 3

Exemplary stabilizing CDR variants

| CDR Residue | Stabilizing Variant Sequence |
| --- | --- |
| Asn-Gly | Gln-Gly, Ala-Gly, or Asn-Ala |
| (N-G) | (Q-G), (A-G), or (N-A) |
| Asp-Gly | Glu-Gly, Ala-Gly or Asp-Ala |
| (D-G) | (E-G), (A-G), or (D-A) |
| Met (typically solvent exposed) | Lys, Leu, Ala, or Phe |
| (M) | (K), (L), (A), or (F) |
| Asn | Gln or Ala |
| (N) | (Q) or (A) |
| Asn-Pro | Gln-Pro, Ala-Pro, or Asn-Ala |
| (N-P) | (Q-P), (A-P), or (N-A) |

Antibody Engineering of the Fc Region

The antibodies (e.g., humanized antibodies) and antigen-binding fragments thereof disclosed herein can also be engineered to include modifications within the Fc region, typically to alter one or more properties of the antibody, such as serum half-life, complement fixation, Fc receptor binding, and/or effector function (e.g., antigen-dependent cellular cytotoxicity). Furthermore, the antibodies and antigen-binding fragments thereof disclosed herein can be chemically modified (e.g., one or more chemical moieties can be attached to the antibody) or be modified to alter its glycosylation, again to alter one or more properties of the antibody or fragment. Each of these embodiments is described in further detail below. The numbering of residues in the Fc region is that of the EU index of Kabat.

The antibodies and antigen-binding fragments thereof disclosed herein also include antibodies and fragments with modified (or blocked) Fc regions to provide altered effector functions. See, e.g., U.S. Pat. No. 5,624,821; WO2003/086310; WO2005/120571; WO2006/0057702. Such modifications can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc regions. Changes to the Fc can also alter the half-life of antibodies in therapeutic antibodies, enabling less frequent dosing and thus increased convenience and decreased use of material. See Presta (2005) J. Allergy Clin. Immunol. 116: 731 at 734-35.

In one embodiment, the antibody or antigen-binding fragment of the invention is an IgG4 isotype antibody or fragment comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. (1993) Mol. Immunol. 30:105-108; position 241 is based on the Kabat numbering system).

In one embodiment of the invention, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the Fc hinge region of an antibody or antigen-binding fragment of the invention is mutated to decrease the biological half-life of the antibody or fragment. More specifically, one or more amino acid mutations are introduced into the CH2-CH3 domain interface region of the Fc-hinge fragment such that the antibody or fragment has impaired Staphylococcyl protein A (SpA) binding relative to native Fc-hinge domain SpA binding. This approach is described in further detail in U.S. Pat. No. 6,165,745.

In another embodiment, the antibody or antigen-binding fragment of the invention is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody or antigen-binding fragment. For example, one or more amino acids selected from amino acid residues 234, 235, 236, 237, 297, 318, 320 and 322 can be replaced with a different amino acid residue such that the antibody has an altered affinity for an effector ligand and retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to decrease the ability of the antibody or antigen-binding fragment of the invention to mediate antibody dependent cellular cytotoxicity (ADCC) and/or to decrease the affinity of the antibody or fragment for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) J. Biol. Chem. 276:6591-6604).

In one embodiment of the invention, the Fc region is modified to decrease the ability of the antibody of the invention to mediate effector function and/or to increase anti-inflammatory properties by modifying residues 243 and 264. In one embodiment, the Fc region of the antibody or fragment is modified by changing the residues at positions 243 and 264 to alanine. In one embodiment, the Fc region is modified to decrease the ability of the antibody or fragment to mediate effector function and/or to increase anti-inflammatory properties by modifying residues 243, 264, 267 and 328.

Production of Antibodies with Modified Glycosylation

In still another embodiment, the antibodies or antigen-binding fragments of the invention comprise a particular glycosylation pattern. For example, an afucosylated or an aglycosylated antibody or fragment can be made (i.e., the antibody lacks fucose or glycosylation, respectively). The glycosylation pattern of an antibody or fragment may be altered to, for example, increase the affinity or avidity of the antibody or fragment for a PD-1 antigen. Such modifications can be accomplished by, for example, altering one or more of the glycosylation sites within the antibody or fragment sequence. For example, one or more amino acid substitutions can be made that result in the removal of one or more of the variable region framework glycosylation sites to thereby eliminate glycosylation at that site. Such aglycosylation may increase the affinity or avidity of the antibody or fragment for antigen. See, e.g., U.S. Pat. Nos. 5,714,350 and 6,350,861.

Antibodies and antigen-binding fragments disclosed herein may further include those produced in lower eukaryote host cells, in particular fungal host cells such as yeast and filamentous fungi have been genetically engineered to produce glycoproteins that have mammalian- or human-like glycosylation patterns (See for example, Choi et al, (2003) Proc. Natl. Acad. Sci. 100: 5022-5027; Hamilton et al., (2003) Science 301: 1244-1246; Hamilton et al., (2006) Science 313: 1441-1443; Nett et al., Yeast 28(3):237-52 (2011); Hamilton et al., Curr Opin Biotechnol. October; 18(5):387-92 (2007)). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures (See for example, Li et al., (2006) *Nat. Biotechnol.* 24: 210-215).

In particular embodiments, the antibodies and antigen-binding fragments thereof disclosed herein further include those produced in lower eukaryotic host cells and which comprise fucosylated and non-fucosylated hybrid and complex N-glycans, including bisected and multiantennary species, including but not limited to N-glycans such as GlcNAc$_{(1-4)}$Man$_3$GlcNAc$_2$; Gal$_{(1-4)}$GlcNAc$_{(1-4)}$Man$_3$GlcNAc$_2$; NANA$_{(1-4)}$Gal$_{(1-4)}$GlcNAc$_{(1-4)}$Man$_3$GlcNAc$_2$.

In particular embodiments, the antibodies and antigen-binding fragments thereof provided herein may comprise antibodies or fragments having at least one hybrid N-glycan selected from the group consisting of GlcNAcMan$_5$GlcNAc$_2$; GalGlcNAcMan$_5$GlcNAc$_2$; and NANAGalGlcNAcMan$_5$GlcNAc$_2$. In particular aspects, the hybrid N-glycan is the predominant N-glycan species in the composition.

In particular embodiments, the antibodies and antigen-binding fragments thereof provided herein comprise antibodies and fragments having at least one complex N-glycan selected from the group consisting of GlcNAcMan$_3$GlcNAc$_2$; GalGlcNAcMan$_3$GlcNAc$_2$; NANAGalGlcNAcMan$_3$GlcNAc$_2$; GlcNAc$_2$Man$_3$GlcNAc$_2$; GalGlcNAc$_2$Man$_3$GlcNAc$_2$; Gal$_2$GlcNAc$_2$Man$_3$GlcNAc$_2$; NANAGal$_2$GlcNAc$_2$Man$_3$GlcNAc$_2$; and NANA$_2$Gal$_2$GlcNAc$_2$Man$_3$GlcNAc$_2$. In particular aspects, the complex N-glycan are the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In one embodiment, the antibody and antigen binding fragments thereof provided herein comprise complex N-glycans, wherein at least 50%, 60%, 70%, 80%, 90%, 95%, 97%, 98%, 99%, or 100% of the complex N-glycans in comprise the structure NANA$_2$Gal$_2$GlcNAc$_2$Man$_3$GlcNAc$_2$, wherein such structure is afucosylated. Such structures can be produced, e.g., in engineered *Pichia pastoris* host cells.

In particular embodiments, the N-glycan is fucosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of Man$_5$GlcNAc$_2$(Fuc), GlcNAcMan$_5$GlcNAc$_2$(Fuc), Man$_3$GlcNAc$_2$(Fuc), GlcNAcMan$_3$GlcNAc$_2$(Fuc), GlcNAc$_2$Man$_3$GlcNAc$_2$(Fuc), GalGlcNAc$_2$Man$_3$GlcNAc$_2$(Fuc), Gal$_2$GlcNAc$_2$Man$_3$GlcNAc$_2$(Fuc), NANAGal$_2$GlcNAc$_2$Man$_3$GlcNAc$_2$(Fuc), and NANA$_2$Gal$_2$GlcNAc$_2$Man$_3$GlcNAc$_2$(Fuc); in an α1,3-linkage or α1,4-linkage fucose to produce a glycoform selected from the group consisting of GlcNAc(Fuc)Man$_5$GlcNAc$_2$, GlcNAc(Fuc)Man$_3$GlcNAc$_2$, GlcNAc$_2$(Fuc$_{1-2}$)Man$_3$GlcNAc$_2$, GalGlcNAc$_2$(Fuc$_{1-2}$)Man$_3$GlcNAc$_2$, Gal$_2$GlcNAc$_2$(Fuc$_{1-2}$)Man$_3$GlcNAc$_2$, NANAGal$_2$GlcNAc$_2$(Fuc$_{1-2}$)Man$_3$GlcNAc$_2$, and NANA$_2$Gal$_2$GlcNAc$_2$(Fuc$_{1-2}$)Man$_3$GlcNAc$_2$; or in an α1,2-linkage fucose to produce a glycoform selected from the group consisting of Gal(Fuc)GlcNAc$_2$Man$_3$GlcNAc$_2$, Gal$_2$(Fuc$_{1-2}$)GlcNAc$_2$Man$_3$GlcNAc$_2$, NANAGal$_2$(Fuc$_{1-2}$)GlcNAc$_2$Man$_3$GlcNAc$_2$, and NANA$_2$Gal$_2$(Fuc$_{1-2}$)GlcNAc$_2$Man$_3$GlcNAc$_2$.

In further aspects, the antibodies (e.g., humanized antibodies) or antigen-binding fragments thereof comprise high mannose N-glycans, including but not limited to, Man$_8$GlcNAc$_2$, Man$_7$GlcNAc$_2$, Man$_6$GlcNAc$_2$, Man$_5$GlcNAc$_2$, Man$_4$GlcNAc$_2$, or N-glycans that consist of the Man$_3$GlcNAc$_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs co-translationally in the lumen of the ER and continues post-translationally in the Golgi apparatus for N-linked glycoproteins.

N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the Man$_3$GlcNAc$_2$ ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as Man$_3$GlcNAc$_2$; the term "G-1" refers to an N-glycan structure that can be characterized as GlcNAcMan$_3$GlcNAc$_2$; the term "G0" refers to an N-glycan structure that can be characterized as GlcNAc$_2$Man$_3$GlcNAc$_2$; the term "G1" refers to an N-glycan structure that can be characterized as GalGlcNAc$_2$Man$_3$GlcNAc$_2$; the term "G2" refers to an N-glycan structure that can be characterized as Gal$_2$GlcNAc$_2$Man$_3$GlcNAc$_2$; the term "A1" refers to an N-glycan structure that can be characterized as NANAGal$_2$GlcNAc$_2$Man$_3$GlcNAc$_2$; and, the term "A2" refers to an N-glycan structure that can be characterized as NANA$_2$Gal$_2$GlcNAc$_2$Man$_3$GlcNAc$_2$. Unless otherwise indicated, the terms G-"2", "G-1", "G0", "GI", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas GlcNAc$_{(2-4)}$Man$_3$GlcNAc$_2$, Gal$_{(1-4)}$GlcNAc$_{(2-4)}$Man$_3$GlcNAc$_2$, or NANA$_{(1-4)}$Gal$_{(1-4)}$GlcNAc$_{(2-4)}$Man$_3$GlcNAc$_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula GlcNAc$_3$Man$_3$GlcNAc$_2$ wherein each mannose residue is linked at its non-reducing end to a GlcNAc residue. In contrast, when a multiantennary N-glycan is characterized as GlcNAc$_3$Man$_3$GlcNAc$_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Antibody Physical Properties

The antibodies and antigen-binding fragments thereof disclosed herein may further contain one or more glycosylation sites in either the light or heavy chain immunoglobulin variable region. Such glycosylation sites may result in increased immunogenicity of the antibody or fragment or an alteration of the pK of the antibody due to altered antigen-binding (Marshall et al. (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316: 452-7; Mimura et al. (2000) *Mol Immunol* 37:697-706). Glycosylation has been known to occur at motifs containing an N-X-S/T sequence.

Each antibody or antigen-binding fragment will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8.

Each antibody or antigen-binding fragment will have a characteristic melting temperature, with a higher melting temperature indicating greater overall stability in vivo (Krishnamurthy R and Manning M C (2002) *Curr Pharm Biotechnol* 3:361-71). In general, the T$_M$1 (the temperature of initial unfolding) may be greater than 60° C., greater than 65° C., or greater than 70° C. The melting point of an antibody or fragment can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a further embodiment, antibodies and antigen-binding fragments thereof are selected that do not degrade rapidly. Degradation of an antibody or fragment can be measured using capillary electrophoresis (CE) and MALDI-MS (Alexander A J and Hughes D E (1995) *Anal Chem* 67:3626-32).

In a further embodiment, antibodies and antigen-binding fragments thereof are selected that have minimal aggregation effects, which can lead to the triggering of an unwanted immune response and/or altered or unfavorable pharmacokinetic properties. Generally, antibodies and fragments are acceptable with aggregation of 25% or less, 20% or less, 15% or less, 10% or less, 5% or less, 1% or less, or 0.5% or less. Aggregation can be measured by several techniques, including size-exclusion chromatography (SEC), high performance liquid chromatography (HPLC), and light scattering.

Antibody Conjugates

The anti-PD-1 antibodies and antigen-binding fragments thereof disclosed herein may also be conjugated to a chemical moiety. The chemical moiety may be, inter alia, a polymer, a radionuclide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antigen-binding fragments thereof disclosed herein may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe.

The antibodies and antigen-binding fragments disclosed herein may also be PEGylated, for example to increase its biological (e.g., serum) half-life. To PEGylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies of the invention. See, e.g., EP 0 154 316 and EP 0 401 384.

The antibodies and antigen-binding fragments disclosed herein may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibodies and antigen-binding fragments thereof of the invention may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibodies and antigen-binding fragments thereof of the invention to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982) *Histochem. and Cytochem.* 30:407. Methods for conjugating antibodies and fragments are conventional and very well known in the art.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dinitrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

Therapeutic Uses of Anti-PD-1 Antibodies

Further provided are methods for treating subjects, including human subjects, in need of treatment with the isolated antibodies or antigen-binding fragments thereof disclosed herein. In one embodiment of the invention, such subject suffers from an infection or an infectious disease. In another embodiment of the invention, such subject suffers from cancer. In one embodiment the cancer is, e.g., osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the cancer is metastatic cancer, e.g., of the varieties described above.

In an embodiment, the invention provides methods for treating subjects using an anti-PD-1 antibody or antigen-binding fragment thereof of the invention, wherein the subject suffers from a viral infection. In one embodiment, the viral infection is infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, the invention provides methods for treating subjects using an anti-PD-1 antibody or antigen-binding fragment thereof of the invention, wherein the subject suffers from a bacterial infection. In one embodiment, the bacterial infection is infection with a bacterium selected from the group consisting of *Chlamydia*, rickettsial bacteria, mycobacteria, staphylococci, streptococci, pneumonococci, meningococci and gonococci, klebsiella, proteus, serratia, pseudomonas, *Legionella, Corynebacterium diphtheriae, Salmonella, bacilli, Vibrio cholerae, Clostridium tetan, Clostridium botulinum, Bacillus anthricis, Yersinia pestis, Mycobacterium leprae, Mycobacterium lepromatosis*, and *Borriella*.

In an embodiment, the invention provides methods for treating subjects using an anti-PD-1 antibody or antigen-binding fragment thereof of the invention, wherein the subject suffers from a fungal infection. In one embodiment, the fungal infection is infection with a fungus selected from the group consisting of *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*.

In an embodiment, the invention provides methods for treating subjects using an anti-PD-1 antibody or antigen-binding fragment thereof of the invention, wherein the subject suffers from a parasitic infection. In one embodiment, the parasitic infection is infection with a parasite selected from the group consisting of *Entamoeba histolytica, Balantidium coli, Naegleria fowleri, Acanthamoeba, Giardia lambia, Cryptosporidium, Pneumocystis carinii, Plasmodium vivax, Babesia microti, Trypanosoma brucei, Trypanosoma cruzi, Leishmania donovani, Toxoplasma gondii* and *Nippostrongylus brasiliensis*.

A "subject" may be a mammal such as a human, dog, cat, horse, cow, mouse, rat, monkey (e.g., cynomolgus monkey, e.g., *Macaca fascicularis*) or rabbit. In preferred embodiments of the invention, the subject is a human subject.

In particular embodiments, the antibodies or antigen-binding fragments thereof disclosed herein may be used alone, or in association with other, further therapeutic agents and/or therapeutic procedures, for treating or preventing any disease such as cancer, e.g., as discussed herein, in a subject in need of such treatment or prevention. Compositions, e.g., pharmaceutical compositions comprising a pharmaceutically acceptable carrier, comprising such antibodies and fragments in association with further therapeutic agents are also part of the present invention.

In particular embodiments, the antibodies or antigen-binding fragments thereof disclosed herein may be used alone, or in association with tumor vaccines.

In particular embodiments, the antibodies or antigen-binding fragments thereof disclosed herein may be used alone, or in association with chemotherapeutic agents.

In particular embodiments, the antibodies or antigen-binding fragments thereof disclosed herein may be used alone, or in association with radiation therapy.

In particular embodiments, the antibodies or antigen-binding fragments thereof disclosed herein may be used alone, or in association with targeted therapies. Examples of targeted therapies include: hormone therapies, signal transduction inhibitors (e.g., EGFR inhibitors, such as cetuximab (Erbitux) and erlotinib (Tarceva)); HER2 inhibitors (e.g., trastuzumab (Herceptin) and pertuzumab (Perjeta)); BCR-ABL inhibitors (such as imatinib (Gleevec) and dasatinib (Sprycel)); ALK inhibitors (such as crizotinib (Xalkori) and ceritinib (Zykadia)); BRAF inhibitors (such as vemurafenib (Zelboraf) and dabrafenib (Tafinlar)), gene expression modulators, apoptosis inducers (e.g., bortezomib (Velcade) and carfilzomib (Kyprolis)), angiogenesis inhibitors (e.g., bevacizumab (Avastin) and ramucirumab (Cyramza), monoclonal antibodies attached to toxins (e.g., brentuximab vedotin (Adcetris) and ado-trastuzumab emtansine (Kadcyla)).

In particular embodiments, the anti-PD-1 antibodies or antigen-binding fragments thereof of the invention may be used in combination with an anti-cancer therapeutic agent or immunomodulatory drug such as an immunomodulatory receptor inhibitor, e.g., an antibody or antigen-binding fragment thereof that specifically binds to the receptor.

Thus, the present invention includes compositions comprising an anti-PD-1 antibody or antigen-binding fragment thereof of the present invention in association with one or more other antibodies that target the PD-1/PD-L1 interaction or CTLA-4/CD80-CD86 interaction. Non-limiting examples of such antibodies include, but are not limited to: pembrolizumab, nivolumab, pidilizumab, and REGN2810, MEDI-0680, PDR-001, SHR-1210, BGB-A317, PF-06801591, TSR-042, ipilimumab, tremelimumab, atezoluzimab, durvalumab, BMS-936559; as well as methods for treating or preventing cancer in a subject comprising administering an effective amount of the anti-PD-1 antibody or antigen-binding fragment thereof of the present invention and one or more other antibodies that target the PD-1/PD-L1 interaction to the subject.

Optionally, the subject is also administered a further therapeutic agent.

In an embodiment of the invention, an anti-PD-1 antibody or antigen-binding fragment thereof of the invention is in association with a Tim-3 pathway antagonist, preferably as part of a pharmaceutical composition.

In an embodiment of the invention, an anti-PD-1 antibody or antigen-binding fragment thereof of the invention is in association with a Vista pathway antagonist, preferably as part of a pharmaceutical composition.

In an embodiment of the invention, an anti-PD-1 antibody or antigen-binding fragment thereof of the invention is in association with a BTLA pathway antagonist, preferably as part of a pharmaceutical composition.

In an embodiment of the invention, an anti-PD-1 antibody or antigen-binding fragment thereof of the invention is in association with a LAG-3 pathway antagonist, preferably as part of a pharmaceutical composition.

In an embodiment of the invention, an anti-PD-1 antibody or antigen-binding fragment thereof of the invention is in association with a TIGIT pathway antagonist, preferably as part of a pharmaceutical composition.

In an embodiment of the invention, an anti-PD-1 antibody or antigen-binding fragment thereof of the invention is in association with an anti-PDL1 antibody In an embodiment of the invention, an anti-PD-1 antibody or antigen-binding fragment thereof of the invention is in association with BMS-936559, MSB0010718C or MPDL3280A), preferably as part of a pharmaceutical composition.

In an embodiment of the invention, an anti-PD-1 antibody or antigen-binding fragment thereof of the invention is in association with an anti-CTLA4 antibody, preferably as part of a pharmaceutical composition.

In an embodiment of the invention, an anti-PD-1 antibody or antigen-binding fragment thereof of the invention is in association with an anti-CS1 antibody, preferably as part of a pharmaceutical composition.

In an embodiment of the invention, an anti-PD-1 antibody or antigen-binding fragment thereof of the invention is in association with an anti-KIR2DL1/2/3 antibody, preferably as part of a pharmaceutical composition.

In an embodiment of the invention, an anti-PD-1 antibody or antigen-binding fragment thereof of the invention is in association with an anti-CD137 antibody, preferably as part of a pharmaceutical composition.

In an embodiment of the invention, an anti-PD-1 antibody or antigen-binding fragment thereof of the invention is in association with an anti-GITR antibody, preferably as part of a pharmaceutical composition.

In an embodiment of the invention, an anti-PD-1 antibody or antigen-binding fragment thereof of the invention is in association with an anti-PD-L2 antibody, preferably as part of a pharmaceutical composition.

In an embodiment of the invention, an anti-PD-1 antibody or antigen-binding fragment thereof of the invention is in association with an anti-ILT1 antibody, preferably as part of a pharmaceutical composition.

In an embodiment of the invention, an anti-PD-1 antibody or antigen-binding fragment thereof of the invention is in association with an anti-ILT2 antibody, preferably as part of a pharmaceutical composition.

In an embodiment of the invention, an anti-PD-1 antibody or antigen-binding fragment thereof of the invention is in association with an anti-ILT3 antibody, preferably as part of a pharmaceutical composition.

In an embodiment of the invention, an anti-PD-1 antibody or antigen-binding fragment thereof of the invention is in association with an anti-ILT4 antibody, preferably as part of a pharmaceutical composition.

In an embodiment of the invention, an anti-PD-1 antibody or antigen-binding fragment thereof of the invention is in association with an anti-ILT5 antibody, preferably as part of a pharmaceutical composition.

In an embodiment of the invention, an anti-PD-1 antibody or antigen-binding fragment thereof of the invention is in association with an anti-ILT6 antibody, preferably as part of a pharmaceutical composition.

In an embodiment of the invention, an anti-PD-1 antibody or antigen-binding fragment thereof of the invention is in association with an anti-ILT7 antibody, preferably as part of a pharmaceutical composition.

In an embodiment of the invention, an anti-PD-1 antibody or antigen-binding fragment thereof of the invention is in association with an anti-ILT8 antibody, preferably as part of a pharmaceutical composition.

In an embodiment of the invention, an anti-PD-1 antibody or antigen-binding fragment thereof of the invention is in association with an anti-CD40 antibody, preferably as part of a pharmaceutical composition.

In an embodiment of the invention, an anti-PD-1 antibody or antigen-binding fragment thereof of the invention is in association with an anti-OX40 antibody, preferably as part of a pharmaceutical composition.

In an embodiment of the invention, an anti-PD-1 antibody or antigen-binding fragment thereof of the invention is in association with an anti-KIR2DL1 antibody, preferably as part of a pharmaceutical composition.

In an embodiment of the invention, an anti-PD-1 antibody or antigen-binding fragment thereof of the invention is in association with an anti-KIR2DL2/3 antibody, preferably as part of a pharmaceutical composition.

In an embodiment of the invention, an anti-PD-1 antibody or antigen-binding fragment thereof of the invention is in association with an anti-KIR2DL4 antibody, preferably as part of a pharmaceutical composition.

In an embodiment of the invention, an anti-PD-1 antibody or antigen-binding fragment thereof of the invention is in association with an anti-KIR2DL5A antibody, preferably as part of a pharmaceutical composition.

In an embodiment of the invention, an anti-PD-1 antibody or antigen-binding fragment thereof of the invention is in association with an anti-KIR2DL5B antibody, preferably as part of a pharmaceutical composition.

In an embodiment of the invention, an anti-PD-1 antibody or antigen-binding fragment thereof of the invention is in association with an anti-KIR3DL1 antibody, preferably as part of a pharmaceutical composition.

In an embodiment of the invention, an anti-PD-1 antibody or antigen-binding fragment thereof of the invention is in association with an anti-KIR3DL2 antibody, preferably as part of a pharmaceutical composition.

In an embodiment of the invention, an anti-PD-1 antibody or antigen-binding fragment thereof of the invention is in association with an anti-KIR3DL3 antibody, preferably as part of a pharmaceutical composition.

In an embodiment of the invention, an anti-PD-1 antibody or antigen-binding fragment thereof of the invention is in association with an anti-NKG2A antibody, preferably as part of a pharmaceutical composition.

In an embodiment of the invention, an anti-PD-1 antibody or antigen-binding fragment thereof of the invention is in association with an anti-NKG2C antibody, preferably as part of a pharmaceutical composition.

In an embodiment of the invention, an anti-PD-1 antibody or antigen-binding fragment thereof of the invention is in association with an anti-ICOS antibody, preferably as part of a pharmaceutical composition.

In an embodiment of the invention, an anti-PD-1 antibody or antigen-binding fragment thereof of the invention is in association with an anti-SIRPα antibody, preferably as part of a pharmaceutical composition.

In an embodiment of the invention, an anti-PD-1 antibody or antigen-binding fragment thereof of the invention is in association with an anti-CD47 antibody, preferably as part of a pharmaceutical composition.

In an embodiment of the invention, an anti-PD-1 antibody or antigen-binding fragment thereof of the invention is in association with an anti-4-1 BB antibody, preferably as part of a pharmaceutical composition.

In an embodiment of the invention, an anti-PD-1 antibody or antigen-binding fragment thereof of the invention is in association with an anti-IL-10 antibody, preferably as part of a pharmaceutical composition.

In an embodiment of the invention, an anti-PD-1 antibody or antigen-binding fragment thereof of the invention is in association with an anti-TSLP antibody, preferably as part of a pharmaceutical composition.

In an embodiment of the invention, an anti-PD-1 antibody or antigen-binding fragment thereof of the invention is in association with IL-10 or PEGylated IL-10, preferably as part of a pharmaceutical composition.

In an embodiment of the invention, an anti-PD-1 antibody or antigen-binding fragment thereof of the invention is in association with an anti-APRIL antibody, preferably as part of a pharmaceutical composition.

In an embodiment of the invention, an anti-PD-1 antibody or antigen-binding fragment thereof of the invention is in association with an anti-CD27 antibody, preferably as part of a pharmaceutical composition.

In an embodiment of the invention, an anti-PD-1 antibody or antigen-binding fragment thereof of the invention is in association with a STING agonist, preferably as part of a pharmaceutical composition. The cyclic-di-nucleotides (CDNs) cyclic-di-AMP (produced by *Listeria monocyto-*

*genes* and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells which activates the TANK binding kinase (TBK1)-IRF3 and the NF-κB signaling axis, resulting in the induction of IFN-β and other gene products that strongly activate innate immunity. It is now recognized that STING is a component of the host cytosolic surveillance pathway (Vance et al., 2009), that senses infection with intracellular pathogens and in response induces the production of IFN-β, leading to the development of an adaptive protective pathogen-specific immune response consisting of both antigen-specific $CD4^+$ and $CD8^+$ T cells as well as pathogen-specific antibodies. U.S. Pat. Nos. 7,709,458 and 7,592,326; PCT Publication Nos. WO2007/054279, WO2014/093936, WO2014/179335, WO2014/189805, WO2015/185565, WO2016/096174, WO2016/145102, WO2017/027645, WO2017/027646, and WO2017/075477; and Yan et al., Bioorg. Med. Chem Lett. 18:5631-4, 2008.

In some embodiments, the antibodies or antigen binding fragments of the invention increase the activity of an immune cell. The increase of the activity of an immune cell can be detected using any method known in the art. In one embodiment, the increase in activity of an immune cell can be detected by measuring the proliferation of the immune cell. For example, an increase in activity of a T cell can be detected by measuring the proliferation of the T cell or signal transduction events such as tyrosine phosphorylation of immune receptors or downstream kinases that transmit signals to transcriptional regulators. In other embodiments, the increase in activity of an immune cell can be detected by measuring CTL or NK cell cytotoxic function on specific target cells or IFNγ cytokine responses, which are associated with stimulation of anti-tumor immunity. In yet other embodiments, the increase in activity of an immune cell can be detected by measuring T cell activation ex vivo in a sample derived from the subject. In one embodiment, the increase in T cell activity is determined by: (i) measuring SEB (*Staphylococcus* Enterotoxin B) induced production of one or more pro-inflammatory cytokines selected from the group consisting of: IL-2, TNFα, IL-17, IFNγ, IL-113, GM-CSF, RANTES, IL-6, IL-8, IL-5 and IL-13; or (ii) measuring mixed lymphocyte reactions or direct anti-CD3 mAb stimulation of T cell receptor (TCR) signaling to induce production of a cytokine selected from the group consisting of: IL-2, TNFα, IL-17, IFNγ, IL-113, GM-CSF, RANTES, IL-6, IL-8, IL-5 and IL-13. In certain embodiments, the anti-PD-1 antibody or antigen binding fragment thereof of the present invention will stimulates antigen-specific T-cell production of IL-2 and/or IFNγ and/or upregulation of CD25 and/or CD69 by at least 1.5 fold.

Additional agents which are beneficial to raising a cytolytic T cell response may be used in combination with the anti-PD-1 antibody or antigen binding fragment thereof of the present invention. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions.

Compositions for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts.

The composition can comprise a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response.

The composition can comprise a bacterial cell that is transformed to express the polypeptide or to deliver a polynucleotide which is subsequently expressed in cells of the vaccinated individual. A number of bacterial species have been developed for use as vaccines and can be used as a vaccine platform in present invention, including, but not limited to, *Shigella flexneri, Escherichia coli, Listeria monocytogenes, Yersinia enterocolitica, Salmonella typhimurium, Salmonella typhi* or *mycobacterium* species. This list is not meant to be limiting. The present invention contemplates the use of attenuated, commensal, and/or killed but metabolically active bacterial strains as vaccine platforms. In preferred embodiments the bacterium is *Listeria monocytogenes*.

In an embodiment of the invention, an anti-PD-1 antibody or antigen-binding fragment thereof of the invention with an inactivated tumor cell vaccine. By "inactivated tumor cell vaccine" is meant a tumor cell (either "autologous" or "allogeneic" to the patient) which has been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

In some embodiments, the inactivated tumor cells of the present invention are modified to express and secrete one or more heat shock proteins. For example, gp96-Ig fusion proteins can be expressed and secreted to stimulate an immune response (Yamazaki et al., The Journal of Immunology, 1999, 163:5178-5182; Strbo et al., Immunol Res. 2013 December; 57(1-3):311-25). In some embodiments the inactivated tumor cells are modified to express and secrete a gp96-Ig fusion protein.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946. A form of GM-CSF-expressing genetically modified cancer cells or a "cytokine-expressing cellular vaccine" for the treatment of pancreatic cancer is described in U.S. Pat. Nos. 6,033,674 and 5,985,290.

Other suitable cytokines which may be expressed by such inactivated tumor cells and/or bystander cells instead of, or together with, GM-CSF include, but are not limited to, one or more of CD40 ligand, FLT-3 ligand, IL-12, CCL3, CCL20, and CCL21. This list is not meant to be limiting.

In an embodiment of the invention, an anti-PD-1 antibody or antigen-binding fragment thereof of the invention is administered in conjunction with one or more vaccines intended to stimulate an immune response to one or more predetermined antigens. The antigen(s) may be administered directly to the individual, or may be expressed within the individual from, for example, a tumor cell vaccine (e.g., GVAX) which may be autologous or allogenic, a dendritic cell vaccine, a DNA vaccine, an RNA vaccine, a viral-based vaccine, a bacterial or yeast vaccine (e.g., a *Listeria monocytogenes* or *Saccharomyces cerevisiae*), etc. See, e.g., Guo et al., Adv. Cancer Res. 2013; 119: 421-475; Obeid et al., Semin Oncol. 2015 August; 42(4): 549-561. Examples of target antigens that may find use in the invention are listed in the following Table 4. The target antigen may also be a fragment or fusion polypeptide comprising an immunologically active portion of the antigens listed in the table. This list is not meant to be limiting.

TABLE 4

List of antigens for use in combination with the anti-PD-1 antibody or antigen-binding fragment thereof of the invention as described herein.

| Antigen | Reference |
|---|---|
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369).<br>WT-1 isoform B (GenBank Acc. Nos. NM_024424; NP_077742).<br>WT-1 isoform C (GenBank Acc. Nos. NM_024425; NP_077743).<br>WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein B (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |

TABLE 4-continued

List of antigens for use in combination with the anti-PD-1 antibody or antigen-binding fragment thereof of the invention as described herein.

| Antigen | Reference |
|---|---|
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |

TABLE 4-continued

List of antigens for use in combination with the anti-PD-1 antibody or antigen-binding fragment thereof of the invention as described herein.

| Antigen | Reference |
|---|---|
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, e g., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |

TABLE 4-continued

List of antigens for use in combination with the anti-PD-1 antibody or antigen-binding fragment thereof of the invention as described herein.

| Antigen | Reference |
| --- | --- |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See, e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |

Francisella tularensis antigens

| | |
| --- | --- |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of F. tularensis include, e.g., 80 antigens, including 10 kDa and 60 kDa chaperonins (Havlasova, et al. (2002) Proteomics 2: 857-86), nucleoside diphosphate kinase, isocitrate dehydrogenase, |

TABLE 4-continued

List of antigens for use in combination with the anti-PD-1 antibody or antigen-binding fragment thereof of the invention as described herein.

| Antigen | Reference |
|---|---|
| | RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |

Malarial antigens

| Antigen | Reference |
|---|---|
| Circumsporozoite protein (CSP); SSP2; HEP17; Exp-1 orthologs found in *P. falciparum*; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A`13; AJ494905; AJ490565). |

Viruses and viral antigens

| Antigen | Reference |
|---|---|
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |

TABLE 4-continued

List of antigens for use in combination with the anti-PD-1 antibody or antigen-binding fragment thereof of the invention as described herein.

| Antigen | Reference |
| --- | --- |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; |

TABLE 4-continued

List of antigens for use in combination with the anti-PD-1 antibody or
antigen-binding fragment thereof of the invention as described herein.

| Antigen | Reference |
|---|---|
| | AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(. Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A viruses of various subtypes that originate from other species:, e.g., swine influenza viruses (SIV) | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., |

TABLE 4-continued

List of antigens for use in combination with the anti-PD-1 antibody or
antigen-binding fragment thereof of the invention as described herein.

| Antigen | Reference |
|---|---|
| (e.g. H1N1) and avian influenza virus (AIV) (e.g. H5N1; H7N7; H9N2) | Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis, Streptococcus pyogenes* (Group A Strep), *Streptococcus agalactia* (Group B Strep), *Streptococcus pneumonia, Staphylococcus aureus, Escherichia coli, Haemophilus influenzae, Neisseria meningitidis, Neisseria gonorrheae, Vibrio cholerae, Salmonella* species (including *typhi, typhimurium*), *enterica* (including *Helicobactor pylori Shigella flexneri* and other Group D *shigella* species), *Burkholderia mallei, Burkholderia pseudomallei, Klebsiella pneumonia, Clostridium* species (including *C. difficile*), *Vibrio parahaemolyticus* and *V. vulnificus*. This list is not meant to be limiting.

In an embodiment of the invention, an anti-PD-1 antibody or antigen-binding fragment thereof of the invention is in association with one or more of an inhibitor (e.g., a small organic molecule or an antibody or antigen-binding fragment thereof) such as: an MTOR (mammalian target of rapamycin) inhibitor, a cytotoxic agent, a platinum agent, an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, an IDO inhibitor, a TDO inhibitor, or a farnesyl protein transferase inhibitor.

In an embodiment of the invention, an anti-PD-1 antibody or antigen-binding fragment thereof of the invention is in association with any one or more of: 13-cis-retinoic acid, 3-[5-(methylsulfonylpiperadinemethyl)-indolyl]-quinolone, 4-hydroxytamoxifen, 5-deooxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, ALT-110, altretamine, amifostine, aminoglutethimide, amrubicin, Amsacrine, anagrelide, anastrozole, angiostatin, AP-23573, ARQ-197, arzoxifene, AS-252424, AS-605240, asparaginase, AT-9263, atrasentan, axitinib, AZD1152, Bacillus Calmette-Guerin (BCG) vaccine, batabulin, BC-210, besodutox, bevacizumab, bicalutamide, Bio111, BIO140, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, Cediranib, CG-1521, CG-781, chlamydocin, chlorambucil, chlorotoxin, cilengitide, cimitidine, cisplatin, cladribine, clodronate, COL-3, CP-724714, cyclophosphamide, cyproterone, cyproteroneacetate, cytarabine, cytosinearabinoside, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, docetaxel, dovitinib, doxorubicin, droloxifene, edotecarin, yttrium-90 labeled-edotreotide, edotreotide, EKB-569, EMD121974, endostatin, enzalutamide, enzastaurin, epirubicin, epithilone B, ERA-923, Erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, Fulvestrant, galeterone, gefitinib, gemcitabine, gimatecan, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, INCB24360, INO1001, interferon, interleukin-12, ipilimumab, irinotecan, JNJ-16241199, ketoconazole, KRX-0402, lapatinib, lasofoxifene, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, marimastat, mechlorethamine, medroxyprogesteroneacetate, megestrolacetate, melphalan, mercaptopurine, mesna, methotrexate, mithramycin, mitomycin, mitotane, mitoxantrone, tozasertib, MLN8054, neovastat, Neratinib, neuradiab, nilotinib, nilutimide, nolatrexed, NVP-BEZ235, oblimersen, octreotide, ofatumumab, oregovomab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, porfimer, prednisone, procarbazine, progestins, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, thioguanine, thiotepa, ticilimumab, tipifarnib, tivozanib, TKI-258, TLK286, topotecan, toremifene citrate, trabectedin, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vinblastine, vincristine, vindesine, vinorelbine, vitaxin, vitespan, vorinostat, VX-745, wortmannin, Xr311, zanolimumab, ZK186619, ZK-304709, ZM336372, ZSTK474.

In an embodiment of the invention, an anti-PD-1 antibody or antigen-binding fragment thereof of the invention is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co,; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, an anti-PD-1 antibody or antigen-binding fragment thereof is in association with an agent which treats or prevents such a deficiency, such as, e.g., filgrastim, PEG-filgrastim, erythropoietin, epoetin alfa or darbepoetin alfa.

In an embodiment of the invention, an anti-PD-1 antibody or antigen-binding fragment thereof of the invention is administered in association with anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures. In an embodiment of the invention, the radiation therapy is brachytherapy: the temporary placement of radioactive materials within the body, usually employed to give an extra dose—or boost—of radiation to an area.

In an embodiment of the invention, a surgical procedure administered in association with an anti-PD-1 antibody or antigen-binding fragment thereof is surgical tumorectomy.

The term "in association with" indicates that the components administered in a method of the present invention (e.g., an anti-PD-1 antibody (e.g., humanized antibody) or antigen-binding fragment thereof along with one or more other agents recited herein) can be formulated into a single composition for simultaneous delivery or formulated separately into two or more compositions (e.g., a kit). Each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

Experimental and Diagnostic Uses

The anti-PD-1 antibodies and antigen-binding fragments thereof disclosed herein may be used as affinity purification agents. In this process, the anti-PD-1 antibodies and antigen-binding fragments thereof are immobilized on a solid phase such a Sephadex, glass or agarose resin or filter paper, using methods well known in the art. The immobilized antibody or fragment is contacted with a sample containing the PD-1 protein (or a fragment thereof) to be purified, and thereafter the support is washed with a suitable solvent that will remove substantially all the material in the sample except the PD-1 protein, which is bound to the immobilized antibody or fragment. Finally, the support is washed with a solvent which elutes the bound PD-1 (e.g., protein A). Such immobilized antibodies and fragments form part of the present invention.

Further provided are antigens for generating secondary antibodies which are useful for example for performing Western blots and other immunoassays discussed herein.

Anti-PD-1 antibodies (e.g., humanized antibodies) and antigen-binding fragments thereof may also be useful in diagnostic assays for PD-1 protein, e.g., detecting its expression in specific cells, tissues, or serum, e.g., tumor cells such as melanoma cells. Such diagnostic methods may be useful in various disease diagnoses.

The present invention includes ELISA assays (enzyme-linked immunosorbent assay) incorporating the use of an anti-PD-1 antibody or antigen-binding fragment thereof disclosed herein (e.g., antibody 131A or a humanized version thereof).

For example, such a method comprises the following steps:
  (a) coat a substrate (e.g., surface of a microtiter plate well, e.g., a plastic plate) with anti-PD-1 antibody or antigen-binding fragment thereof;
  (b) apply a sample to be tested for the presence of PD-1 to the substrate;
  (c) wash the plate, so that unbound material in the sample is removed;
  (d) apply detectably labeled antibodies (e.g., enzyme-linked antibodies) which are also specific to the PD-1 antigen;
  (e) wash the substrate, so that the unbound, labeled antibodies are removed;
  (f) if the labeled antibodies are enzyme linked, apply a chemical which is converted by the enzyme into a fluorescent signal; and
  (g) detect the presence of the labeled antibody.

Detection of the label associated with the substrate indicates the presence of the PD-1 protein.

In a further embodiment, the labeled antibody or antigen-binding fragment thereof is labeled with peroxidase which react with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., $^3H$) which can be detected by scintillation counter in the presence of a scintillant.

An anti-PD-1 antibody or antigen-binding fragment thereof of the invention may be used in a Western blot or immune-protein blot procedure. Such a procedure forms part of the present invention and includes e.g., optionally transferring proteins from a sample to be tested for the presence of PD-1 (e.g., from a PAGE or SDS-PAGE electrophoretic separation of the proteins in the sample) onto a membrane or other solid substrate using a method known in the art (e.g., semi-dry blotting or tank blotting); contacting the membrane or other solid substrate to be tested for the presence of bound PD-1 or a fragment thereof with an anti-PD-1 antibody or antigen-binding fragment thereof of the invention; washing the membrane one or more times to remove unbound anti-PD-1 antibody or fragment and other unbound substances; and detecting the bound anti-PD-1 antibody or fragment.

Such a membrane may take the form of a nitrocellulose or vinyl-based (e.g., polyvinylidene fluoride (PVDF)) membrane to which the proteins to be tested for the presence of PD-1 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-PD-1 antibody or fragment, the membrane is optionally blocked, e.g., with non-fat dry milk or the like so as to bind non-specific protein binding sites on the membrane.

Detection of the bound antibody or fragment indicates that the PD-1 protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody.

The anti-PD-1 antibodies and antigen-binding fragments thereof disclosed herein may also be used for immunohistochemistry. Such a method forms part of the present invention and comprises, e.g., contacting a cell (e.g., a tumor cell such as a melanoma cell) to be tested for the presence of PD-1 protein with an anti-PD-1 antibody or antigen-binding fragment thereof of the invention; and detecting the antibody or fragment on or in the cell.

If the antibody or fragment itself is detectably labeled, it can be detected directly. Alternatively, the antibody or fragment may be bound by a detectably labeled secondary antibody which is detected.

Certain anti-PD-1 antibodies and antigen-binding fragments thereof disclosed herein may also be used for in vivo tumor imaging. Such a method may include injection of a radiolabeled anti-PD-1 antibody or antigen-binding fragment thereof into the body of a patient to be tested for the presence of a tumor associated with PD-1 expression (e.g., which expresses PD-1, for example, on the tumor cell surface) followed by nuclear imaging of the body of the patient to detect the presence of the labeled antibody or fragment e.g., at loci comprising a high concentration of the antibody or fragment which are bound to the tumor. The detection of the loci indicates the presence of the PD-1$^+$ tumor and tumor cells.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) International Rev. Neurobiol. 67:385-440).

Pharmaceutical Compositions and Administration

To prepare pharmaceutical or sterile compositions of the anti-PD-1 antibodies and antigen-binding fragments of the invention, the antibody or antigen-binding fragment thereof is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications,* Marcel Dekker, NY; Lieberman, et al. (eds.) (1990) *Pharmaceutical Dosage Forms: Tablets,* Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety,* Marcel Dekker, Inc., New York, N.Y.).

Toxicity and therapeutic efficacy of the antibodies of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-PD-1 antibody or antigen-binding fragment thereof of the invention in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, intratumoral, or intraarterial.

In particular embodiments, the anti-PD-1 antibodies or antigen-binding fragments thereof of the invention can be administered by an invasive route such as by injection. In further embodiments of the invention, an anti-PD-1 antibody or antigen-binding fragment thereof, or pharmaceutical composition thereof, is administered intravenously, subcutaneously, intramuscularly, intraarterially, intratumorally, or by inhalation, aerosol delivery. Administration by noninvasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention or a pharmaceutical composition thereof. The present invention also provides an injection device comprising any of the antibodies or antigen-binding fragments of the invention or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula.

The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-PD-1 antibody or antigen-binding fragment of the invention in a local rather than systemic manner, for example, via injection of the antibody or fragment directly into a tumor, e.g., a PD-L1$^+$ tumor. Furthermore, one may administer the antibody or fragment in a targeted drug delivery system, for example, in a liposome coated with a tissue-specific antibody, targeting, for example, a tumor e.g., a PD-1$^+$ tumor, e.g., characterized by immunopathology. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies are may be desirable.

Antibodies or antigen-binding fragments thereof disclosed herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:151-144). Doses may also be provided to achieve a pre-determined target concentration of anti-PD-1 antibody in the subject's serum, such as 0.1, 0.3, 1, 3, 10, 30, 100, 300 µg/ml or more. In other embodiments, An anti-PD-1 antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an anti-PD-1 or antigen-binding fragment thereof of the invention that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

Further provided are kits comprising one or more components that include, but are not limited to, an anti-PD-1 antibody or antigen-binding fragment, as discussed herein in association with one or more additional components including, but not limited to a pharmaceutically acceptable carrier and/or a therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-PD-1 antibody or antigen-binding fragment thereof of the invention or a pharmaceutical composition thereof in one container (e.g., in a sterile glass or plastic vial) and a pharmaceutical composition thereof and/or a therapeutic agent in another container (e.g., in a sterile glass or plastic vial).

In another embodiment, the kit comprises a combination of the invention, including an anti-PD-1 antibody or antigen-binding fragment thereof of the invention along with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Detection Kits and Therapeutic Kits

As a matter of convenience, an anti-PD-1 antibody or antigen-binding fragment thereof of the invention can be provided in a kit, i.e., a packaged combination of reagents in predetermined amounts with instructions for performing the diagnostic or detection assay. Where the antibody or fragment is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemilluminescent or chromogenic product or the reduction of a chemilluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-PD-1 antibody (e.g., humanized antibody) or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating cancer and comprises an anti-PD-1 antibody (e.g., humanized antibody) or antigen-binding fragment thereof and a further therapeutic agent or a vaccine. The kit may optionally further include a syringe for parenteral, e.g., intravenous, administration. In another aspect, the kit comprises an anti-PD-1 antibody (e.g., humanized antibody) or antigen-binding fragment thereof and a label attached to or packaged with the container describing use of the antibody or fragment with the vaccine or further therapeutic agent. In yet another aspect, the kit comprises the vaccine or further therapeutic agent and a label attached to or packaged with the container describing use of the vaccine or further therapeutic agent with the anti-PD-1 antibody or fragment. In certain embodiments, an anti-PD-1 antibody and vaccine or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, mini-computers, mainframe computers, distributed computing environments that include any of the above systems or devices, or any other systems known in the art.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA, Vol.* 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Multispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875); Labrijn et al., *Proc. Natl. Acad. Sci. USA* 110: 5145-50, 2013; de Jong et al., *PLOS Biol* 14(1): e1002344, 2016 (doi: 10.1371/journal.pbio.1002344).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, 2$^{nd}$* ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

PREFERRED EMBODIMENTS

The following are preferred embodiments of the present invention, and are exemplary in nature.

Embodiment 1

A humanized antibody or antigen binding fragment thereof that binds to human programmed death-1 (PD-1)

receptor, wherein the antibody or antigen binding fragment comprises one or more, and optionally each, of:
- a heavy chain variable region CDR1 comprising the amino acid sequence of SEQ ID NO: 1 or an amino acid sequence differing from SEQ ID NO: 1 by 1, 2, or 3 conservative substitutions,
- a heavy chain variable region CDR2 comprising the amino acid sequence of SEQ ID NO: 2 or an amino acid sequence differing from SEQ ID NO: 2 by 1, 2, or 3 conservative substitutions,
- a heavy chain variable region CDR3 comprising the amino acid sequence of SEQ ID NO: 3 or an amino acid sequence differing from SEQ ID NO: 3 by 1, 2, or 3 conservative substitutions,
- a light chain variable region CDR1 comprising the amino acid sequence of SEQ ID NO: 4 or an amino acid sequence differing from SEQ ID NO: 4 by 1, 2, or 3 conservative substitutions,
- a light chain variable region CDR2 comprising the amino acid sequence of SEQ ID NO: 5 or an amino acid sequence differing from SEQ ID NO: 5 by 1, 2, or 3 conservative substitutions, and
- a light chain variable region CDR3 comprising the amino acid sequence of SEQ ID NO: 6 or an amino acid sequence differing from SEQ ID NO: 6 by 1, 2, or 3 conservative substitutions.

Embodiment 2

The antibody or antigen binding fragment of embodiment 1, wherein the antibody or antigen binding fragment comprises
- each of a heavy chain sequence comprising the amino acid sequence of SEQ ID NO: 1 or an amino acid sequence differing from SEQ ID NO: 1 by 1, 2, or 3 conservative substitutions; the amino acid sequence of SEQ ID NO: 2 or an amino acid sequence differing from SEQ ID NO: 2 by 1, 2, or 3 conservative substitutions; and the amino acid sequence of SEQ ID NO: 3 or an amino acid sequence differing from SEQ ID NO: 3 by 1, 2, or 3 conservative substitutions;
and/or
- each of a light chain sequence comprising the amino acid sequence of SEQ ID NO: 4 or an amino acid sequence differing from SEQ ID NO: 4 by 1, 2, or 3 conservative substitutions; the amino acid sequence of SEQ ID NO: 5 or an amino acid sequence differing from SEQ ID NO: 5 by 1, 2, or 3 conservative substitutions; and the amino acid sequence of SEQ ID NO: 6 or an amino acid sequence differing from SEQ ID NO: 6 by 1, 2, or 3 conservative substitutions.

Embodiment 3

The antibody or antigen binding fragment of embodiment 2, wherein the antibody or antigen binding fragment comprises one or both of:
- a heavy chain sequence comprising the amino acid sequence of SEQ ID NO: 7 or an amino acid sequence at least 95% identical thereto, or
- a heavy chain sequence comprising the amino acid sequence of SEQ ID NO: 31 or an amino acid sequence at least 95% identical thereto;
and
- a light chain sequence comprising the amino acid sequence of SEQ ID NO: 8 or an amino acid sequence at least 95% identical thereto, or
- a light chain sequence comprising the amino acid sequence of SEQ ID NO: 33 or an amino acid sequence at least 95% identical thereto.

Embodiment 4

The antibody or antigen binding fragment of embodiment 3, wherein the antibody or antigen binding fragment comprises a heavy chain sequence comprising the amino acid sequence of SEQ ID NO: 7 and a light chain sequence comprising the amino acid sequence of SEQ ID NO: 8, wherein one or both of Gln5 and Gln81 in SEQ ID NO: 7 are optionally substituted by Glu.

Embodiment 5

The antibody or antigen binding fragment of one of embodiments 1-4, wherein the antibody or antigen binding fragment comprises a heavy chain sequence comprising the amino acid sequence of SEQ ID NO: 7 which has been modified by one or more substitution mutations at residue A9, K12, I28, T30, T31, and Y32.

Embodiment 6

The antibody or antigen binding fragment of embodiment 5, wherein the substitution mutations comprise one or more of A9P, K12V, I28D, I28T, T30D, T31D, T31S, and Y32D.

Embodiment 7

The antibody or antigen binding fragment of embodiment 6, wherein the antibody or antigen binding fragment comprises a heavy chain sequence selected from the group consisting of SEQ ID NO: 7, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48 Embodiment 8. The antibody or antigen binding fragment of one of embodiments 1-7, wherein the antibody is an intact IgG.

Embodiment 9

The antibody or antigen binding fragment of embodiment 8, wherein the calculated pI of the Fab is about 8.2 and a charge at pH 7.4 of about 6.5.

Embodiment 10

The antibody or antigen binding fragment of one of embodiments 1-9, wherein the antibody or fragment thereof has one or more, and preferably each of, the following characteristics:
- binds to a cell expressing human PD-1 with an $EC_{50}$<10 nM;
- binds to a human PD-1 protein with a $K_d$<10 nM;
- cross-reacts to *Macaca fascicularis* PD-1 protein with a $K_d$<10 nM;
- inhibits binding between human PD-1 and PD-L1 with an $IC_{50}$<10 nM;
- promotes antigen-specific T-cell responses in vitro;
- mediates limited or no antibody-dependent cell-mediated cytotoxicity (ADCC) in T cells;
- mediates limited or no complement-dependent cytotoxicity (CDC) in T cells;

does not inhibit binding of 5C4 to a cell expressing human PD-1;

does not inhibit binding of h409A11 to a cell expressing human PD-1; and does not inhibit binding of H4H7798N to a cell expressing human PD-1.

Embodiment 11

An isolated nucleic acid encoding the antibody or antigen binding fragment of one of embodiments 1-10.

Embodiment 12

An expression vector comprising the isolated nucleic acid of embodiment 11.

Embodiment 13

A host cell comprising the isolated nucleic acid of embodiment 11.

Embodiment 14

The host cell of embodiment 13, which is a mammalian cell.

Embodiment 15

The host cell of embodiment 13, which is a human cell.

Embodiment 16

The host cell of embodiment 13, which is a bacterial cell.

Embodiment 17

A composition comprising the antibody or antigen binding fragment of any one of embodiments 1-10, or an expression vector according to embodiment 12, or a host cell according to one of embodiments 13-16, and a pharmaceutically acceptable carrier or diluent.

Embodiment 18

The composition of embodiment 17, further comprising one or more agents selected from the group consisting of:
an agonist of a TNF receptor protein, an Immunoglobulin-like proteins, a cytokine receptor, an integrin, a signaling lymphocytic activation molecules (SLAM proteins), an activating NK cell receptor, a Toll ligand receptor, OX40, CD2, CD7, CD27, CD28, CD30, CD40, CDS, ICAM-1, LFA-1 (CD1 1a/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 1d, ITGAE, CD103, ITGAL, ITGAM, CD1 1b, ITGAX, CD1 1c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), SLAM7, BLAME (SLAMF8), SELPLG (CD162), LTBR, LAT, GADS, SLP-76, PAG/Cbp, CD19a, and a ligand that specifically binds with CD83;

an inhibitor of PD-L1, PD-L2, CTLA4, TIM3, LAG3, CEACAM (e.g., CEACAM-1, -3 and/or -5), VISTA, BTLA, APRIL, TIGIT, LAIR1, IDO, TDO, CD160, 2B4 and/or TGFR beta;

a cyclic dinucleotide or other STING agonist;

a cell-based vaccine expressing an antigen of interest;

a polypeptide vaccine, wherein the polypeptide is an antigen of interest;

an RNA vaccine; wherein the RNA vaccine encodes a polypeptide antigen of interest;

a DNA vaccine; wherein the DNA vaccine encodes a polypeptide antigen of interest; and a viral vaccine expressing an antigen of interest.

Embodiment 19

A method of producing an antibody or antigen binding fragment comprising:
culturing a host cell according to embodiment 13 under conditions favorable to expression of the polynucleotide; and
optionally, recovering the antibody or antigen binding fragment from the host cell and/or culture medium.

Embodiment 20

A method of treating cancer in a human subject, comprising administering to the subject an effective amount of the antibody or antigen binding fragment of any one of embodiments 1-10, or an expression vector according to embodiment 12, or a host cell according to one of embodiments 13-16, optionally in association with a further therapeutic agent or therapeutic procedure.

Embodiment 21

A method of treating an infection or infectious disease in a human subject, comprising administering to the subject an effective amount of the antibody or antigen binding fragment of any one of embodiments 1-10, optionally in association with a further therapeutic agent or therapeutic procedure.

Embodiment 22

A vaccine comprising:
the antibody or antigen binding fragment of any one of embodiments 1-10, or an expression vector according to embodiment 12, or a host cell according to one of embodiments 13-16; and
an antigen or an expression system for expressing the antigen.

Embodiment 23

A vaccine according to embodiment 22, wherein the expression system for expressing the antigen is a cell-based vaccine expressing the antigen.

Embodiment 24

A vaccine according to embodiment 23, wherein the cell-based vaccine is a bacterium.

Embodiment 25

A vaccine according to embodiment 23, wherein the bacterium is selected from the group consisting of *Shigella*

*flexneri, Escherichia coli, Listeria monocytogenes, Yersinia enterocolitica, Salmonella typhimurium, Salmonella typhi* or *mycobacterium* species.

Embodiment 26

A vaccine according to one of embodiments 22-25, wherein the antibody or antigen binding fragment and the antigen or an expression system for expressing the antigen are configured as a single composition.

Embodiment 27

A vaccine according to one of embodiments 22-25, wherein the antibody or antigen binding fragment and the antigen or an expression system for expressing the antigen are configured as separate compositions for separate administration.

Embodiment 28

A method of treating cancer in a human subject, comprising administering to the subject an effective amount of the vaccine of any one of embodiments 22-27, optionally in association with a further therapeutic agent or therapeutic procedure.

Embodiment 29

A method of treating an infection or infectious disease in a human subject, comprising administering to the subject an effective amount of the vaccine of any one of embodiments 22-27, optionally in association with a further therapeutic agent or therapeutic procedure.

Embodiment 30

A method for detecting the presence of a PD-1 protein or a fragment thereof in a sample comprising contacting the sample with an antibody or fragment of any of embodiments 1-10 and detecting the presence of a complex between the antibody or fragment and the peptide; wherein detection of the complex indicates the presence of the PD-1 protein or fragment thereof.

Embodiment 31

A method of increasing the activity of an immune cell, comprising administering to a subject in need thereof an effective amount of an antibody or antigen binding fragment according to any one of embodiments 1-10, or a composition according to any one of embodiments 17 or 18, or an expression vector according to one of embodiments 13-16, or a host cell according to one of embodiments 13-16, or a vaccine of one of embodiments 22-27.

Embodiment 32

The method of embodiment 31, wherein said method is used for:
the treatment of cancer;
the treatment of an infection or infectious disease; or
as a vaccine adjuvant.

Embodiment 33

An antibody or antigen binding fragment according to any one of embodiments 1-10, or a composition of embodiment 17 or 18, or a vaccine of one of embodiments 22-27, for use in:
increasing immune cell activation;
treatment of cancer; or
treatment of an infection or infectious disease.

Embodiment 34

Use of the antibody or antigen binding fragment of embodiments 1-10, or a composition of embodiment 17 or 18, or a vaccine of one of embodiments 22-27, for the manufacture of a medicament for increasing immune cell activation; for treating cancer; or for treating an infection or infectious disease.

EXAMPLES

Example 1: Immunization and Selection of Anti-hPD-1 Antibodies

To isolate antibodies against the human PD-1 protein mice were immunized with hPDCD1 (expression construct encoding hPD-1) DNA. The cDNA encoding the full length open reading frame of hPD-1 was subcloned into the pCI-neo vector (Promega, Madison, Wis.). The sequence of the hPD-1 DNA is as follows (from NM_005018.2) (SEQ ID NO: 13):

```
atgcagatcccacaggcgccctggccagtcgtctgggcggtgctacaact
gggctggcggccaggatggttcttagactccccagacaggccctggaacc
cccccaccttctcccagccctgctcgtggtgaccgaaggggacaacgcc
accttcacctgcagcttctccaacacatcggagagcttcgtgctaaactg
gtaccgcatgagcccagcaaccagacggacaagctggccgccttcccg
aggaccgcagccagcccgccaggactgccgcttccgtgtcacacaactg
cccaacgggcgtgacttccacatgagcgtggtcagggccccggcgcaatga
cagcggcacctacctctgtggggccatctccctggcccccaaggcgcaga
tcaaagagagcctgcgggcagagctcagggtgacagagagaagggcagaa
gtgcccacagcccaccccagcccctcacccaggccagccggccagttcca
aaccctggtggttggtgtcgtgggcggcctgctgggcagcctggtgctgc
tagtctgggtcctggccgtcatctgctcccgggccgcacgagggacaata
ggagccaggcgcaccggccagcccctgaaggaggaccccctcagccgtgcc
tgtgttctctgtggactatggggagctggatttccagtggcgagagaaga
ccccggagcccccgtgccctgtgtccctgagcagacggagtatgccacc
attgtctttcctagcggaatgggcacctcatccccgcccgcaggggctc
agctgacggccctcggagtgcccagccactgaggcctgaggatggacact
gctcttggccctctga
```

Mice were immunized by gene gun immunization using a Helios Gene gun (BioRad, Hercules, Calif.) and DNA coated gold bullets (BioRad) following manufacturer's instructions. Briefly, 1 am gold particles were coated with pCI-neo-hPD1 cDNA and commercial expression vectors for mouse Flt3L and mouse GM-CSF in a 2:1:1 ratio (both from Aldevron, Fargo, N. Dak.). A total of 1 µg of plasmid DNA was used to coat 500 µg of gold particles. Specifically, 7-8 weeks old female BALB/C mice were immunized in the ears with a gene gun, receiving 3 administration cycles in both ears.

Approximately, a 1:625-3,125 anti-hPD-1 titer was detected by CELISA in mouse serum after three DNA immunizations. In the assay, all incubation steps were followed by three wash steps with PBST (PBS with 0.01% Tween 20). To this end, CHO-K1 cells (American Type Culture Collection, Manassas, Va.) were stably transfected with hPDCD1. Parental CHO-K1 or CHO-K1.hPDCD1 cells were seeded in culture medium (DMEM-F12 (Gibco) with 10% Fetal Bovine Serum (Hyclone) and Pen/Strep (Gibco)) in tissue culture plates and incubated overnight at 37° C. Subsequently, culture medium was removed and cells were incubated for 1 hour at 37° C. with serum dilutions and control antibody dilutions. Next, cells were washed with Phosphate-Buffered Saline/0.05% Tween (PBST) and incubated for 1 hour at 37° C. with 1:5,000 goat-anti-mouse IgG-HRP (Southern Biotechnology). Subsequently, cells were washed 3 times with PBST and anti-hPD1 immunoreactivity was visualized with TMB Stabilized Chromagen (Invitrogen). Reactions were stopped with 0.5 M $H_2SO_4$ and absorbances were read at 450 and 620 nm.

Mice that demonstrated reactivity against hPD-1 were immunized for a final, fourth time and sacrificed four days later. Erythrocyte-depleted spleen and lymph-node cell populations were prepared as described previously (Steenbakkers et al., 1992, *J. Immunol. Meth.* 152: 69-77; Steenbakkers et al., 1994, *Mol. Biol. Rep.* 19: 125-134) and frozen at −140° C.

To specifically select anti-hPD-1 antibody producing B-cells, a selection strategy was designed and developed that preferentially bound B-cells expressing antibodies that bind to hPD-1.5×10$^7$ ProtG Dynabeads (Invitrogen, Cat 100.07D) by incubation, 1 hour at 20° C. with 5.25 µg recombinant hPD1-Fc (R&D systems, cat #110-HG-100) in binding/wash buffer provided in the Dynabeads kit. Next, the supernatant was aspirated and beads were blocked with PBS/10% FBS by incubation for one hour at 4° C. Beads were washed 3 times with PBS/10% FBS. Finally, beads were resuspended in PBS/10% FBS.

Selected B-cells were cultured as described by Steenbakkers et al., 1994, *Mol. Biol. Rep.* 19: 125-134. Briefly, selected B-cells were mixed with 7.5% (v/v) T-cell supernatant and 50,000 irradiated (2,500 RAD) EL-4 B5 feeder cells in a final volume of 200 µl medium in a 96-well flat-bottom tissue culture plates. On day eight, supernatants were screened for hPD-1 reactivity by CELISA as described above.

PD-1 specific B cell clones were confirmed by repeat of the CELISA and in additional a ligand-blocking assay was conducted in ELISA format. Recombinant hPD-1/Fc (R&D systems; cat #1086-PD-050) was coated overnight at 4° C. on Maxisorp plates (Nunc). Next plates were blocked with PBS/i % BSA, washed three times with PBST and subsequently the supernatants of the B cell cultures were added to the wells. After 1 hour incubation at 37° C. plates were washed three times with PBST and then hPD-L1/Fc (R&D systems; cat #156-B7-100) was added to the wells. After 1 hour incubation at 37° C. and three wash steps with PBST a Biotin-labelled anti-PD-L1 antibody (eBioscience; cat #13-5983 clone MIH1) was added. This was incubated for 1 hour at 37° C. and after three wash steps with PBST Streptavidin-HRP conjugate was added to the wells and incubated for 1 hour at 37° C. Subsequently cells were washed six times with PBST and hPD-L1/Fc binding was visualized with TMB Stabilized Chromagen (Invitrogen; Cat #SB02). Reactions were stopped with 0.5 M H2SO4 and absorbances were read at 450 and 610 nm.

Subsequently, B-cell clones from the hPD-1 reactive supernatants, among them clones that produced hPD-1/hPD-L1 interaction blockers, were immortalized by mini-electrofusion following published procedures (Steenbakkers et al., 1992, J. Immunol. Meth. 152: 69-77; Steenbakkers et al., 1994, Mol. Biol. Rep. 19:125-34). Briefly, B-cells were mixed with 10$^6$ Sp2/0-Ag14 myeloma cells in Electrofusion Isomolar Buffer (Eppendorf, cat. no. 53702). Electrofusions were performed in a 50 µL fusion chamber by an alternating electric field of 30 s, 1 MHz, 15 Vrms followed by a square, high field pulse of 10 µs, 3 kV/cm and again by an alternating electric field of 30 s, 1 MHz, 15 Vrms. Contents of the chamber were transferred to hybridoma selective medium and plated in a 96-well plate under limiting dilution conditions. On day 12 following the fusions, hybridoma supernatants were screened for hPD-1 binding activity, as described above. Hybridomas that secreted antibodies in the supernatant that recognized hPD-1 were subcloned by limited dilution to safeguard their integrity and stability. Supernatants of the hybridoma cultures were used to isotype the hybridomas (Bio-rad; cat# MMT1). Recovered antibodies were all identified as mouse IgG1.

Clonal cell populations were obtained for hPD-1 hybridomas by limited dilution Stable hybridomas were cultured in serum-free media for 7-10 days; supernatants were harvested and antibodies were purified using MabSelect Sure Protein A resin according to the manufacturer's instructions (GE Healthcare). Antibody concentrations were quantified using spectrophotometry. Antibody sequences were elucidated by cloning and sequencing of variable regions of the mouse IgG hybridoma material.

The mouse IgG1 hPD-1 antibodies were characterized for binding to hPD-1, blockade of ligand binding (hPD-L1), functionality (whole blood assay with *Staphylococcus* Enterotoxin-B (SEB) and Jurkat-based reporter assay (Promega)). The antibodies were also tested for cross-reactivity with non-human primate PD-1, more specifically: *Macaca fascicularis* PD-1. In addition the antibodies were tested on potential cross-competition with 5C4 as described in U.S. Pat. No. 8,008,449 (referred to as Nivolumab) and h409A11 as described in U.S. Pat. No. 8,354,509B2 (referred to as Pembrolizumab) for binding to hPD-1. Mouse antibody hPD1.29A was selected because it bound hPD-1 and cyno PD-1 and blocked the PD-1/PD-L1 interaction, and did not compete with 5C4 or h409A11 for binding to hPD-1 (see Example 8).

Example 2: Humanized Antibody Design and CDR Grafting

The mouse hPD1.29A antibody was humanized by CDR-grafting technology (see e.g. U.S. Pat. No. 5,225,539 and Williams, D. G. et al., 2010, Antibody Engineering, volume 1, Chapter 21).

First, human germline sequences were identified using IgBLAST (Ye J. et al., 2013, Nucleic Acids Res. 41:W34-40). For the hPD1.29A $V_H$ human germline sequence, V-gene IGHV1-3*01 was identified (65.3% identity) and for the $V_L$ human germline sequence IGKV1-16*01 was identified (65.3% identity). These two germline sequences were used to directly graft the mouse CDRs.

Next, a database was constructed containing all human sequences available in the IMGT database (Lefranc, M.-P. et al., 1999, Nucleic Acid Res. 27:209-212) identifying 82,958 individual sequences. These sequences were queried using TBLASTN (2.2.30+) to identify template sequences that demonstrated the highest identify to the framework of hPD1.29A $V_H$ and $V_L$ sequences. Four $V_H$ and four $V_L$ sequences were identified that demonstrated a similarity score of 80% or higher and that displayed similar CDR lengths, preferably identical to those in hPD1.29A $V_H$ CDR1, CDR2, CDR3 and $V_L$ CDR1, CDR2 and CDR3, respectively.

For the heavy chain, the frameworks encoded by GenBank (Benson, D. A. et al., 2013, Nucleic Acids Res. 41(D1):D36-42) accession # DJ011535, DD247024, DI109259, and IGHV1-3*01 were selected as templates for straight grafting of the hPD1.29A $V_H$ CDRs, resulting in the following templates: SEQ ID NOS: 14, 15, 16, and 17, respectively. For the light chain, the frameworks encoded by GenBank accession # AY942002, DI112350, FR820880, and IGKV1-16*01 were selected as templates for straight grafting of the hPD1.29A VL CDRs, resulting in the following templates: SEQ ID NOS: 18, 19, 20, and 8. Framework and CDR definition were those as described by Kabat et al.

```
                                           SEQ ID NO: 14
EVQLVESGAEVKKPGASVKVSCKASGYIFTTYYIHWVKQAPGKGLEWIGW

IFPGDVSTQYNEKFQDKATITVDKSASTAYMELSSLRSEDTAVYYCTREA

YDYAVYWGQGTLVTVSS

SEQ ID NO: 15
EVQLQESGAEVVKPGASMKVSCKASGYIFTTYYIHWVKQAPGKNLEWIGW

IFPGDVSTQYNEKFQDKATISVDKSASTAYMELLSLTSEDSAVYYCTREA

YDYAVYWGQGTSVTVSS

SEQ ID NO: 16
EVQLVESGAEVVKPGASVKVSCKASGYIFTTYYIHWVRQAPGKGLEWIGW

IFPGDVSTQYNEKFQDKATITADESTSTAYMELSSLRSEDTAVYYCTREA

YDYAVYWGQGTTVTVSS

SEQ ID NO: 17
EVQLVQAGAEVKKPGASVKVSCKASGYRFTTYYIHWVRQAPGQRLEWMGW

IFPGDVSTQYNEKFQDKATITRDTSASTAYMELSSLRSEDTAVYYCAREA

YDYAVYWGQATLVTVSA

SEQ ID NO: 18
DIQLTQAPSSLSASVGDRVTITCKASQNVDTNVAWYQQKPGKAPKLLIYS

ASYRYSGVPSRFSGSGSGTDFTLTISSLQPEDFATYYCQQYNNYPFTFGG

GTKLEIK

SEQ ID NO: 19
DIQMTQAPSSLSASVGDRVTITCKASQNVDTNVAWYQQKPGKAPKLLIYS

ASYRYSGVPSRFSGSGSGTEFSLSISSLQPEDFATYYCQQYNNYPFTFGG

GTKVEIK

SEQ ID NO: 20
DIQMTQAPSSLSASVGDRVTITCKASQNVDTNVAWYQQKPGKAPKLLIYS

ASYRYSGVPSRFSGSGSGTDFTLTISSLQPEDFATYYCQQYNNYPFTFGG

GTKVEIK

SEQ ID NO: 8
DIQMTQAPSSLSASVGDRVTITCKASQNVDTNVAWFQQKPGKAPKSLIFS

ASYRYSGVPSRFSGSGSGTDFTLTISSLQPEDFATYYCQQYNNYPFTFGG

GTKLEIK
```

To study the effect of humanized framework residues on the structure of the Fv, a homology model of the mouse hPD1.29A Fv was made using the 'Antibody Modeling Cascade' (default parameters) within Discovery Studio 4.5. The homology model was built on basis of PDB ID 3DIF.

The CDRs were grafted in silico to study residues that are close to any of the CDRs and which might affect the loop conformation, referred as Vernier residues. Residues that might affect the loop conformation, and which are within <5 Å to the CDR surface were identified and substituted with the mouse amino acid at this position. The resulting templates were checked for the presence of post translational modification (PTM) motifs using Discovery Studio 4.5 and where possible (i.e. non-CDR, non-Vernier residues) changed to prevent a PTM.

As determined experimentally and calculated, the pI of the mouse hPD1.29A is relatively low at 6.2. The humanized $V_H$ sequences have a theoretical pI ranging between 6.6 and 7.5. Suggested on basis of the homology model, two glutamates in $V_H 1$ of hPD1.29A were replaced by two glutamines (E6Q and E81Q), resulting in an additional humanized template (SEQ ID 7). As a result of these substitutions, the theoretical pI of the Fab fragment is raised to 8.2. This resulted in an improvement in both binding and expression (see Example 3 and 4).

CDRs were grafted on each of the identified templates, expressed as a human IgG4, kappa antibody cloned in the pcDNA3.1(+) vector and transient transfection in HEK293 Free-style cells. An IgG4 version of humanized antibodies was produced, with the stabilizing Adair mutation (Angal S. et al., 1993, Mol. Immunol. 30:105-108), where Serine 241 (Kabat numbering) is converted to Proline.

Example 3: Synthesis, Expression and Purification of Humanized Constructs

The plasmids encoding the $V_H$ and $V_L$ constructs were mixed in a 1:1 ratio (30 µg in total) and transiently expressed by transfection into FreeStyle 293-F-1.1.15 human embryonic kidney cells (HEK293T/17, ATCC-CRL-11268), using 293fectin transfection reagent (Invitrogen) following the manufacturer's instructions. Cell supernatants were harvested after 7 days and tested for expression of antibody. Expression of antibody was determined using quantification with protein A biosensors in an Octet RED96 system (ForteBio).

TABLE 5

Antibody expression levels of humanized hPD-1 antibodies

| | Antibody expression (µg/ml) | | | | |
|---|---|---|---|---|---|
| | H1 | H2 | H3 | H4 | H5 |
| L1 | 1.3 | 0.85 | 2.1 | n.a. | 27 |
| L2 | 1.4 | 0.71 | 2.0 | 0.55 | 21 |
| L3 | 1.3 | 0.79 | 2.0 | 0.53 | 19 |
| L4 | 1.4 | 1.7 | 1.9 | n.a. | 25 |

Antibodies were purified using MabSelect Sure Protein A resin according to the manufacturer's instructions (GE Healthcare). Buffer was exchanged for 10 mM Histidine, 100 mM NaCl pH 5.5 buffer using Zeba desalting columns (Thermo Scientific). The concentration of purified antibodies was determined based on OD280 (Nanodrop ND-1000). Endotoxin level was determined by LAL-test according to the manufacturer's instructions (Lonza). All purified antibodies contained lower than 10 EU/mg.

Similarly three other hPD-1 antibodies were expressed as human IgG4 (S241P) kappa by transient transfection of CHO-cells and purified by Protein A Fast protein liquid chromatography (FPLC): h409A11 as described in U.S. Pat. No. 8,354,509B2, 5C4 as described in U.S. Pat. No. 8,008,449 and H4H7798N as described in US20150203579A1 (referred to as RGN-2810).

Example 4: Binding of Humanized PD-1 Antibody hPD1.29H5L4

Binding of the humanized antibodies to native hPD-1 was studied in CELISA format using CHO-K1 cells (American Type Culture Collection, Manassas, Va.) that have been stably transfected with cDNA encoding the full length open reading frame of hPDCD1 (hPD-1), subcloned into the pCI-neo vector (Promega). Parental CHO-K1 or CHO-K1.hPDCD1 cells were seeded in culture medium (DMEM-F12 (Gibco) with 10% Fetal Bovine Serum (Hyclone) and Pen/Strep (Gibco)) in tissue culture plates and incubated for 48 hours at 37° C. Subsequently culture medium was removed and cells were incubated for 1 hour at 37° C. with hPD-1 purified antibodies (10 µg/ml (=66 nM) and dilutions thereof). Next, cells were washed with Phosphate-Buffered Saline/0.05% Tween (PBST) and incubated for 1 hour at 37° C. with Goat-anti-human IgG-HRP (Southern Biotech). Subsequently, cells were washed 3 times with PBST and anti-hPD1 immunoreactivity was visualized with 100 µl TMB Stabilized Chromagen (Invitrogen). Reactions were stopped with 100 µl 0.5 M H2SO4 and absorbances were read at 450 and 610 nm. The EC50 values were calculated using Graphpad Prism 6. EC50 values represent the concentration at which 50% of the total binding signal is observed.

TABLE 6

Binding of hPD1.29H5L4 to a stable CHO-K1 cell line encoding human PD-1 compared to h409A11, 5C4 and H4H7798N:

| Antibody | EC50 (nM) AVG ± STDEV |
| --- | --- |
| hPD1.29H5L4 | 0.13 ± 0.00 |
| h409A11 | 0.09 ± 0.00 |
| 5C4 | 0.08 ± 0.02 |
| H4H7798N | 0.10 ± 0.01 |

As a confirmation of hPD-1 binding the hPD1.29H5L4 was tested for binding to human T cells. FIG. 1 depicts binding of a concentration range of hPD1.29H5L4 (solid lines) and hIgG4 (dotted lines) to CD3/CD28 stimulated PBMCs of three individual human donors. EC50 (Binding (%)=0.27 nM±0.06 nM Human CD3+ T cells were isolated from human buffy coat as follows. First, the Buffy coat was diluted to a total volume of 180 ml with PBS at room temperature. After mixing the cell suspension, aliquotes were loaded on a Ficoll-Paque Plus gradient in Sepmate tubes (Stemcell) and centrifuged at 1200 g for 10 min, at 20° C. without a brake. Next, plasma was removed by aspiration and PBMCs were recovered from the plasma/Ficoll interface. PBMCs were washed three times in PBS. Subsequently, CD3+ T cell isolation was conducted with magnetic beads (CD3+ T-cell Biotin-Ab cocktail; Miltenyi Biotec). Cells were stored in liquid nitrogen and retrieved from the freezer on the day of the experiment. Since endogenous expression of hPD-1 on resting T cells is low, the thawed CD3+ T cells were stimulated with αCD3/αCD28 coated beads (Gibco) for 48 hours. After stimulation the cells were harvested and analysed by Flow cytometry for binding of hPD1.29H5L4.

Example 5: Blockade of PD-L1 and PD-L2 by Humanized PD-1 Antibody hPD1.29H5L4

Ligand blockade by hPD1.29H5L4 was assessed in CELISA format. Parental CHO-K1 or CHO-K1.hPDCD1 cells were seeded in tissue culture plates and incubated for 72 hours at 37° C. in culture medium. Subsequently culture medium was removed and cells were incubated for 1 hour with hPD1.29H5L4 (10 µg/ml (=66 nM) and dilutions thereof) at 37° C. Next, cells were washed with PBST and incubated for 1 hour at 37° C. with biotinylated recombinant hPD-L1 Fc- or hPD-L2 Fc-protein. Cells were then washed three times with PBST followed by addition of Streptavidin-HRP conjugate on the cells, which was incubated for 1 hour at 37° C. Subsequently cells were washed six times with PBST and binding of hPD-L1 Fc and hPD-L2 Fc was visualized with 100 al TMB Stabilized Chromagen (Invitrogen). Reactions were stopped with 100 al 0.5 M $H_2SO_4$ and absorbances were read at 450 and 610 nm. IC50 for the blockade of hPD-L1 and hPD-L2 was calculated from this data. Calculated IC50 values represent the concentration at which half of the inhibition is observed. These values are comparable to that seen with 5C4.

TABLE 7

IC50 values for the blockade of hPD-L1 and hPD-L2

| | IC50 (nM; AVG ± STDEV) | |
| --- | --- | --- |
| | Blocking of hPD-L1 Fc | Blocking of hPD-L2 Fc |
| hPD1.29H5L4 | 0.70 ± 0.06 | 0.61 ± 0.16 |
| h409A11 | 0.48 ± 0.15 | 0.61 ± 0.32 |
| 5C4 | 0.49 ± 0.01 | 0.58 ± 0.08 |
| H4H7798N | 0.45 ± 0.18 | 0.57 ± 0.17 |

Figure 2A:
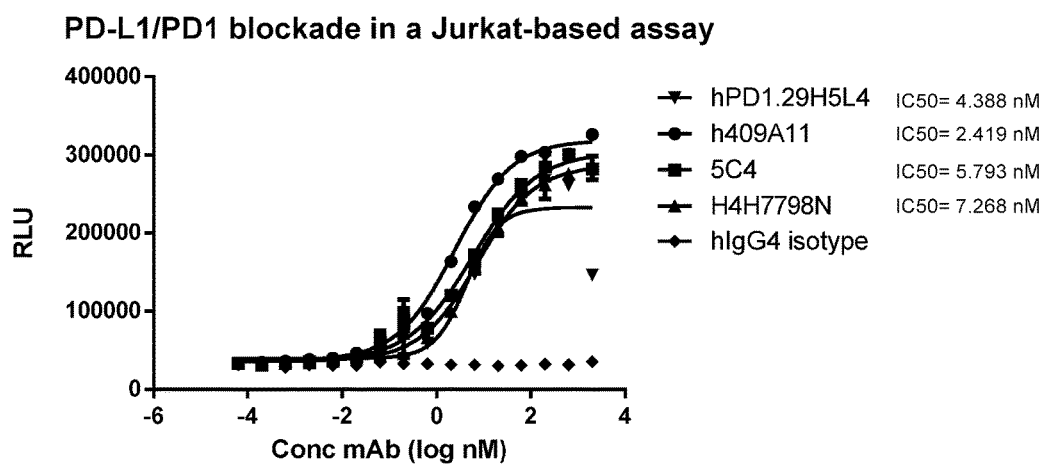
FIG. 2A shows the results of experiments in which hPD-1/hPD-L1 blocking is demonstrated using a Jurkat-based reporter assay.

Example 6: Functionality of hPD1.29H5L4 in a a Jurkat Reporter Assay and a Human Whole-Blood SEB Assay hPD1.29H5L4 was tested for its functionality in a reporter assay (Promega) based on the Jurkat T cell line. In short, stably transfected CHO cells expressing hPD-L1 were seeded in flat bottom cell culture plates and incubated overnight at 37° C. Culture medium was removed from the cells and the antibody dilutions (starting at 300 µg/ml and the dilutions thereof) were added to the cells. Subsequently stably transfected Jurkat cells, expressing human PD-1 and containing an NFAT promoter linked to a luciferase gene, were added to the plate. After six hours incubation at 37° C. the NFAT promoter activity was readout by addition of Bio-Glo™ substrate (Promega). A higher signal reflects blockade by the antibody of the PD1/PDL1 pathway that normally dampens the NFAT promoter activity. FIG. 2A depicts the results of blockade of hPD-1 and hPD-L1 interaction in the Jurkat-based assay: hPD1.29H5L4 binds hPD-1 and blocks the interaction with its ligand, hereby enhancing the Luciferase signal. As shown, hPD1.29H5L4 performs essentially equivalent to that of other PD-1 antibodies known in the art.

To study the effect of humanized hPD1.29A antibodies in whole human blood, blood was diluted 10 times in RPMI 1640 medium (Gibco, 52400) supplemented with 10% Fetal Bovine Serum (Hyclone). Diluted blood was plated in 96-well Nunclon delta surface flat bottom plates (100 al/well). Antibodies anti-hPD-1 and human IgG4 isotype control (Sigma, 14639) (200 µg/mL and dilutions thereof) were diluted in PBS and added to the diluted blood. Finally, *Staphylococcus* Enterotoxin B (Sigma S4881) diluted in RPMI 1640 medium supplemented with 10% Fetal Calf Serum was added to the wells in a final concentration of 25 ng/ml. Cells were incubated for three days at 37° C., 5% $CO_2$ and 95% humidity.

Figure 2B:
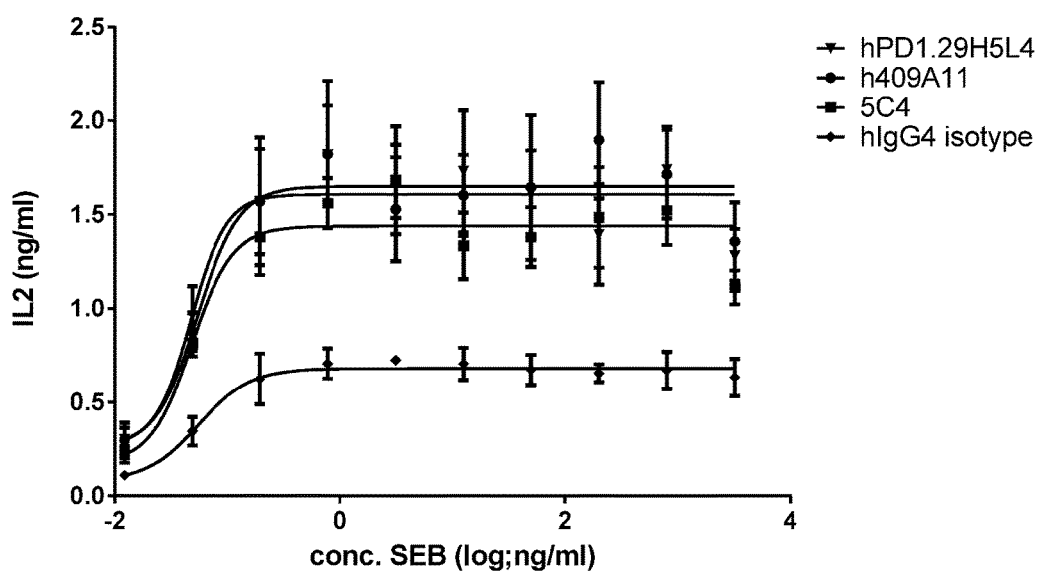
FIG. 2B shows results of experiments demonstrating that SEB-stimulated IL-2 production by healthy donor blood cells is enhanced in the presence of anti-PD-1 antibodies.

To assess the level of immune activation, IL-2 secretion levels were determined in the supernatant. To that aim, supernatants were aspirated and cleared from any cell material by centrifugation. Next, supernatants were added to Nunc maxisorp ELISA plates that had been coated with 2 µg/ml anti-hIL-2 antibody (BD Pharmingen, 555051) in PBS by overnight incubation at 4° C. Prior to addition of the supernatant, wells were emptied and blocked with 200 al/well PBS/1% BSA for one hour at Room Temperature (RT). Supernatants were incubated for one hour at RT, washed three times with PBST (PBS with 0.01% Tween 20). Subsequently, 100 al of 0.5 µg/ml of anti-hIL2-biotin (BD Pharmingen 555040) was added in PBS/PBS-1% BSA (1:1) and incubated for one hour at RT. After three washes with PBST, 1:5000 diluted streptavidin-HRP (BD Pharmingen, 554066) was added in 100 al PBS/PBS-1% BSA (1:1). After three washes with PBST and one wash with water, IL-2 was detected by addition of 100 al/well TMB stabilized chromogen (Invitrogen, SB02). Reactions were stopped with 100 al 0.5 M $H_2SO_4$ and absorbances were read at 450 and 610 nm. In this assay, recombinant human IL-2 (Sigma, H7041) was used to quantify IL-2 protein levels in the supernatants. FIG. 2B depicts the results of the whole blood SEB assay demonstrating that hPD1.29H5L4 stimulates IL-2 production.

Example 7: Cross-Reactivity of hPD1.29H5L4 with Non-Human Primate (*Macaca fascicularis*) PD-1

Binding of the hPD-1 antibodies to native cyno PD-1 was studied using CHO-K1 cells (American Type Culture Collection, Manassas, Va.) that had been transiently transfected with cDNA encoding the full length open reading frame of cyno PD-1, subcloned into the pCI-neo vector (Promega). Parental CHO-K1 or CHO-K1.cynoPD1 cells were seeded in tissue culture plates and incubated for 48 hours at 37° C. Subsequently culture medium was removed and cells were incubated for 1 hour with purified hPD-1 antibodies (10 µg/ml (=66 nM) and dilutions thereof) at 37° C. Next, cells were washed with PBST and incubated for 1 hour at 37° C. with Goat-anti-human (Jackson Immuno Research). Subsequently, cells were washed 3 times with PBST and anti-hPD1 immunoreactivity was visualized with 100 µL TMB Stabilized Chromogen (Invitrogen). Reactions were stopped with 100 µL 0.5 M H2SO4 and absorbances were read at 450 and 610 nm. Binding of hPD1.29H5L4 to *Macaca fascicularis* (*cynomolgus*) PD-1 was confirmed: EC50 0.45 nM±0.08

As a confirmation of *Macaca fiscicularis* (*cynomolgus*) PD-1 binding the hPD1.29H5L4 was tested for binding to *Macaca fascicularis* (*cynomolgus*) PBMCs. To this end *Macacaca fascicularis* (*cynomolgus*) blood was diluted 1:1 with PBS and added to 50 ml tubes containing 13 ml Lymphoprep 95%/PBS 5%. Cells were centrifuged for 30' at 450 g and 20° C. without brake. Next, plasma was removed by aspiration and PBMCs were recovered from the plasma/Ficoll interface. PBMCs were washed twice times in PBS. Cells were frozen in liquid nitrogen and retrieved from the freezer on the day of the experiment. Since endogenous expression of PD-1 on resting T cells is low thus the thawed PBMCs were stimulated with αCD3/αCD28 coated beads (Gibco) for 48 hours. After stimulation the cells were harvested and analyzed by Flow cytometry for binding of hPD1.29H5L4.

Figure 3:
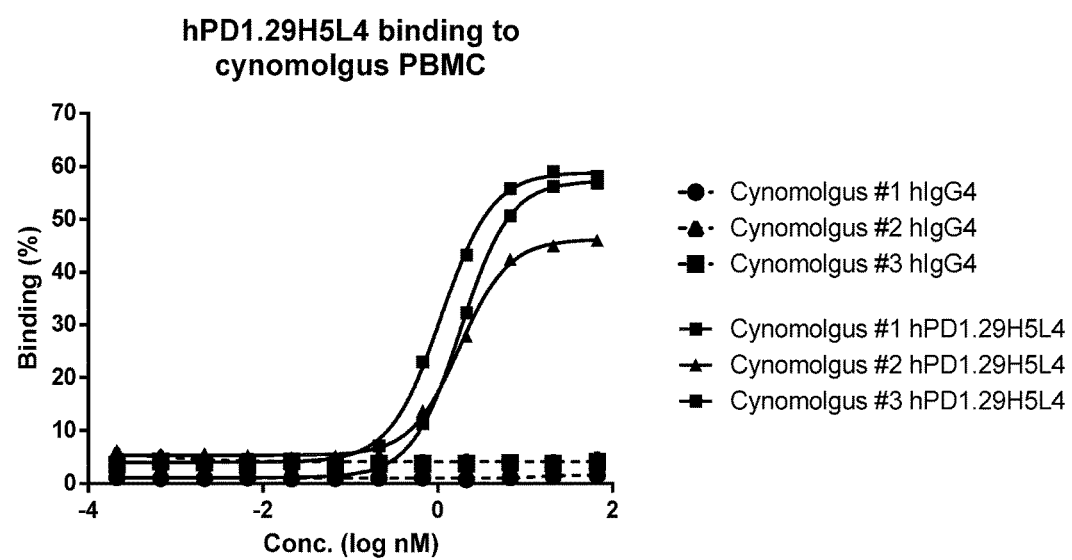
FIG. 3 shows results of experiments demonstrating that antibody hPD1.29H5L4 against human PD-1 binds to *Macaca fascicularis* PD-1 expressed on activated *Macaca fascicularis* PBMCs.

FIG. 3 depicts binding of a concentration range of hPD1.29H5L4 (solid lines) and hIgG4 (dotted lines) to CD3/CD28 stimulated *Macaca fascicularis* (*cynomolgus*) PBMCs of three individual animals. Binding EC50 of hPD1.29H5L4 to *Macaca fascicularis* (*cynomolgus*) was determined to be 1.6±0.4 nM Example 8: hPD1.29H5L4 Effector Function Assay The hPD1.29H5L4 antibody was tested for its possible effector function in the Antibody-Dependent Cell-mediated Cytotoxicity (ADCC) assay and the Complement-Dependent Cytotoxicity (CDC) assay. To this end human CD3+ T cells, isolated as described in Example 5, were used as target cells since these cells express hPD-1 and MHC-I. The latter was used as a reference antigen for a positive control antibody that induced NK cell-mediated lysis of the target cell.

The CD3+ T cells were labelled with CFSE in PBS subsequently washed twice with PBS and seeded in a flat bottom cell culture plate. Antibody dilutions of hPD1.29H5L4 and the control antibodies (hIgG1, hIgG4, µMHC-I) were added to the cells followed by addition of NK cells, derived from 3 different human donors that were added at an effector:target ratio of 4:1. After overnight incubation at 37° C. DAPI (Biolegend) was added as a marker to discriminate between live and dead cells in the Flow cytometer. ADCC was assessed by analyzing the % of viable target cells (CFSE-labelled CD3+ T cells).

Figure 4:
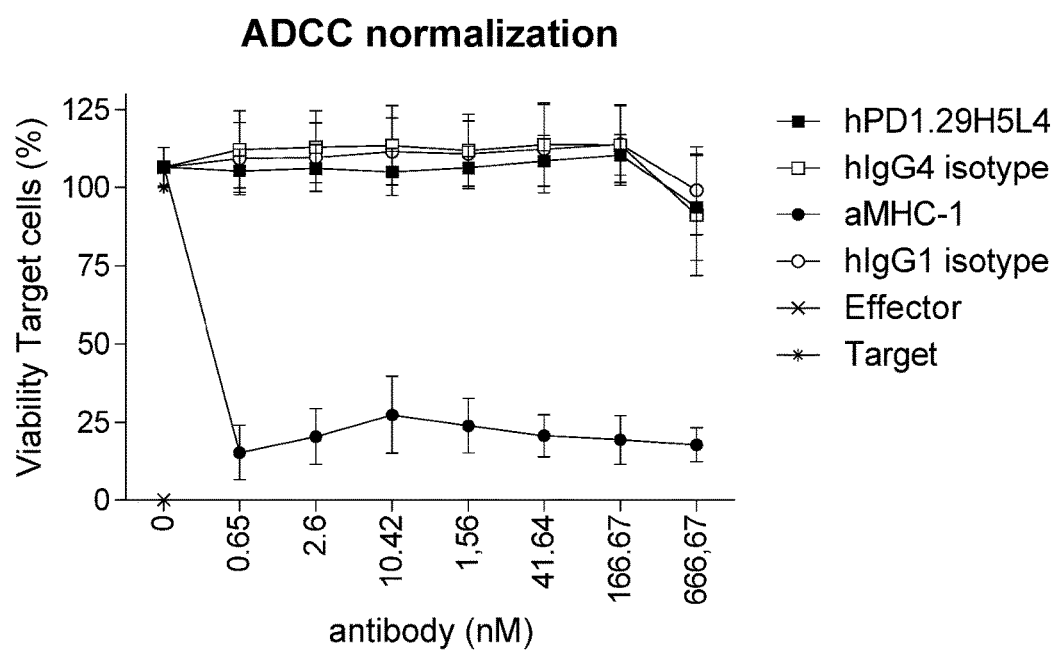
FIG. 4 shows results of experiments demonstrating the hPD1.29H5L4 antibody does not induce antibody-dependent cell-mediated cytotoxicity.
Figure 5:
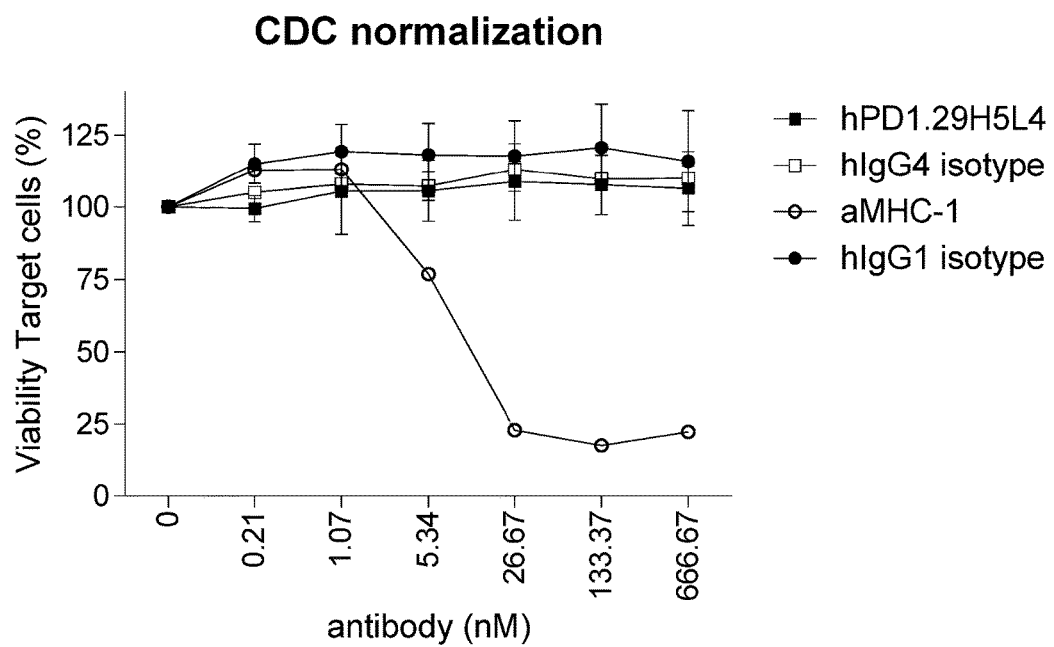
FIG. 5 shows results of experiments demonstrating the hPD1.29H5L4 antibody does not induce complement-dependent cytotoxicity.

As shown in FIG. 4, hPD1.29H5L4 does not induce ADCC in this assay. The µMHC-I antibody was used as positive control for NK-mediated cell lysis in this assay. Values are averages from the combinations of three different NK cell populations and three different CD3+ T cell populations. Similarly, FIG. 5 demonstrates that hPD1.29H5L4 limited or no CDC. The µMHC-I antibody was used as positive control for Complement-mediated cell lysis in this assay. Values are averages from three different CD3+ T cell populations.

Example 9: Comparison to Other PD-1 Antibodies

To further characterize the binding characteristics of hPD1.29H5L4, binding kinetics and equilibrium binding constants were profiled using bio-light interferometry on the Octet RED96 and compared to several antibodies known in the art. This assay was, performed by coupling hPD-1/Fc fusion protein (R&D Systems) to amine-reactive second generation biosensors (Fortebio) using standard amine chemistry. Anti-hPD-1 mAb binding to and dissociation from the biosensors was then observed at various antibody concentrations. Amine-reactive biosensors were pre-wet by immersing them in wells containing 0.1M MES pH=5.5 for 10 minutes. The biosensors were then activated using a 0.1M NHS/0.4M EDC mixture for 5 minutes. hPD-1/Fc fusion protein was coupled by immersing the biosensors in a solution of 12 ug/mL hPD-1/Fc in 0.1 M MES for 7.5 minutes. The biosensor surface was quenched using a solution of 1M ethanolamine for 5 minutes. Biosensors were equilibrated in Octet kinetics buffer (ForteBio) for 5 minutes. Association of anti-PD-1 mAbs was observed by placing the biosensors in wells containing various antibody concentrations (10-80 nM purified antibody) and monitoring interferometry for 15 minutes. Dissociation was measured after transfer of the biosensors into kinetics buffer and monitoring of the interferometry signal for 45 minutes. The assay was run with a plate temperature of 30° C. The observed on and off rates (kobs and kd) were fit using a 1:1 binding global fit model comprising all concentrations tested, and the equilibrium binding constant KD was calculated. In these experiments, hPD1.29H5L4 was shown to be substantially equivalent to other antibodies reported as having clinical utility.

TABLE 8

Binding affinity, Kon and Koff of hPD1.29H5L4
and three hPD-1 specific control antibodies

|  | KD (M) | KD Error | kon(1/Ms) | kon Error | kdis(1/s) | kdis Error |
|---|---|---|---|---|---|---|
| hPD1.29H5L4 | $1.1 \times 10^{-11}$ | $<1.0 \times 10^{-12}$ | $8.6 \times 10^{5}$ | $1.4 \times 10^{3}$ | $9.2 \times 10^{-6}$ | $<1.0 \times 10^{-7}$ |
| h409A11 | $1.5 \times 10^{-11}$ | $<1.0 \times 10^{-12}$ | $1.9 \times 10^{6}$ | $3.7 \times 10^{3}$ | $2.8 \times 10^{-5}$ | $3.3 \times 10^{-7}$ |
| 5C4 | $1.4 \times 10^{-11}$ | $<1.0 \times 10^{-12}$ | $2.1 \times 10^{6}$ | $4.3 \times 10^{3}$ | $2.9 \times 10^{-5}$ | $1.2 \times 10^{-7}$ |
| H4H7798N | $1.1 \times 10^{-11}$ | $<1.0 \times 10^{-12}$ | $1.1 \times 10^{6}$ | $2.2 \times 10^{3}$ | $1.2 \times 10^{-5}$ | $1.3 \times 10^{-7}$ |

Competition Assay (Octet)

To characterize the difference in binding site of hPD1.29H5L4 compared to h409A11, 5C4, and H4H7798N competition and peptide binding map were profiled using bio-light interferometry on the Octet RED96. Amine-reactive biosensors were pre-wet by immersing them in wells containing 0.1 M MES pH=5.5 for 10 minutes. The biosensors were then activated using a 0.1 M NHS/0.4M EDC mixture for 5 minutes. The anti-PD-1 mAb was coupled by immersing the biosensors in a solution of 80 nM mAb (hPD1.29H5L4, h409A11, 5C4, or H4H7798N) in 0.1M MES for 7.5 minutes. The biosensor surface was quenched using a solution of 1M ethanolamine for 5 minutes. Biosensors were equilibrated in Octet kinetics buffer (ForteBio) for 5 minutes. Association hPD-1/Fc was observed by placing the biosensors in wells containing a fixed hPD-1/Fc concentration (12 µg/ml) and monitoring interferometry for 15 minutes. Next an additional 5 minutes the same anti-PD-1 mAb as coupled to the biosensor was allowed to bind, to ensure binding of all available hPD-1/Fc binding sites. Competition or non-competition was determined by placing the biosensors for 10 minutes in wells containing a fixed concentration of a different anti-PD-1 mAb or a reference well containing kinetics buffer only. In this direct competition assay, binding of hPD1.29H5L4 to hPD-1 does not block binding of 5C4, h409A11, and H4H7798N to hPD-1 as shown in the table below (where binding >0 nm reflects binding):

TABLE 9

Binding of hPD1.29H5L4 or control antibodies
after initial binding of hPD1.29H5L4 on hPD-1

| First antibody | Second antibody | Binding (nm) |
|---|---|---|
| hPD1.29H5L4 | h409A11 | 0.01 |
| hPD1.29H5L4 | 5C4 | 0.01 |
| hPD1.29H5L4 | H4H7798N | 0.014 |
| hPD1.29H5L4 | hPD1.29H5L4 | 0 |
| hPD1.29H5L4 | None (1x kinetics buffer) | 0 |

Peptide Mapping (Octet)

To determine the epitope of hPD1.29H5L4 the whole extracellular domain of hPD-1 was synthesized as peptide fragments of 20 amino acids, with a N-terminal biotin tag (Sigma Aldrich). Peptides were dissolved to a concentration of 1 µM in kinetics buffer. Streptavidin biosensors were pre-wet by immersing them in wells containing kinetics buffer for 10 minutes. Peptide was coupled by immersing the biosensors in the solution of 1 µM in kinetics buffer for 5 minutes. Biosensors were equilibrated in kinetics buffer for 5 minutes. Association of anti-PD-1 mAbs was observed by placing the biosensors in wells containing a fixed antibody concentration (1 µM purified antibody) and monitoring interferometry for 15 minutes. Both 5C4 and h409A11 bound to a subset of the peptides used, while hPD1.29H5L4 and H4H7798N did not.

TABLE 10

Peptides that allowed binding of 5C4 and h409A11. "Consensus peptide"
is based on peptide sequences that overlap. The consensus peptide
(1) found for 5C4 is in line with published data
[Wang et al. 2014 doi: 10.1158/2326-6066.CIR-14-0040]:

| Antibody | Peptide number | Peptide sequence | |
|---|---|---|---|
| 5C4 | | | |
| | 54 | TSESFVLNWYRMSPSNQTDK | (SEQ ID NO: 21) |
| | 55 | NTSESFVLNWYRMSPSNQTD | (SEQ ID NO: 22) |
| | 56 | SESFVLNWYRMSPSNQTDKL | (SEQ ID NO: 23) |
| | Consensus 1 | SESFVLNWYRMSPSNQTD | (SEQ ID NO: 24) |
| | 97 | PGWFLDSPDRPWNPPTFSPA | (SEQ ID NO: 25) |
| | 98 | WFLDSPDRPWNPPTFSPALL | (SEQ ID NO: 26) |
| | Consensus 2 | WFLDSPDRPWNPPTFSPA | (SEQ ID NO: 27) |
| h409A11 | | | |
| | 55 | NTSESFVLNWYRMSPSNQTD | (SEQ ID NO: 28) |
| | 113 | TSSFSNTSESFVLNWYRMSP | (SEQ ID NO: 29) |
| | Consensus 1 | NTSESFVLNWYRMSP | (SEQ ID NO: 30) |

Example 10: Anti-hPD-1 Antibodies that Show Enhanced Production Levels

To study aggregation potential of the anti-hPD-1 antibody a homology model of hPD1.29.H5L4 Fv was constructed using the 'Antibody Modeling Cascade' (default parameters) in Discovery Studio 4.5. The homology model was built based on the coordinates of the interface template PDB ID 1T3F, the light chain template PDB ID 1UJ3 and the heavy chain template PDB ID 1I9R. The refined homology model was then used to identify potential aggregation prone regions using 'Spatial Aggregation Propensity' molecular simulations within Discovery Studio 4.5. This allowed for the identification of potential exposed spatially-adjacent aggregation prone amino acids and to perform targeted mutations on those amino acids. Single mutations on the heavy chain variable region of hPD1.29.H5L4 included A9P, K12V, I28D, I28T, T30D, T31D, T31S, Y32D. Combinations of mutations on the heavy chain variable region of hPD1.29.H5L4 included I28T_T31S, I28D_T30D, I28D_T31D, I28D_Y32D, A9P_K12V, A9P_I28T_T31S, K12V_I28T_T31S and A9P_K12V_I28T_T31S.

Primers containing the desired mutations were designed and variations were introduced in the pcDNA3.1 (+) plasmid encoding the $V_H$ construct using the Quik Site-Change II Site Directed Mutagenesis kit, according to the manufacturer's instructions (Agilent Technologies). Introduction of mutations was confirmed by DNA sequencing (Macrogen Europe). Purified plasmids encoding the $V_H$ and $V_L$ constructs were mixed in a 1:1 ratio (30 µg total) and transfected into FreeStyle 293-F-1.1.15 human embryonic kidney cells (HEK293T/17, ATCC-CRL-11268), using 293fectin transfection reagent (Invitrogen) following the manufacturer's instructions. Cell supernatants were harvested after 7 days and tested for antibody expression. Production levels were quantified using protein A biosensors in an Octet RED96 system (ForteBio) (Table 11), with the mutant antibodies showing significantly increased production levels compared to hPD1.29H5L4. Antibodies were purified using MabSelect Sure Protein A resin according to the manufacturer's instructions (GE Healthcare). Buffer was exchanged for 10 mM Histidine, 100 mM NaCl pH 5.5 buffer using Zeba desalting columns (Thermo Scientific). The concentration of purified antibodies was determined based on OD280 (Nanodrop ND-1000). Endotoxin level was determined by LAL-test according to the manufacturer's instructions (Lonza). All purified antibodies contained lower than 10 EU/mg.

TABLE 11

Antibody expression levels of mutant hPD-1 antibodies

| Antibody | Expression Mean +/− SD (µg/mL) |
|---|---|
| hPD1.29H5L4 | 19.2 +/− 4.7 |
| hPD1.29H5_A9P_L4 | 21.9 +/− 1.0 |
| hPD1.29H5_K12V_L4 | 19.8 +/− 2.3 |
| hPD1.29H5_I28D_L4 | 31.4 +/− 2.5 |
| hPD1.29H5_T30D_L4 | 29.4 +/− 1.9 |
| hPD1.29H5_T31D_L4 | 31.3 +/− 3.5 |
| hPD1.29H5_Y32D_L4 | 27.8 +/− 3.6 |
| hPD1.29H5_I28D_T30D_L4 | 30.1 +/− 3.0 |
| hPD1.29H5_I28D_T31D_L4 | 30.4 +/− 2.3 |
| hPD1.29H5_I28D_Y32D_L4 | 26.6 +/− 2.4 |
| hPD1.29H5_I28T_T31S_L4 | 31.1 +/− 6.1 |
| hPD1.29H5_A9P_K12V_L4 | 22.3 +/− 1.4 |
| hPD1.29H5_A9P_I28T_T31S_L4 | 28.3 +/− 4.4 |
| hPD1.29H5_K12V_I28T_T31S_L4 | 32.9 +/− 1.0 |
| hPD1.29H5_A9P_K12V_I28T_T31S_L4 | 43.1 +/− 4.4 |

To further characterize these mutant hPD-1 antibodies they were tested for binding to hPD-1 in CELISA format using CHO-K1 cells (American Type Culture Collection, Manassas, Va.), stably transfected with cDNA encoding the full length open reading frame of hPDCD1 (hPD-1), subcloned into the pCI-neo vector (Promega). Parental CHO-K1 or CHO-K1.hPDCD1 cells were seeded in culture medium (DMEM-F12 (Gibco) with 10% Fetal Bovine Serum (Hyclone) and Pen/Strep (Gibco)) in tissue culture plates and incubated for 48 hours at 37° C. Subsequently culture medium was removed and cells were incubated for 1 hour at 37° C. with the mutant hPD-1 antibodies (10 µg/ml (=66 nM) and dilutions thereof). Next, cells were washed with Phosphate-Buffered Saline/0.05% Tween (PBST) and incubated for 1 hour at 37° C. with Goat-anti-human IgG-HRP (Southern Biotech). Subsequently, cells were washed 3 times with PBST and anti-hPD1 immunoreactivity was visualized with 100 al TMB Stabilized Chromagen (Invitrogen). Reactions were stopped with 100 al 0.5 M H2SO4 and absorbances were read at 450 and 610 nm. Calculated EC50 values are shown in Table 12. All the hPD-1 antibodies tested displayed similar binding properties when compared to hPD1.29H5L4. Blockade of hPD-L1 binding by the mutant hPD-1 antibodies was tested in CELISA format. Parental CHO-K1 or CHO-K1.hPDCD1 cells were seeded in tissue culture plates and incubated for 72 hours at 37° C. in culture medium. Subsequently culture medium was removed and cells were incubated for 1 hour with the mutant hPD-1 antibodies (10 µg/ml (=66 nM) and dilutions thereof) at 37° C. Next, cells were washed with PBST and incubated for 1 hour at 37° C. with biotinylated recombinant hPD-L1 Fc protein. Cells were then washed three times with PBST followed by addition of Streptavidin-HRP conjugate on the cells, which was incubated for 1 hour at 37° C. Subsequently cells were washed six times with PBST and binding of hPD-L1 Fc was visualized with 100 al TMB Stabilized Chromagen (Invitrogen). Reactions were stopped with 100 al 0.5 M H2SO4 and absorbances were read at 450 and 610 nm. Calculated IC50 values in Table 12 for the blockade of hPD-L1 represent the concentration at which half of the inhibition is observed. Calculated IC50 values were comparable to that seen with hPD1.29H5L4.

TABLE 12

Binding of hPD1.29H5L4 mutants to CHO-K1.hPDCD1 and blocking of hPD-L1 binding to CHO-K1.hPDCD1 by hPD1.29H5L4 antibodies.

| Antibody | Binding EC$_{50}$ (nM) Avg +/− SD | Blocking IC$_{50}$ (nM) Avg +/− SD |
|---|---|---|
| hPD1.29H5L4 | 0.3 +/− 0.2 | 1.3 +/− 0.3 |
| hPD1.29H5_A9P_L4 | 0.4 +/− 0.1 | 1.4 +/− 0.1 |
| hPD1.29H5_K12V_L4 | 0.4 +/− 0.1 | 1.4 +/− 0.1 |
| hPD1.29H5_I28D_L4 | 0.3 +/− 0.1 | 1.6 +/− 0.2 |
| hPD1.29H5_T30D_L4 | 0.3 +/− 0.1 | 1.6 +/− 0.3 |
| hPD1.29H5_T31D_L4 | 0.4 +/− 0.1 | 1.7 +/− 0.2 |
| hPD1.29H5_Y32D_L4 | 0.3 +/− 0.2 | 1.4 +/− 0.1 |

TABLE 12-continued

Binding of hPD1.29H5L4 mutants to CHO-K1.hPDCD1
and blocking of hPD-L1 binding to CHO-K1.hPDCD1
by hPD1.29H5L4 antibodies.

| Antibody | Binding EC$_{50}$ (nM) Avg +/− SD | Blocking IC$_{50}$ (nM) Avg +/− SD |
|---|---|---|
| hPD1.29H5_I28D_T30D_L4 | 0.4 +/− 0.1 | 1.6 +/− 0.1 |
| hPD1.29H5_I28D_T31D_L4 | 0.4 +/− 0.1 | 1.4 +/− 0.2 |
| hPD1.29H5_I28D_Y32D_L4 | 0.4 +/− 0.1 | 1.3 +/− 0.2 |
| hPD1.29H5_I28T_T31S_L4 | 0.3 +/− 0.2 | 1.1 +/− 0.2 |
| hPD1.29H5_A9P_K12V_L4 | 0.4 +/− 0.1 | 1.3 +/− 0.3 |
| hPD1.29H5_A9P_I28T_T31S_L4 | 0.3 +/− 0.1 | 1.2 +/− 0.1 |
| hPD1.29H5_K12V_I28T_T31S_L4 | 0.3 +/− 0.2 | 1.2 +/− 0.2 |
| hPD1.29H5_A9P_K12V_I28T_T31S_L4 | 0.3 +/− 0.1 | 1.2 +/− 0.2 |

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention claimed is:

1. A humanized antibody or antigen binding fragment thereof that binds to human programmed death-1 (PD-1) receptor, wherein the antibody or antigen binding fragment comprises:
an immunoglobulin heavy chain variable domain comprising:
a heavy chain variable region CDR1 comprising the amino acid sequence TYYIH (SEQ ID NO: 1) or an amino acid sequence differing from SEQ ID NO: 1 by substitution of T with D or S, or substitution of the first Y with D,
a heavy chain variable region CDR2 comprising the amino acid sequence WIFPGDVSTQYNEKFQD (SEQ ID NO: 2), and
a heavy chain variable region CDR3 comprising the amino acid sequence EAYDYAVY (SEQ ID NO: 3); and
an immunoglobulin light chain variable domain comprising:
a light chain variable region CDR1 comprising the amino acid sequence KASQNVDTNVA (SEQ ID NO: 4),
a light chain variable region CDR2 comprising the amino acid sequence SASYRYS (SEQ ID NO: 5), and
a light chain variable region CDR3 comprising the amino acid sequence QQYNNYPFT (SEQ ID NO: 6).

2. The antibody or antigen binding fragment of claim 1, wherein the antibody or antigen binding fragment comprises:
a heavy chain variable domain sequence comprising the amino acid sequence of SEQ ID NO: 7 or an amino acid sequence at least 95% identical thereto, or
a heavy chain variable domain sequence comprising the amino acid sequence of SEQ ID NO: 31 or an amino acid sequence at least 95% identical thereto; and
a light chain variable region sequence comprising the amino acid sequence of SEQ ID NO: 8 or an amino acid sequence at least 95% identical thereto, or
a light chain variable region sequence comprising the amino acid sequence of SEQ ID NO: 33 or an amino acid sequence at least 95% identical thereto.

3. The antibody or antigen binding fragment of claim 2, wherein the antibody or antigen binding fragment comprises a heavy chain variable domain sequence comprising the amino acid sequence of SEQ ID NO: 7 and a light chain variable region sequence comprising the amino acid sequence of SEQ ID NO: 8 and wherein one or both of Gln6 and Gln82 in SEQ ID NO: 7 are optionally substituted by Glu.

4. The antibody or antigen binding fragment of claim 2, wherein the antibody or antigen binding fragment comprises a heavy chain variable domain sequence comprising the amino acid sequence of SEQ ID NO: 7, wherein one or both of Gln6 and Gln82 in SEQ ID NO: 7 are optionally substituted by Glu, and wherein SEQ ID NO: 7 has been modified by one or more substitution mutations at residue A9, K12, I28, T30, T31, and Y32.

5. The antibody or antigen binding fragment of claim 4, wherein the one or more substitution mutations are selected from the group consisting of A9P, K12V, I28D, I28T, T30D, T31D, T31S, and Y32D.

6. The antibody or antigen binding fragment of claim 3, wherein the antibody or antigen binding fragment comprises a heavy chain variable domain sequence selected from the group consisting of SEQ ID NO: 7, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48.

7. The antibody or antigen binding fragment of claim 1, wherein the antibody is an intact IgG.

8. The antibody or antigen binding fragment of claim 7, wherein the calculated pI of the Fab is about 8.2 and a charge at pH 7.4 of about 6.5.

9. The antibody or antigen binding fragment of claim 3, wherein the antibody or fragment thereof has one or more of the following characteristics:
binds to a cell expressing human PD-1 with an $EC_{50}$<10 nM;
binds to a human PD-1 protein with a $K_d$<10 nM;
cross-reacts to *Macaca fascicularis* PD-1 protein with a $K_d$<10 nM;
inhibits binding between human PD-1 and PD-L1 with an $IC_{50}$<10 nM;
promotes antigen-specific T-cell responses in vitro;
mediates limited or no antibody-dependent cell-mediated cytotoxicity (ADCC) in T cells;
mediates limited or no complement-dependent cytotoxicity (CDC) in T cells;
does not inhibit binding of 5C4 to a cell expressing human PD-1;
does not inhibit binding of h409A11 to a cell expressing human PD-1; and does not inhibit binding of H4H7798N to a cell expressing human PD-1.

10. A composition comprising an antibody or antigen binding fragment of claim 1 and a pharmaceutically acceptable carrier or diluent, optionally further comprising one or more agents selected from the group consisting of:
an agonist of a TNF receptor protein, an Immunoglobulin-like proteins, a cytokine receptor, an integrin, a signaling lymphocytic activation molecules (SLAM proteins), an activating NK cell receptor, a Toll ligand receptor, OX40, CD2, CD7, CD27, CD28, CD30, CD40, CDS, ICAM-1, LFA-1 (CD1 1a/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 1d, ITGAE, CD103, ITGAL, ITGAM, CD1 1b, ITGAX, CD1 1c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), SLAM7, BLAME (SLAMF8), SELPLG (CD162), LTBR, LAT, GADS, SLP-76, PAG/Cbp, CD19a, and a ligand that specifically binds with CD83;

an inhibitor of PD-L1, PD-L2, CTLA4, TIM3, LAGS, a CEACAM, VISTA, BTLA, APRIL, TIGIT, LAIR1, IDO, TDO, CD160, 2B4 and/or TGFR beta;

a cyclic dinucleotide or other STING agonist;

a cell-based vaccine;

a polypeptide vaccine;

an RNA vaccine;

a DNA vaccine; and a viral vaccine.

11. The composition of claim 10, wherein the inhibitor of CEACAM inhibits CEACAM-1, CEACAM-3 or CEACAM-5.

12. A composition comprising an antibody or antigen binding fragment of claim 3 and a pharmaceutically acceptable carrier or diluent, optionally further comprising one or more agents selected from the group consisting of:

an agonist of a TNF receptor protein, an Immunoglobulin-like proteins, a cytokine receptor, an integrin, a signaling lymphocytic activation molecules (SLAM proteins), an activating NK cell receptor, a Toll ligand receptor, OX40, CD2, CD7, CD27, CD28, CD30, CD40, CDS, ICAM-1, LFA-1 (CD1 1a/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 1d, ITGAE, CD103, ITGAL, ITGAM, CD1 1b, ITGAX, CD1 1c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), SLAM7, BLAME (SLAMF8), SELPLG (CD162), LTBR, LAT, GADS, SLP-76, PAG/Cbp, CD19a, and a ligand that specifically binds with CD83;

an inhibitor of PD-L1, PD-L2, CTLA4, TIM3, LAGS, a CEACAM, VISTA, BTLA, APRIL, TIGIT, LAIR1, IDO, TDO, CD160, 2B4 and/or TGFR beta;

a cyclic dinucleotide or other STING agonist;

a cyclic dinucleotide or other STING agonist;

a cell-based vaccine;

a polypeptide vaccine;

an RNA vaccine;

a DNA vaccine; and a viral vaccine.

13. The composition of claim 12, wherein the inhibitor of CEACAM inhibits CEACAM-1, CEACAM-3 or CEACAM-5.

* * * * *